(12) United States Patent
Wang et al.

(10) Patent No.: US 10,947,202 B2
(45) Date of Patent: Mar. 16, 2021

(54) SODIUM ION CHANNEL INHIBITORS AND PHARMACEUTICALLY ACCEPTABLE SALTS AND POLYMORPHS THEREOF AND USES THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Zheng Wang, Shanghai (CN); Taotao Jiang, Shanghai (CN); Jibiao Wang, Shanghai (CN)

(73) Assignees: SHANGHAI HAIYAN PHARMACEUTICAL TECHNOLOGY CO., LTD.; YANGTZE RIVER PHARMACEUTICAL GROUP CO., LTD.

( * ) Notice: Subject to any disclaimer, the term of this patent is extended or adjusted under 35 U.S.C. 154(b) by 0 days.

(21) Appl. No.: 16/596,324

(22) Filed: Oct. 8, 2019

(65) Prior Publication Data
US 2020/0048209 A1 Feb. 13, 2020

Related U.S. Application Data

(63) Continuation of application No. PCT/CN2018/092895, filed on Jun. 26, 2018.

(30) Foreign Application Priority Data

Jul. 24, 2017 (CN) .......................... 201710607309.0

(51) Int. Cl.
*C07D 241/04* (2006.01)
(52) U.S. Cl.
CPC ........ *C07D 241/04* (2013.01); *C07B 2200/13* (2013.01)

(58) Field of Classification Search
CPC .......................... C07D 241/04; C07B 2200/13
See application file for complete search history.

(56) References Cited

FOREIGN PATENT DOCUMENTS

| WO | WO 2015/078374 A1 | 6/2015 | |
|----|-------------------|--------|---|
| WO | WO 2016/124139 A1 | 8/2016 | |
| WO | WO 2017/133591 * | 8/2017 | ........... C07D 207/08 |
| WO | WO 2017/133591 A1 | 8/2017 | |

OTHER PUBLICATIONS

International Search Report for PCT/CN2018/092895, dated Sep. 18, 2018, including its English translation, 9 pages.

\* cited by examiner

*Primary Examiner* — Erick A Leeser
(74) *Attorney, Agent, or Firm* — Adsero IP

(57) ABSTRACT

The present disclosure discloses sodium ion channel inhibitors, pharmaceutically acceptable salts and polymorphs thereof, and uses thereof. Specifically, the present disclosure discloses a polymorph of a compound of formula (X) and a preparation method thereof. The preparation method of the present disclosure is simple in operation and suitable for industrialization. The polymorph prepared by the preparation method has advantages of good stability, low hygroscopicity and high water solubility.

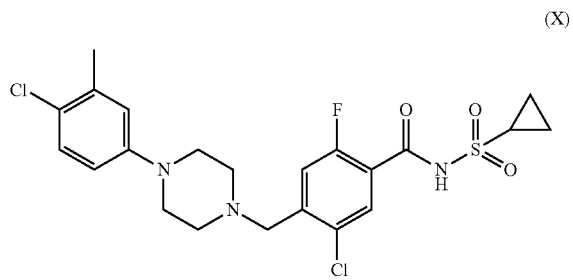

(X)

9 Claims, 29 Drawing Sheets

SODIUM ION CHANNEL INHIBITORS AND PHARMACEUTICALLY ACCEPTABLE SALTS AND POLYMORPHS THEREOF AND USES THEREOF

CROSS REFERENCE TO RELATED APPLICATIONS

This application is a continuation application for International Application PCT/CN2018/092895, filed on Jun. 26, 2018, which claims the priority benefit of Chinese Patent Application No. 201710607309.0, titled "SODIUM ION CHANNEL INHIBITORS AND PHARMACEUTICALLY ACCEPTABLE SALTS AND POLYMORPHS THEREOF AND USES THEREOF" and filed on Jul. 24, 2017. The entireties of both applications are incorporated by reference herein for all purposes.

TECHNICAL FIELD

The present disclosure belongs to the technical field of medical chemistry. In particular, the present disclosure relates to the polymorphs of 5-chloro-4-((4-(4-chloro-3-methylphenyl) piperazin-1-yl)methyl)-N-(cyclopropylsulfonyl)-2-fluorobenzamide, the preparation method thereof and the pharmaceutical compositions prepared therefrom.

BACKGROUND

Recently, Cox et al in the UK reported an unexpected result for the first time in *Nature* that the mutation of SCN9A gene which encodes a voltage-gated Nav1.7 channel leads to the painlessness of genetic individuals. The genetically mutated individuals congenitally lost pain, but the other functions of the body were completely normal. In addition, recent studies have shown that the voltage-gated Nav1.7 channel expressed in DRG neurons is involved in the production of pain signals and functions as a gate to control the introduction of pain signals. The study suggests that the Nav1.7 channel may become a drug target that is used in a selective treatment of pain without side effects.

There is increasing evidence of body that Nav1.7 plays an important role in a variety of pain states (including acute, chronic, inflammatory and/or neuropathic pain). In humans, Nav1.7 protein accumulates in neuromas, especially neuromas that cause pain. Mutations with increased Nav1.7 function (whether hereditary or sporadic) have been considered to involve primary erythematous limb pain (a condition characterized by cautery and inflammation of the extremities), and suddenly extreme pain. The reported results that the non-selective sodium channel blockers lidocaine and mexiletine can alleviate the symptoms of hereditary erythematous limb pain, and carbamazepine can effectively reduce the number and severity of PEPD attacks are consistent with the above observations. Additional evidence for the role of Nav1.7 in pain can be found in the phenotype of a loss-of-function mutation in the SCN9A gene. Follow-up studies have been shown to result in the loss of function of the SCN9A gene and many different mutations in CIP phenotype.

Since Nav1.7 is specifically expressed in DRG sensory neurons but not in other tissues such as cardiomyocytes and the central nervous system, the development of specific blockers for the treatment of chronic pain will not only increase efficacy but also reduce side effects, and selective inhibitors of Nav1.7 ion channel can be used for almost all kinds of pain treatment.

Although there are many patents reporting various Nav1.7 ion channel inhibitors, after intensive research it is found that some existing Nav1.7 ion channel inhibitors are insufficient in selectivity for other ion channels, such as potassium ion channels, and insufficient in human liver microsomal stability. As the influence of the cardiotoxicity associated with the HERG potassium channel and the human liver microsomal stability index predicting the liver clearance of the compound on drug development are crucial, therefore, there is an urgent need to develop safer and more effective analgesics, which have higher efficacy and fewer side effects. The present disclosure developed a variety of salts and crystal forms of Nav1.7 ion channel inhibitors which have good metabolism and high selectivity based on the foregoing work, these inhibitors contribute to further drug development.

SUMMARY

In the first aspect of the present disclosure, a compound of formula (X) or a pharmaceutically acceptable salt or a polymorph thereof is provided:

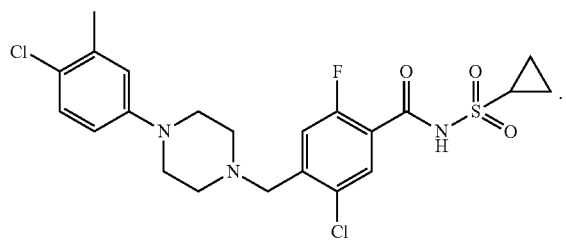

In another preferred embodiment, the pharmaceutically acceptable salt is an acid salt or a basic salt, wherein the acid salt is selected from the group consisting of hydrochloride, sulfate, phosphate, acetate, L-lactate, maleate, fumarate, succinate, L-malate, adipate, L-tartrate, hippurate, citrate, mucate, glycollate, D-glucuronate, benzoate, gentisate, nicotinate, ethanedisulphonate, oxalate, methanesulfonate, benzenesulfonate, 2-hydroxyethanesulfonate and hydrobromide; the basic salt is selected from the group consisting of triethanolamine salt, sodium salt and potassium salt.

In another preferred embodiment, the pharmaceutically acceptable acid salt is selected from the group consisting of hydrochloride, sulfate, hydrobromide, phosphate, methanesulfonate, maleate, L-tartrate, citrate and fumarate. In another preferred embodiment, the pharmaceutically acceptable basic salt is selected from the group consisting of sodium salt and potassium salt.

In another preferred embodiment, the pharmaceutically acceptable acid salt is selected from the group consisting of hydrochloride, hydrobromide, methanesulfonate and maleate.

In another preferred embodiment, the sodium salt or potassium salt is prepared from a base selected from the group consisting of sodium hydroxide and potassium hydroxide.

In another preferred embodiment, the pharmaceutically acceptable salt is selected from the group consisting of hydrochloride, maleate and potassium salt.

In another preferred embodiment, the compound of formula X, or its pharmaceutically acceptable salt, or its polymorph is in an anhydrous form, hydrate form or solvate form.

In another preferred embodiment, the polymorph is a polymorph of the compound of formula X.

In another preferred embodiment, the polymorph is a polymorph of a pharmaceutically acceptable salt of the compound of formula X, and the pharmaceutically acceptable salt is selected from the group consisting of hydrochloride, sulfate, hydrobromide, phosphate, methanesulfonate, maleate, L-tartrate, citrate, fumarate, sodium salt and potassium salt.

In another preferred embodiment, the polymorph is a polymorph of a pharmaceutically acceptable salt of the compound of formula X, and the pharmaceutically acceptable salt is selected from the group consisting of hydrochloride, hydrobromide, methanesulfonate, maleate, sodium salt and potassium salt.

In another preferred embodiment, the polymorph is a polymorph of a pharmaceutically acceptable salt of the compound of formula X, and the pharmaceutically acceptable salt is selected from the group consisting of hydrochloride, maleate and potassium salt.

In another preferred embodiment, the pharmaceutically acceptable salt of the compound of formula X is in anhydrous form.

In another preferred embodiment, the polymorph is in anhydrous form.

In another preferred embodiment, the pharmaceutically acceptable salt is hydrochloride, wherein the molar ratio of hydrochloric acid to the compound of formula X is (0.5-2):1, preferably (0.5-1.5):1.

In another preferred embodiment, the pharmaceutically acceptable salt is hydrobromide, wherein the molar ratio of hydrobromic acid to the compound of formula X is (0.8-3.5):1, preferably (1.0-3.0):1.

In another preferred embodiment, the pharmaceutically acceptable salt is methanesulfonate, wherein the molar ratio of methanesulfonic acid to the compound of formula X is (0.5-3.5):1, preferably (0.6-3.0):1.

In another preferred embodiment, the pharmaceutically acceptable salt is maleate, wherein the molar ratio of maleic acid to the compound of formula X is (0.6-2):1, preferably (0.7-1.9):1.

In another preferred embodiment, the pharmaceutically acceptable salt is sodium hydroxide salt, wherein the molar ratio of sodium hydroxide to the compound of formula X is (0.3-3):1, preferably (0.4-2.8):1.

In another preferred embodiment, the pharmaceutically acceptable salt is potassium hydroxide salt, wherein the molar ratio of potassium hydroxide to the compound of formula X is (0.5-3.5):1, preferably (0.6-3.3):1.

In another preferred embodiment, the polymorph is A crystalline form of the hydrochloride of compound of formula X, i.e. crystal form A, which has an X-ray powder diffraction pattern having peaks at the diffraction angle 2θ(°) values of the following group A1: 12.19±0.20, 16.30±0.20, 17.76±0.20, 18.61±0.20, 23.23±0.20, 25.17±0.20.

In another preferred embodiment, the X-ray powder diffraction pattern of crystal form A further includes peaks at two or more diffraction angle 2θ(°) values selected from the following group A2: 13.52±0.20, 14.39±0.20, 19.65±0.20, 20.26±0.20, 27.23±0.20, 29.48±0.20 and 32.10±0.20.

In another preferred embodiment, the X-ray powder diffraction pattern of crystal form A has peaks at six or more or all (such as 6, 7, 8, 9, 10, 11, 12, 13, etc.) 2θ(°) values selected from the groups A1 and A2.

In another preferred embodiment, the X-ray powder diffraction pattern of crystal form A has peaks at 2θ(°) values shown in Table 1 below, and the relative intensities of the respective peaks are shown in Table 1.

TABLE 1

| 2θ(°) | d value [Å] | relative intensity (%) |
|---|---|---|
| 12.19 | 7.25 | VS |
| 13.52 | 6.55 | S |
| 14.39 | 6.15 | S |
| 16.30 | 5.43 | VS |
| 17.76 | 4.99 | VS |
| 18.61 | 4.76 | VS |
| 19.65 | 4.52 | S |
| 20.26 | 4.38 | S |
| 23.23 | 3.83 | VS |
| 25.17 | 3.54 | VS |
| 27.23 | 3.27 | S |
| 29.48 | 3.03 | S |
| 32.10 | 2.79 | S |

In another preferred embodiment, the X-ray powder diffraction pattern of crystal form A is substantially as shown in FIG. 1A.

In another preferred embodiment, the molar ratio of hydrochloric acid to the compound of formula X in crystal form A is (0.5-2):1, preferably (0.5-1.5):1.

In another preferred embodiment, the crystal form A further has one or more characteristics selected from the group consisting of:
(1) the differential scanning calorimetry analysis spectrum being substantially as shown in FIG. 1B;
(2) the thermogravimetric analysis spectrum being substantially as shown in FIG. 1C; and
(3) the crystal form A having a melting point of 240-255° C., preferably 243-252° C.

In another preferred embodiment, the crystal form A is in an anhydrous form.

In another preferred embodiment, the polymorph is B crystalline form of the hydrobromide of compound of formula X, i.e. crystal form B, which has an X-ray powder diffraction pattern having a peak at the diffraction angle 2θ(°) value of the following group B1: 12.40±0.20.

In another preferred embodiment, the X-ray powder diffraction pattern of crystal form B further includes peaks at two or more diffraction angle 2θ(°) values selected from the following group B2: 8.27±0.20, 13.28±0.20, 16.53±0.20, 18.36±0.20, 18.68±0.20, 19.68±0.20, 20.07±0.20, 20.73±0.20, 22.60±0.20, 24.92±0.20 and 25.35±0.20.

In another preferred embodiment, the X-ray powder diffraction pattern of crystal form B further includes peaks at two or more diffraction angle 2θ(°) values selected from the following group B3: 17.43±0.20.

In another preferred embodiment, the X-ray powder diffraction pattern of crystal form B has peaks at six or more or all (such as 6, 7, 8, 9, 10, 11, 12, 13, etc.) 2θ(°) values selected from the groups B1, B2 and B3.

In another preferred embodiment, the X-ray powder diffraction pattern of crystal form B has peaks at 2θ(°) values shown in Table 2 below, and the relative intensities of the respective peaks are shown in Table 2.

TABLE 2

| 2θ(°) | d value [Å] | relative intensity (%) |
|---|---|---|
| 8.27 | 10.69 | S |
| 12.40 | 7.13 | VS |
| 13.28 | 6.66 | S |
| 16.53 | 5.36 | S |

TABLE 2-continued

| 2θ(°) | d value [Å] | relative intensity (%) |
|---|---|---|
| 17.43 | 5.08 | M |
| 18.36 | 4.83 | S |
| 18.68 | 4.75 | S |
| 19.68 | 4.51 | S |
| 20.07 | 4.42 | S |
| 20.73 | 4.28 | S |
| 22.60 | 3.93 | S |
| 24.92 | 3.57 | S |
| 25.35 | 3.51 | S |

In another preferred embodiment, the X-ray powder diffraction pattern of crystal form B is substantially as shown in FIG. 2A.

In another preferred embodiment, the molar ratio of hydrobromic acid to the compound of formula X in crystal form B is (0.8-3.5):1, preferably (1.0-3.0):1.

In another preferred embodiment, the differential scanning calorimetry analysis spectrum of crystal form B is substantially as shown in FIG. 2B.

In another preferred embodiment, the polymorph is C crystalline form of the methanesulfonate of compound of formula X, i.e. crystal form C, which has an X-ray powder diffraction pattern having peaks at the diffraction angle 2θ(°) values of the following group C1: 8.93±0.20, 15.32±0.20, 21.86±0.20, 22.56±0.20, 23.75±0.20, 25.69±0.20, and 27.37±0.20.

In another preferred embodiment, the X-ray diffraction pattern of crystal form C further includes peaks at two or more diffraction angle 2θ(°) values selected from the following group C2: 14.36±0.20, 16.36±0.20, 17.88±0.20, 18.68±0.20, 21.15±0.20, 21.35±0.20, and 28.02±0.20.

In another preferred embodiment, the X-ray diffraction pattern of crystal form C further includes peaks at two or more diffraction angle 2θ(°) values selected from the following group C3: 12.95±0.20, 13.80±0.20, 15.78±0.20, 17.24±0.20, and 19.19±0.20.

In another preferred embodiment, the X-ray diffraction pattern of crystal form C has peaks at six or more or all (such as 6, 7, 8, 9, 10, 11, 12, 13, 14, 15, 16, 17, 18, 19, etc.) 2θ(°) values selected from the groups C1, C2 and C3.

In another preferred embodiment, the X-ray diffraction pattern of crystal form C has peaks at 2θ(°) values shown in Table 3 below, and the relative intensities of the respective peaks are shown in Table 3.

TABLE 3

| 2θ(°) | d value [Å] | relative intensity (%) |
|---|---|---|
| 8.93 | 9.90 | VS |
| 12.95 | 6.83 | M |
| 13.80 | 6.41 | M |
| 14.36 | 6.16 | S |
| 15.32 | 5.78 | VS |
| 15.78 | 5.61 | M |
| 16.36 | 5.42 | S |
| 17.24 | 5.14 | M |
| 17.88 | 4.96 | S |
| 18.68 | 4.75 | S |
| 19.19 | 4.62 | M |
| 21.15 | 4.20 | S |
| 21.35 | 4.16 | S |
| 21.86 | 4.06 | VS |
| 22.56 | 3.94 | VS |
| 23.75 | 3.74 | VS |
| 25.69 | 3.46 | VS |
| 27.37 | 3.26 | VS |
| 28.02 | 3.18 | S |

In another preferred embodiment, the X-ray diffraction pattern of crystal form C is substantially as shown in FIG. 3A.

In another preferred embodiment, the molar ratio of methanesulfonic acid to the compound of formula X in the crystal form C is (0.5-3.5):1, preferably (0.6-3.0):1.

In another preferred embodiment, the differential scanning calorimetry analysis spectrum of crystal form C is substantially as shown in FIG. 3B.

In another preferred embodiment, the polymorph is D crystalline form of the maleate of compound of formula X, i.e. crystal form D, which has an X-ray powder diffraction pattern having peaks at the diffraction angle 2θ(°) values of the following group D1: 5.06±0.20, 8.24±0.20, 10.08±0.20, 15.14±0.20, 16.18±0.20, 18.95±0.20, 19.83±0.20, 20.40±0.20, 21.38±0.20, 22.14±0.20, and 26.51±0.20.

In another preferred embodiment, the X-ray powder diffraction pattern of crystal form D further includes peaks at two or more diffraction angle 2θ(°) values selected from the following group D2: 12.03±0.20, 16.77±0.20, 21.05±0.20, 23.94±0.20, 24.27±0.20, 24.70±0.20, and 30.70±0.20.

In another preferred embodiment, the X-ray powder diffraction pattern of crystal form D further includes peaks at two or more diffraction angle 2θ(°) values selected from the following group D3: 14.24±0.20, 19.33±0.20, 23.46±0.20, 25.10±0.20, 25.53±0.20, 28.09±0.20, 28.40±0.20, 28.85±0.20, 30.23±0.20, 31.15±0.20, 31.48±0.20, 33.57±0.20, and 33.86±0.20.

In another preferred embodiment, the X-ray powder diffraction pattern of crystal form D has peaks at six or more or all (such as 6, 7, 8, 9, 10, 11, 12, 13, 14, 15, etc.) 2θ(°) values selected from the groups D1, D2 and D3. (the relative intensities of the respective peaks are shown in Table 4):

TABLE 4

| 2θ(°) | d value [Å] | relative intensity (%) |
|---|---|---|
| 5.06 | 17.47 | VS |
| 8.24 | 10.72 | VS |
| 10.08 | 8.77 | VS |
| 12.03 | 7.35 | S |
| 14.24 | 6.22 | M |
| 15.14 | 5.85 | VS |
| 16.18 | 5.47 | VS |
| 16.77 | 5.28 | S |
| 18.95 | 4.68 | VS |
| 19.33 | 4.59 | M |
| 19.83 | 4.47 | VS |
| 20.40 | 4.35 | VS |
| 21.05 | 4.22 | S |
| 21.38 | 4.15 | VS |
| 22.14 | 4.01 | VS |
| 23.46 | 3.79 | M |
| 23.94 | 3.71 | S |
| 24.27 | 3.67 | S |
| 24.70 | 3.60 | S |
| 25.10 | 3.55 | M |
| 25.53 | 3.49 | M |
| 26.51 | 3.36 | VS |
| 28.09 | 3.17 | M |
| 28.40 | 3.14 | M |
| 28.85 | 3.09 | M |
| 30.23 | 2.95 | M |

TABLE 4-continued

| 2θ(°) | d value [Å] | relative intensity (%) |
|---|---|---|
| 30.70 | 2.91 | S |
| 31.15 | 2.87 | W |
| 31.48 | 2.84 | W |
| 33.57 | 2.67 | W |
| 33.86 | 2.64 | W |

In another preferred embodiment, the X-ray powder diffraction pattern of crystal form D is substantially as shown in FIG. 4A.

In another preferred embodiment, the molar ratio of maleate to the compound of formula X in crystal form D is (0.6-2):1, preferably (0.7-1.9):1.

In another preferred embodiment, the crystal form D has one or more characteristics selected from the group consisting of:

(1) the differential scanning calorimetry analysis spectrum being substantially as shown in FIG. 4B;

(2) the thermogravimetric analysis spectrum being substantially as shown in FIG. 4C; and (3) the crystal form D having a melting point of 200-210° C., preferably 202-208° C.

In another preferred embodiment, the crystal form D is in an anhydrous form.

In another preferred embodiment, the polymorph is E-1 crystalline form of the sodium salt of compound of formula X, i.e. crystal form E-1, which has an X-ray powder diffraction pattern having a peak at the diffraction angle 2θ(°) value of the following group E-1-1: 4.53±0.20.

In another preferred embodiment, the X-ray powder diffraction pattern of crystal form E-1 further includes peaks at two or more diffraction angle 2θ(°) values selected from the following group E-1-2: 6.52±0.20, 9.18±0.20, and 16.80±0.20.

In another preferred embodiment, the X-ray powder diffraction pattern of crystal form E-1 further includes peaks at two or more diffraction angle 2θ(°) values selected from the following group E-1-3: 8.33±0.20, 10.32±0.20, 18.50±0.20, 19.42±0.20, and 23.86±0.20.

In another preferred embodiment, the X-ray powder diffraction pattern of crystal form E-1 has peaks at six or more or all (such as 6, 7, 8, 9, 10, 11, 12, 13, 14, 15, etc.) 2θ(°) values selected from the groups E-1-1, E-1-2 and E-1-3.

In another preferred embodiment, the X-ray powder diffraction pattern of the crystal form E-1 has peaks at diffraction angle 2θ(°) values shown in Table 5 below, and the relative intensities of the respective peaks are shown in Table 5.

TABLE 5

| 2θ(°) | d value [Å] | relative intensity (%) |
|---|---|---|
| 4.53 | 19.50 | VS |
| 6.52 | 13.55 | S |
| 8.33 | 10.60 | M |
| 9.18 | 9.63 | S |
| 10.32 | 8.57 | M |
| 16.80 | 5.27 | S |
| 18.50 | 4.79 | M |
| 19.42 | 4.57 | M |
| 23.86 | 3.73 | M |

In another preferred embodiment, the X-ray powder diffraction pattern of crystal form E-1 is substantially as shown in FIG. 5A.

In another preferred embodiment, the molar ratio of sodium salt to the compound of formula X in crystal form E-1 is (0.3-3):1, preferably (0.4-2.8):1.

In another preferred embodiment, the differential scanning calorimetry analysis spectrum of crystal form E-1 is substantially as shown in FIG. 5B.

In another preferred embodiment, the polymorph is E-2 crystalline form of the sodium salt of compound of formula X, i.e. crystal form E-2, which has an X-ray powder diffraction pattern having peaks at the diffraction angle 2θ(°) values of the following group E-2-1: 6.90±0.20, 14.44±0.20, 16.96±0.20, 17.77±0.20, 18.42±0.20, 19.72±0.20, 22.22±0.20, 22.67±0.20, and 27.94±0.20.

In another preferred embodiment, the X-ray powder diffraction pattern of crystal form E-2 further includes peaks at two or more diffraction angle 2θ(°) values selected from the following group E-2-2: 11.07±0.20, 19.15±0.20, 23.62±0.20, 24.47±0.20, and 29.76±0.20.

In another preferred embodiment, the X-ray powder diffraction pattern of crystal form E-2 has peaks at six or more or all (such as 6, 7, 8, 9, 10, 11, 12, 13, 14, 15, etc.) diffraction angle 2θ(°) values selected from the groups E-2-1 and E-2-2.

In another preferred embodiment, the X-ray powder diffraction pattern of crystal form E-2 has peaks at diffraction angle 2θ(°) values shown in Table 6 below, and the relative intensities of the respective peaks are shown in Table 6.

TABLE 6

| 2θ(°) | d value [Å] | relative intensity (%) |
|---|---|---|
| 6.90 | 12.79 | VS |
| 11.07 | 7.99 | S |
| 14.44 | 6.13 | VS |
| 16.96 | 5.22 | VS |
| 17.77 | 4.99 | VS |
| 18.42 | 4.81 | VS |
| 19.15 | 4.63 | S |
| 19.72 | 4.50 | VS |
| 22.22 | 4.00 | VS |
| 22.67 | 3.92 | VS |
| 23.62 | 3.76 | S |
| 24.47 | 3.63 | S |
| 27.94 | 3.19 | VS |
| 29.76 | 3.00 | S |

In another preferred embodiment, the X-ray powder diffraction pattern of crystal form E-2 is substantially as shown in FIG. 6A.

In another preferred embodiment, the molar ratio of sodium salt to the compound of formula X in crystal form E-2 is (0.3-3):1, preferably (0.4-2.8):1.

In another preferred embodiment, the differential scanning calorimetry analysis spectrum of crystal form E-2 is substantially as shown in FIG. 6B.

In another preferred embodiment, the polymorph is E-3 crystalline form of the sodium salt of compound of formula X, i.e. crystal form E-3, which has an X-ray powder diffraction pattern having peaks at the diffraction angle 2θ(°) values of the following group E-3-1: 7.12±0.20, 7.57±0.20, 9.94±0.20, 10.71±0.20, and 17.68±0.20.

In another preferred embodiment, the X-ray powder diffraction pattern of crystal form E-3 further includes peaks at two or more diffraction angle 2θ(°) values selected from the following group E-3-2: 6.75±0.20, 14.37±0.20, 17.90±0.20, 18.81±0.20, 19.56±0.20, 20.63±0.20, 21.61±0.20, 22.47±0.20, 23.13±0.20, 23.66±0.20, 24.95±0.20, 25.17±0.20, and 25.39±0.20.

In another preferred embodiment, the X-ray powder diffraction pattern of crystal form E-3 further includes peaks at two or more diffraction angle 2θ(°) values selected from the following group E-3-3: 12.73±0.20, 13.76±0.20, and 19.92±0.20.

In another preferred embodiment, the X-ray powder diffraction pattern of crystal form E-3 has peaks at six or more or all (such as 6, 7, 8, 9, 10, 11, 12, 13, 14, 15, etc.) diffraction angle 2θ(°) values selected from the groups E-3-1, E-3-2 and E-3-3.

In another preferred embodiment, the X-ray powder diffraction pattern of crystal form E-3 has peaks at diffraction angle 2θ(°) values shown in Table 7 below, and the relative intensities of the respective peaks are shown in Table 7.

TABLE 7

| 2θ(°) | d value [Å] | relative intensity (%) |
|---|---|---|
| 6.75 | 13.08 | S |
| 7.12 | 12.41 | VS |
| 7.57 | 11.67 | VS |
| 9.94 | 8.90 | VS |
| 10.71 | 8.25 | VS |
| 12.73 | 6.95 | M |
| 13.76 | 6.43 | M |
| 14.37 | 6.16 | S |
| 17.68 | 5.01 | VS |
| 17.90 | 4.95 | S |
| 18.81 | 4.71 | S |
| 19.56 | 4.54 | S |
| 19.92 | 4.45 | M |
| 20.63 | 4.30 | S |
| 21.61 | 4.11 | S |
| 22.47 | 3.95 | S |
| 23.13 | 3.84 | S |
| 23.66 | 3.76 | S |
| 24.95 | 3.57 | S |
| 25.17 | 3.54 | S |
| 25.39 | 3.51 | S |

In another preferred embodiment, the X-ray powder diffraction pattern of crystal form E-3 is substantially as shown in FIG. 7A.

In another preferred embodiment, the molar ratio of sodium hydroxide to the compound of formula X in crystal form E-3 is (0.3-3):1, preferably (0.4-2.8):1.

In another preferred embodiment, the crystal form E-3 has one or more characteristics selected from the group consisting of:

(1) the differential scanning calorimetry analysis spectrum being substantially as shown in FIG. 7B; and (2) the thermogravimetric analysis spectrum being substantially as shown in FIG. 7C.

In another preferred embodiment, the crystal form E-3 is in a solvate form.

In another preferred embodiment, the crystal is F crystalline form of the potassium salt of compound of formula X, i.e. crystal form F, which has an X-ray powder diffraction pattern having peaks at the diffraction angle 2θ(°) values selected from the following group F-1: 7.83±0.20, 17.68±0.20, and 18.74±0.20.

In another preferred embodiment, the X-ray powder diffraction pattern of crystal form F includes peaks at two or more diffraction angle 2θ(°) values selected from the following group F-2: 6.95±0.20, 9.91±0.20, 12.62±0.20, 14.40±0.20, 16.47±0.20, 20.80±0.20, 21.16±0.20, 22.03±0.20, 23.12±0.20, 23.45±0.20, 24.42±0.20, and 25.15±0.20.

In another preferred embodiment, the X-ray powder diffraction pattern of crystal form F includes peaks at two or more diffraction angle 2θ(°) values selected from the group F-3: 10.73±0.20, 11.65±0.20, 13.61±0.20, 18.21±0.20, 19.97±0.20, 20.47±0.20, 21.51±0.20, 23.99±0.20, 26.69±0.20, 27.38±0.20, 28.27±0.20, 28.83±0.20, 29.67±0.20, and 39.61±0.20.

In another preferred embodiment, the X-ray powder diffraction pattern of crystal form F has peaks at six or more or all (such as 6, 7, 8, 9, 10, 11, 12, 13, 14, 15, etc.) diffraction angle 2θ(°) values selected from the groups F-1, F-2 and F-3.

In another preferred embodiment, the X-ray powder diffraction pattern of crystal form F has peaks at diffraction angle 2θ(°) values shown in Table 8 below, and the relative intensities of the respective peaks are shown in Table 8.

TABLE 8

| 2θ(°) | d value [Å] | relative intensity (%) |
|---|---|---|
| 6.95 | 12.72 | S |
| 7.83 | 11.29 | VS |
| 9.91 | 8.92 | S |
| 10.73 | 8.24 | M |
| 11.65 | 7.59 | W |
| 12.62 | 7.01 | S |
| 13.61 | 6.50 | M |
| 14.40 | 6.14 | S |
| 16.47 | 5.38 | S |
| 17.68 | 5.01 | VS |
| 18.21 | 4.87 | M |
| 18.74 | 4.73 | VS |
| 19.97 | 4.44 | M |
| 20.47 | 4.33 | M |
| 20.80 | 4.27 | S |
| 21.16 | 4.20 | S |
| 21.51 | 4.13 | M |
| 22.03 | 4.03 | S |
| 23.12 | 3.84 | S |
| 23.45 | 3.79 | S |
| 23.99 | 3.71 | M |
| 24.42 | 3.64 | S |
| 25.15 | 3.54 | S |
| 26.69 | 3.34 | M |
| 27.38 | 3.25 | M |
| 28.27 | 3.15 | W |
| 28.83 | 3.09 | M |
| 29.67 | 3.01 | M |
| 39.61 | 2.27 | W |

In another preferred embodiment, the X-ray powder diffraction pattern of crystal form F is substantially as shown in FIG. 8A.

In another preferred embodiment, the crystal form F further has one or more characteristics selected from the group consisting of:

(1) the differential scanning calorimetry analysis spectrum being substantially as shown in FIG. 8B; and (2) the thermogravimetric analysis spectrum being substantially as shown in FIG. 8C.

In another preferred embodiment, the crystal form F is in a solvate form.

In another preferred embodiment, the polymorph is I crystalline form of a free base of the compound of formula X, i.e. crystal form I, which has an X-ray powder diffraction pattern having peaks at the diffraction angle 2θ(°) values of the group I-1: 7.26±0.20, 18.38±0.20, and 23.15±0.20.

In another preferred embodiment, the X-ray powder diffraction pattern of crystal form I includes peaks at two or more diffraction angle 2θ(°) values selected from the group I-2: 9.60±0.20, 14.39±0.20, 15.47±0.20, 22.67±0.20, 25.10±0.20, 29.45±0.20, 30.32±0.20, and 36.79±0.20.

In another preferred embodiment, the X-ray powder diffraction pattern of crystal form I includes peaks at two or more diffraction angle 2θ(°) values selected from the group 1-3: 11.10±0.20, 12.81±0.20, 16.03±0.20, 17.43±0.20, 19.06±0.20, 19.44±0.20, 19.99±0.20, 21.37±0.20, 23.68±0.20, 25.65±0.20, 28.30±0.20, 31.02±0.20, 31.69±0.20, and 37.57±0.20.

In another preferred embodiment, the X-ray powder diffraction pattern of crystal form I has peaks at six or more or all (such as 6, 7, 8, 9, 10, 11, 12, 13, 14, 15, etc.) diffraction angle 2θ(°) values selected from the groups I-1, 1-2 and 1-3.

In another preferred embodiment, the X-ray powder diffraction pattern of crystal form I has peaks at diffraction angle 2θ(°) values shown in Table 9 below, and the relative intensities of the respective peaks are shown in Table 9.

TABLE 9

| 2θ(°) | d value [Å] | relative intensity (%) |
|---|---|---|
| 7.26 | 12.17 | VS |
| 9.60 | 9.21 | S |
| 11.10 | 7.97 | M |
| 12.81 | 6.91 | M |
| 14.39 | 6.15 | S |
| 15.47 | 5.72 | S |
| 16.03 | 5.53 | M |
| 17.43 | 5.09 | W |
| 18.38 | 4.82 | VS |
| 19.06 | 4.65 | W |
| 19.44 | 4.56 | M |
| 19.99 | 4.44 | W |
| 21.37 | 4.15 | M |
| 22.67 | 3.92 | S |
| 23.15 | 3.84 | VS |
| 23.68 | 3.75 | M |
| 25.10 | 3.55 | S |
| 25.65 | 3.47 | W |
| 28.30 | 3.15 | W |
| 29.45 | 3.03 | S |
| 30.32 | 2.95 | S |
| 31.02 | 2.88 | W |
| 31.69 | 2.82 | W |
| 36.79 | 2.44 | S |
| 37.57 | 2.39 | W |

In another preferred embodiment, the X-ray powder diffraction pattern of crystal form I is substantially as shown in FIG. 9A.

In another preferred embodiment, the crystal form I has one or more characteristics selected from the group consisting of:

(1) the differential scanning calorimetry analysis spectrum being substantially as shown in FIG. 9B;

(2) the thermogravimetric analysis spectrum being substantially as shown in FIG. 9C;

(3) the melting point of crystal form I being 175° C. to 185° C., preferably being 178° C. to 185° C.; and (4) the DVS curve is characterized as shown in FIG. 9D.

In another preferred embodiment, the crystal form I is in an anhydrous form.

In another preferred embodiment, the polymorph is II crystalline form of a free base of the compound of formula X, i.e. crystal form II, which has an X-ray powder diffraction pattern having peaks at the diffraction angle 2θ(°) values of the group II-1: 6.84±0.20, 7.74±0.20, and 9.94±0.20.

In another preferred embodiment, the X-ray powder diffraction pattern of crystal form II includes peaks at two or more diffraction angle 2θ(°) values selected from the group 11-2: 7.11±0.20, 17.75±0.20, 18.86±0.20, 19.92±0.20, 23.38±0.20, and 28.63±0.20.

In another preferred embodiment, the X-ray powder diffraction pattern of crystal form II includes peaks at two or more diffraction angle 2θ(°) values selected from the group 11-3: 10.72±0.20, 13.75±0.20, 15.37±0.20, 15.85±0.20, 18.13±0.20, 21.56±0.20, 24.43±0.20, and 27.97±0.20.

In another preferred embodiment, the X-ray powder diffraction pattern of crystal form II has peaks at six or more or all (such as 6, 7, 8, 9, 10, 11, 12, 13, 14, 15, etc.) diffraction angle 2θ(°) values selected from the groups II-1, 11-2 and 11-3.

In another preferred embodiment, the X-ray powder diffraction pattern of crystal form II has peaks at diffraction angle 2θ(°) values shown in Table 10 below, and the relative intensities of the respective peaks are shown in Table 10.

TABLE 10

| 2θ(°) | d value [Å] | relative intensity (%) |
|---|---|---|
| 6.84 | 12.91 | VS |
| 7.11 | 12.42 | S |
| 7.74 | 11.42 | VS |
| 9.94 | 8.89 | VS |
| 10.72 | 8.24 | M |
| 13.75 | 6.44 | M |
| 15.37 | 5.76 | M |
| 15.85 | 5.59 | M |
| 17.75 | 4.99 | S |
| 18.13 | 4.89 | M |
| 18.86 | 4.70 | S |
| 19.92 | 4.45 | S |
| 21.56 | 4.12 | M |
| 23.38 | 3.80 | S |
| 24.43 | 3.64 | W |
| 27.97 | 3.19 | M |
| 28.63 | 3.12 | S |

In another preferred embodiment, the X-ray powder diffraction pattern of crystal form II is substantially as shown in FIG. 10A.

In another preferred embodiment, the crystal form II has one or more characteristics selected from the group consisting of:

(1) the differential scanning calorimetry analysis spectrum being substantially as shown in FIG. 10B; and (2) the DVS curve being substantially as shown in FIG. 10C.

In another preferred embodiment, the polymorph is III crystalline form of a free base of the compound of formula X, i.e. crystal form III, which has an X-ray powder diffraction pattern having a peak at the diffraction angle 2θ(°) value of the group III-1: 4.09±0.20.

In another preferred embodiment, the X-ray powder diffraction pattern of crystal form III includes peaks at two or more diffraction angle 2θ(°) values selected from the group 111-2: 12.22±0.20, 16.34±0.20, 17.83±0.20, and 18.63±0.20.

In another preferred embodiment, the X-ray powder diffraction pattern of crystal form III includes peaks at two or more diffraction angle 2θ(°) values selected from the group 111-3: 13.55±0.20, and 14.46±0.20.

In another preferred embodiment, the X-ray powder diffraction pattern of crystal form III has peaks at six or more or all diffraction angle 2θ(°) values selected from the group III-1, 111-2 and 111-3.

In another preferred embodiment, the X-ray powder diffraction pattern of crystal form III has peaks at diffraction angle 2θ(°) values shown in Table 11 below, and the relative intensities of the respective peaks are shown in Table 11.

TABLE 11

| 2θ(°) | d value [Å] | relative intensity (%) |
|---|---|---|
| 4.09 | 21.57 | VS |
| 12.22 | 7.24 | M |
| 13.55 | 6.53 | W |
| 14.46 | 6.12 | W |
| 16.34 | 5.42 | M |
| 17.83 | 4.97 | M |
| 18.63 | 4.76 | M |

In another preferred embodiment, the X-ray powder diffraction pattern of crystal form III is substantially as shown in FIG. 11A.

In another preferred embodiment, the crystal form III has one or more characteristics selected from the group consisting of:

(1) the differential scanning calorimetry analysis spectrum being substantially as shown in FIG. 11B;

(2) the thermogravimetric analysis spectrum being substantially as shown in FIG. 11C; and (3) the DVS curve being characterized as shown in FIG. 11D.

In another preferred embodiment, the crystal form III is in an anhydrous form.

In another preferred embodiment, the polymorph is IV crystalline form of a free base of the compound of formula X, i.e. crystal form IV, which has an X-ray powder diffraction pattern having a peak at the diffraction angle 2θ(°) value of the group IV-1: 4.66±0.20.

In another preferred embodiment, the X-ray powder diffraction pattern of crystal form IV includes peaks at two or more diffraction angle 2θ(°) values selected from the group IV-2: 5.28±0.20, 9.29±0.20, 16.49±0.20, 16.87±0.20, 17.56±0.20, 19.19±0.20, and 23.89±0.20.

In another preferred embodiment, the X-ray powder diffraction pattern of crystal form IV includes peaks at two or more diffraction angle 2θ(°) values selected from the group IV-3: 6.62±0.20, and 8.46±0.20.

In another preferred embodiment, the X-ray powder diffraction pattern of crystal form IV has peaks at six or more or all (such as 6, 7, 8, 9, 10, 11, 12, 13, 14, 15, etc.) diffraction angle 2θ(°) values of the groups IV-1, IV-2 and IV-3.

In another preferred embodiment, the X-ray powder diffraction pattern of crystal form IV has peaks at diffraction angle 2θ(°) values shown in Table 12 below, and the relative intensities of the respective peaks are shown in Table 12.

TABLE 12

| 2θ(°) | d value [Å] | relative intensity (%) |
|---|---|---|
| 4.66 | 18.95 | VS |
| 5.28 | 16.72 | S |
| 6.62 | 13.34 | M |
| 8.46 | 10.45 | M |
| 9.29 | 9.52 | S |
| 16.49 | 5.37 | S |
| 16.87 | 5.25 | S |
| 17.56 | 5.05 | S |
| 19.19 | 4.62 | S |
| 23.89 | 3.72 | S |

In another preferred embodiment, the X-ray powder diffraction pattern of crystal form IV is substantially as shown in FIG. 12A.

In another preferred embodiment, the crystal form IV has one or more characteristics selected from the group consisting of:

(1) the differential scanning calorimetry analysis spectrum being substantially as shown in FIG. 12B;

(2) the thermogravimetric analysis spectrum being substantially as shown in FIG. 12C; and (3) the DVS curve being characterized as shown in FIG. 12D.

In another preferred embodiment, the crystal form IV is in a solvate form.

In another preferred embodiment, the polymorph is V crystalline form of a free base of the compound of formula X, i.e. crystal form V, which has an X-ray powder diffraction pattern having peaks at the diffraction angle 2θ(°) values of the group V-1: 6.79±0.20, 14.31±0.20, 16.90±0.20, 17.58±0.20, 20.58±0.20, 21.90±0.20, and 23.45±0.20.

In another preferred embodiment, the X-ray powder diffraction pattern of crystal form V includes peaks at two or more diffraction angle 2θ(°) values selected from the group V-2: 13.67±0.20, 15.15±0.20, 16.35±0.20, 18.45±0.20, 20.96±0.20, 25.15±0.20, 28.19±0.20, and 29.19±0.20.

In another preferred embodiment, the X-ray powder diffraction pattern of crystal form V has peaks at six or more or all (such as 6, 7, 8, 9, 10, 11, 12, 13, 14, 15, etc.) diffraction angle 2θ(°) values selected from the groups V-1 and V-2.

In another preferred embodiment, the X-ray powder diffraction pattern of crystal form V has peaks at diffraction angle 2θ(°) values shown in Table 13 below, and the relative intensities of the respective peaks are shown in Table 13.

TABLE 13

| 2θ(°) | d value [Å] | relative intensity (%) |
|---|---|---|
| 6.79 | 13.02 | VS |
| 13.67 | 6.47 | S |
| 14.31 | 6.19 | VS |
| 15.15 | 5.84 | S |
| 16.35 | 5.42 | S |
| 16.90 | 5.24 | VS |
| 17.58 | 5.04 | VS |
| 18.45 | 4.81 | S |
| 20.58 | 4.31 | VS |
| 20.96 | 4.23 | S |
| 21.90 | 4.05 | VS |
| 23.45 | 3.79 | VS |
| 25.15 | 3.54 | S |
| 28.19 | 3.16 | S |
| 29.19 | 3.06 | S |

In another preferred embodiment, the X-ray powder diffraction pattern of crystal form V is substantially as shown in FIG. 13A.

In another preferred embodiment, the crystal form V has one or more characteristics selected from the group consisting of:

(1) the differential scanning calorimetry analysis spectrum being substantially as shown in FIG. 13B;

(2) the thermogravimetric analysis spectrum being substantially as shown in FIG. 13C; and (3) the DVS curve being characterized as shown in FIG. 13D.

In another preferred embodiment, the crystal form V is in a solvate form.

In another preferred embodiment, the polymorph is VI crystalline form of a free base of the compound of formula X, i.e. crystal form VI, which has an X-ray powder diffraction pattern having peaks at the diffraction angle 2θ(°) values of the group VI-1: 6.90±0.20, 7.14±0.20, 16.40±0.20, 16.92±0.20, 20.62±0.20, and 23.52±0.20.

In another preferred embodiment, the X-ray powder diffraction pattern of crystal form VI includes peaks at two or more diffraction angle 2θ(°) values selected from the group VI-2: 13.76±0.20, 14.26±0.20, 18.21±0.20, 18.46±0.20, 21.92±0.20, 25.13±0.20, and 29.19±0.20.

In another preferred embodiment, the X-ray powder diffraction pattern of crystal form VI includes peaks at two or more diffraction angle 2θ(°) values selected from the group VI-3: 17.65±0.20, 21.01±0.20, 22.55±0.20, 23.03±0.20, and 26.31±0.20.

In another preferred embodiment, the X-ray powder diffraction pattern of crystal form VI has peaks at six or more or all (such as 6, 7, 8, 9, 10, 11, 12, 13, 14, 15, etc.) diffraction angle 2θ(°) values selected from the groups VI-1, VI-2 and VI-3.

In another preferred embodiment, the X-ray powder diffraction pattern of crystal form VI has peaks at diffraction angle 2θ(°) values shown in Table 14 below, and the relative intensities of the respective peaks are shown in Table 14.

TABLE 14

| 2θ(°) | d value [Å] | relative intensity (%) |
| --- | --- | --- |
| 6.90 | 12.79 | VS |
| 7.14 | 12.37 | VS |
| 13.76 | 6.43 | S |
| 14.26 | 6.21 | S |
| 16.40 | 5.40 | VS |
| 16.92 | 5.24 | VS |
| 17.65 | 5.02 | M |
| 18.21 | 4.87 | S |
| 18.46 | 4.80 | S |
| 20.62 | 4.30 | VS |
| 21.01 | 4.23 | M |
| 21.92 | 4.05 | S |
| 22.55 | 3.94 | M |
| 23.03 | 3.86 | M |
| 23.52 | 3.78 | VS |
| 25.13 | 3.54 | S |
| 26.31 | 3.38 | M |
| 29.19 | 3.06 | S |

In another preferred embodiment, the X-ray powder diffraction pattern of crystal form VI is substantially as shown in FIG. 14A.

In another preferred embodiment, the crystal form VI has one or more characteristics selected from the group consisting of:

(1) the differential scanning calorimetry analysis spectrum being substantially as shown in FIG. 14B;

(2) the thermogravimetric analysis spectrum being substantially as shown in FIG. 14C; and (3) the DVS curve being characterized as shown in FIG. 14D.

In another preferred embodiment, the crystal form VI is in an anhydrous form.

In another preferred embodiment, the polymorph is VII crystalline form of a free base of the compound of formula X, i.e. crystal form VII, which has an X-ray powder diffraction pattern having peaks at the diffraction angle 2θ(°) values of the group VII-1: 7.11±0.20, and 14.22±0.20.

In another preferred embodiment, the X-ray powder diffraction pattern of crystal form VII includes peaks at two or more diffraction angle 2θ(°) values selected from the group VII-2: 18.16±0.20, 21.29±0.20, 29.25±0.20, 31.53±0.20, and 36.50±0.20.

In another preferred embodiment, the X-ray powder diffraction pattern of crystal form VII includes peaks at two or more diffraction angle 2θ(°) values selected from the group VII-3: 23.02±0.20, 30.09±0.20, and 37.46±0.20.

In another preferred embodiment, the X-ray powder diffraction pattern of crystal form VII has peaks at six or more or all (such as 6, 7, 8, 9, 10, 11, 12, 13, 14, 15, etc.) diffraction angle 2θ(°) values selected from the groups VII-1, VII-2 and VII-3.

In another preferred embodiment, the X-ray powder diffraction pattern of crystal form VII has peaks at diffraction angle 2θ(°) values shown in Table 15 below, and the relative intensities of the respective peaks are shown in Table 15.

TABLE 15

| 2θ(°) | d value [Å] | relative intensity (%) |
| --- | --- | --- |
| 7.11 | 12.42 | VS |
| 14.22 | 6.22 | VS |
| 18.16 | 4.88 | M |
| 21.29 | 4.17 | M |
| 23.02 | 3.86 | W |
| 29.25 | 3.05 | M |
| 30.09 | 2.97 | W |
| 31.53 | 2.84 | M |
| 36.50 | 2.46 | M |
| 37.46 | 2.40 | W |

In another preferred embodiment, the X-ray powder diffraction pattern of crystal form VII is substantially as shown in FIG. 15A.

In another preferred embodiment, the crystal form VII has one or more characteristics selected from the group consisting of:

(1) the differential scanning calorimetry analysis spectrum being substantially as shown in FIG. 15B;

(2) the thermogravimetric analysis spectrum being substantially as shown in FIG. 15C; and (3) the DVS curve being characterized as shown in FIG. 15D.

In another preferred embodiment, the crystal form VII is in an anhydrous form.

In the second aspect of the present disclosure, a process for preparing the compound of formula X or its pharmaceutically acceptable salt of the first aspect of the present disclosure is provided, and the process includes the following steps:

(1) reacting compound X-4 with compound X-a under alkaline conditions to form the compound of formula X;

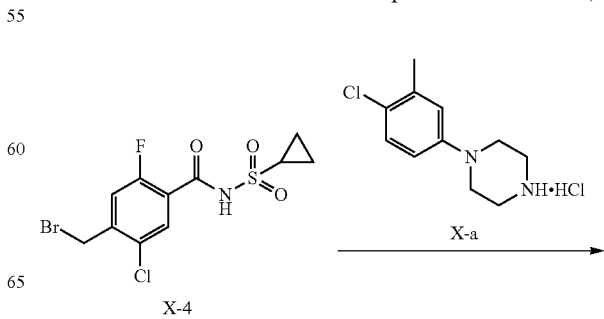

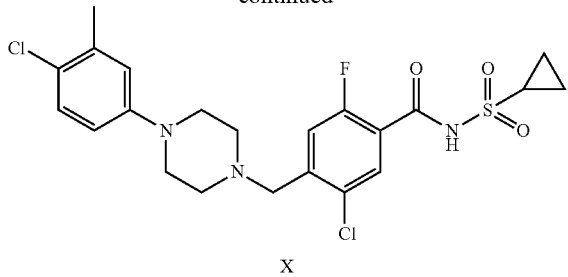

X (2) optionally, reacting the compound of formula X with an acid or base to form a pharmaceutically acceptable salt; and (3) optionally, performing crystallization processing on the compound of formula X, or the pharmaceutically acceptable salt thereof formed in step (1) or (2) to obtain a crystal.

In another preferred embodiment, the process includes any of the following sub-processes (A)-(E) and (I), (II).

(A) the crystal is A crystalline form of the hydrochloride of the compound of formula X, i.e. crystal form A, and the step (3) includes crystallization processing the compound of formula X in an organic solvent in the presence of hydrochloric acid to form the crystal form A.

In another preferred embodiment, in sub-process (A), the organic solvent is selected from the group consisting of methanol, ethyl acetate, acetone, acetonitrile and mixtures thereof; preferably, the organic solvent is methanol.

In another preferred embodiment, in sub-process (A), the molar ratio of hydrochloric acid to the compound of formula X is (0.5-2):1, preferably (0.5-1.5):1.

In another preferred embodiment, in sub-process (A), the crystallization processing is slowly cooling.

In another preferred embodiment, in sub-process (A), the crystallization processing temperature is 0-60° C., preferably is 40-60° C.

In another preferred embodiment, in sub-process (A), the crystallization processing time is 1-48 hours, preferably is 2-40 hours.

(B) the crystal is B crystalline form of the hydrobromide of the compound of formula X, i.e. crystal form B, and the step (3) comprises crystallization processing the compound of formula X in an organic solvent in the presence of hydrobromic acid to form the crystal form B.

In another preferred embodiment, in sub-process (B), the organic solvent is selected from the group consisting of methanol, ethyl acetate, acetone, acetonitrile and mixtures thereof, preferably, the organic solvent is ethyl acetate.

In another preferred embodiment, in sub-process (B), the molar ratio of hydrobromic acid to the compound of formula X is (0.8-3.5):1, preferably is (1.0-3.0):1.

In another preferred embodiment, in sub-process (B), the crystallization processing is slowly cooling.

In another preferred embodiment, in sub-process (B), the crystallization processing temperature is 0-60° C., preferably is 40-60° C.

In another preferred embodiment, in sub-process (B), the crystallization processing time is 1-48 hours, preferably is 2-40 hours.

(C) the crystal is C crystalline form of the methanesulfonate of the compound of formula X, i.e. crystal form C, and the step (3) comprises crystallization processing the compound of formula X in an organic solvent in the presence of methanesulfonic acid to form the crystal form C.

In another preferred embodiment, in sub-process (C), the organic solvent is methanol, ethyl acetate, acetone, acetonitrile or mixtures thereof, preferably, the organic solvent is ethyl acetate.

In another preferred embodiment, in sub-process (C), the molar ratio of methanesulfonic acid to the compound of formula X is (0.5-3.5):1, preferably (0.6-3.0):1.

In another preferred embodiment, in sub-process (C), the crystallization processing is slowly cooling, adding anti-solvent or a combination thereof.

In another preferred embodiment, in sub-process (C), the crystallization processing temperature is 0-60° C., preferably is 40-60° C.

In another preferred embodiment, in sub-process (C), the crystallization processing time is 1-48 hours, preferably is 2-40 hours.

(D) the crystal is D crystalline form of the maleate of the compound of formula X, i.e. crystal form D, and the step (3) includes crystallization processing the compound of formula X in an organic solvent in the presence of maleic acid to form the crystal form D.

In another preferred embodiment, in sub-process (D), the organic solvent is selected from the group consisting of methanol, ethyl acetate, acetone, acetonitrile and mixtures thereof, preferably, the organic solvent is acetone.

In another preferred embodiment, in sub-process (D), the molar ratio of maleic acid to the compound of formula X is (0.6-2):1, preferably (0.7-1.9):1.

In another preferred embodiment, in sub-process (D), the crystallization processing is slowly cooling, anti-solvent adding or a combination thereof.

In another preferred embodiment, in sub-process (D), the crystallization processing temperature is 0-60° C., preferably is 40-60° C.

In another preferred embodiment, in sub-process (D), the crystallization processing time is 1-48 hours, preferably is 2-40 hours.

(E) the crystal is E-1 crystalline form of the sodium hydroxide salt of the compound of formula X, i.e. crystal form E-1, and the step (3) includes crystallization processing the compound of formula X in an organic solvent in the presence of sodium hydroxide to form the crystal form E-1.

In another preferred embodiment, in sub-process (E), the organic solvent is selected from the group consisting of methanol, ethyl acetate, acetone, acetonitrile and mixtures thereof, preferably, the organic solvent is acetonitrile.

In another preferred embodiment, in sub-process (E), the molar ratio of sodium hydroxide to the compound of formula X is (0.3-3):1, preferably (0.4-2.8):1.

In another preferred embodiment, in sub-process (E), the crystallization processing is slowly cooling, anti-solvent adding, slowly volatilizing or a combination thereof.

In another preferred embodiment, in sub-process (E), the crystallization processing temperature is 0-60° C., preferably is 40-60° C.

In another preferred embodiment, in sub-process (E), the crystallization processing time is 1-48 hours, preferably is 2-40 hours.

(F) the crystal is E-2 crystalline form of the sodium hydroxide salt of the compound of formula X, i.e. crystal form E-2, and the step (3) includes crystallization processing the compound of formula X in an organic solvent in the presence of sodium hydroxide to form the crystal form E-2.

In another preferred embodiment, in sub-process (F), the organic solvent is selected from the group consisting of methanol, ethyl acetate, acetone, acetonitrile and mixtures thereof, preferably, the organic solvent is ethyl acetate.

In another preferred embodiment, in sub-process (F), the molar ratio of sodium hydroxide to the compound of formula X is (0.3-3):1, preferably (0.4-2.8):1.

In another preferred embodiment, in sub-process (F), the crystallization processing is slowly cooling, anti-solvent adding or a combination thereof.

In another preferred embodiment, in sub-process (F), the crystallization processing temperature is 0-60° C., preferably is 40-60° C.

In another preferred embodiment, in sub-process (F), the crystallization processing time is 1-48 hours, preferably is 2-40 hours.

(G) the crystal is E-3 crystalline form of the sodium hydroxide salt of the compound of formula X, i.e. crystal form E-3, and the step (3) includes crystallization processing the compound of formula X in an organic solvent in the presence of sodium hydroxide to form the crystal form E-3.

In another preferred embodiment, in sub-process (G), the organic solvent is selected from the group consisting of methanol, ethyl acetate, acetone, acetonitrile and mixtures thereof, preferably, the organic solvent is acetonitrile.

In another preferred embodiment, in sub-process (G), the molar ratio of sodium hydroxide to the compound of formula X is (0.3-3):1, preferably (0.4-2.8):1.

In another preferred embodiment, in sub-process (G), the crystallization processing is slowly cooling, anti-solvent adding, slow volatilizing or a combination thereof.

In another preferred embodiment, in sub-process (G), the crystallization processing temperature is 0-60° C., preferably is 40-60° C.

In another preferred embodiment, in sub-process (G), the crystallization processing time is 1-48 hours, preferably is 2-40 hours.

(H) the crystal is F crystalline form of the potassium salt of the compound of formula X, i.e. crystal form F, and the step (3) includes crystallization processing the compound of formula X in an organic solvent in the presence of potassium hydroxide to form the crystal form F.

In another preferred embodiment, in sub-process (H), the organic solvent is selected from the group consisting of methanol, ethyl acetate, acetone, acetonitrile and mixtures thereof, preferably, the organic solvent is methanol.

In another preferred embodiment, in sub-process (H), the molar ratio of potassium hydroxide to the compound of formula X is (0.5-3.5):1, preferably (0.6-3.3):1.

In another preferred embodiment, in sub-process (H), the crystallization processing is slowly cooling, anti-solvent adding or a combination thereof.

In another preferred embodiment, in sub-process (H), the crystallization processing temperature is 0-60° C., preferably is 40-60° C.

In another preferred embodiment, in sub-process (H), the crystallization processing time is 1-48 hours, preferably is 2-40 hours.

(I) the crystal is I crystalline form of the compound of formula X, i.e. crystal form I, and the step (3) includes crystallization processing the compound of formula X in an organic solvent to form the crystal form I.

In another preferred embodiment, in sub-process (I), the crystallization processing is slowly volatilizing, slowly cooling, anti-solvent adding, suspension stirring or a combination thereof, wherein slowly volatilizing and slowly cooling are preferred.

In another preferred embodiment, in sub-process (I), the crystallization processing is slowly volatilizing, the organic solvent is selected from the group consisting of acetone, acetonitrile, ethyl acetate and mixtures thereof.

In another preferred embodiment, in sub-process (I), the crystallization processing is slowly cooling, the organic solvent is selected from the group consisting of methanol, ethanol, acetone, acetonitrile, ethyl acetate and mixtures thereof.

In another preferred embodiment, in sub-process (I), the crystallization processing is anti-solvent adding, the organic solvent is selected from the group consisting of a combination of dimethylacetamide and water, and a combination of ethyl acetate and n-heptane.

In another preferred embodiment, in sub-process (I), the crystallization processing is suspension stirring, the organic solvent is selected from the group consisting of methanol, ethanol, isopropanol, acetone, acetonitrile, ethyl acetate, water, methyl tert-butyl ether and mixtures thereof.

(M) the crystal is V crystalline form of a free base of the compound of formula X, i.e. crystal form V, and the step (3) includes crystallization processing the compound of formula X in an organic solvent to form the crystal form V.

In another preferred embodiment, in sub-process (M), the crystallization processing is slowly volatilizing, the organic solvent is selected from tetrahydrofuran.

(N) the crystal is VI crystalline form of a free base of the compound of formula X, i.e. crystal form VI, and the step (3) includes crystallization processing the compound of formula X in an organic solvent to form the crystal form VI.

In another preferred embodiment, in sub-process (N), the crystallization processing is anti-solvent adding, the organic solvent is selected from acetone and water.

(O) the crystal is VII crystalline form of a free base of the compound of formula X, i.e. crystal form VII, and the step (3) includes crystallization processing the compound of formula X in an organic solvent to form the crystal form VII.

In another preferred embodiment, in sub-process (O), the crystallization processing is anti-solvent adding, the organic solvent is selected from methanol and water.

In the third aspect of the disclosure, a pharmaceutical composition is provided. The pharmaceutical composition includes: (a) the compound of formula X, or a pharmaceutically acceptable salt thereof, or a polymorph thereof according to any one of the first aspect of the disclosure; and (b) a pharmaceutically acceptable carrier.

In the fourth aspect of the present disclosure, a use of any one of the formula X compound of the first aspect of the disclosure, or a pharmaceutically acceptable salt thereof, or a polymorph thereof, or a pharmaceutical composition of the third aspect of the disclosure in the preparation of a medicament for the treatment of a pain, depression, cardiovascular disease, respiratory disease or mental illness is provided.

It should be understood that each of the above technical features of the disclosure and each technical feature specifically described below (such as in the Examples) can be combined with each other within the scope of the present disclosure so as to constitute new or preferred technical solutions which need not be specified again herein.

DETAILED DESCRIPTION OF THE EMBODIMENTS

Figure 1A:
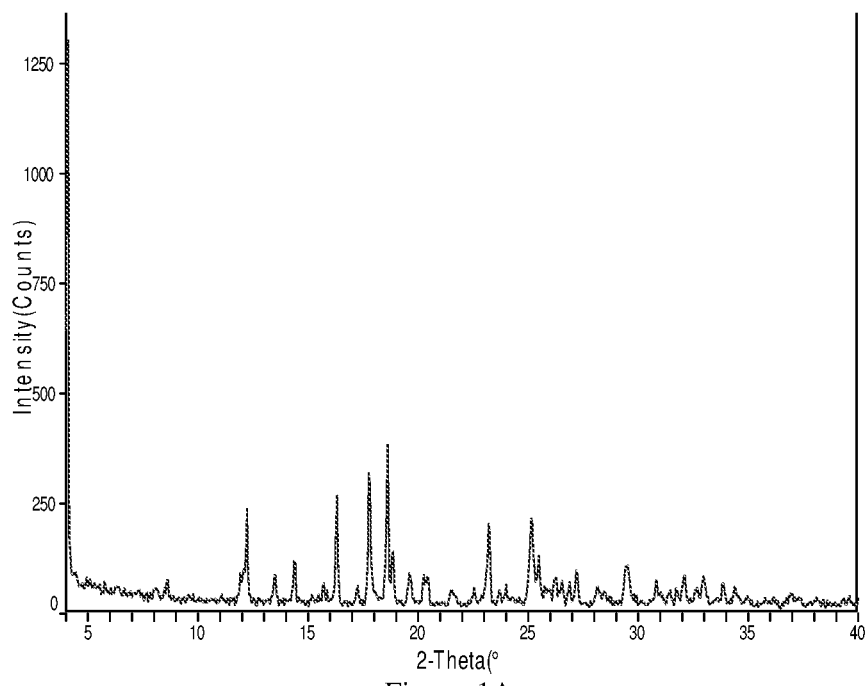
FIG. 1A is the X-ray powder diffraction pattern of crystal form A.

As used herein, the term "compound of the present disclosure" includes the compound of formula X of the present disclosure, a pharmaceutically acceptable salt of the compound of formula X of the present disclosure, and the polymorph of the present disclosure.

Compound of Formula X

In the present disclosure, "compound of formula X" or "compound shown in formula X" can be used interchangeably; unless otherwise specified, it generally refers to a free base form.

In the present disclosure, the compound of formula X is 5-chloro-4-((4-(4-chloro-3-methylphenyl)piperazin-1-yl)methyl)-N-(cyclopropylsulfonyl)-2-fluorobenzamide.

In the present disclosure, "free base sample" or "free base" refers to a free base of the compound of formula X prepared in Example 1.

Pharmaceutically Acceptable Salt of the Compound of Formula X

In the present disclosure, the pharmaceutically acceptable salts are preferably selected from the group consisting of hydrochloride, sulfate, phosphate, acetate, L-lactate, maleate, fumarate, succinate, L-malate, adipate, L-tartrate, hippurate, citrate, mucate, glycollate, D-glucuronate, benzoate, gentisate, nicotinate, ethanedisulphonate, oxalate, methanesulfonate, benzenesulfonate, 2-hydroxyethane sulfonate and hydrobromide.

Polymorphs

Solid exists in amorphous form or in crystalline form. In the case of crystal form, the molecules are positioned in the three-dimensional lattice sites. When a compound is crystallized from a solution or slurry, it can be crystallized in different space lattice arrangement (this property is called "polymorphism") to form crystals with different crystalline forms, and all those crystalline forms are called as "polymorphs". Different polymorphs of a given substance may differ from each other in one or more physical properties (such as solubility and dissolution rate, true specific gravity, crystalline form, packing pattern, flowability and/or solid state stability).

Crystallization

Crystallization on a production scale can be accomplished by manipulating a solution such that the solubility limit of the interested compound is exceeded. This can be done in a variety of ways, for example, slowly cooling, that is, dissolving the compound at a relatively high temperature and then cooling the solution to below a saturation limit, or reducing the liquid volume by boiling, evaporating at ordinary pressure, drying under vacuum or by some other means. The solubility of the interested compound may be reduced by adding an anti-solvent or a solvent in which the compound has a low solubility or a mixture of such solvents. An alternative method is to adjust the pH to reduce the solubility. See Crystallization, Third Edition, J W MullFns, ButtFrworth-HFinFman Ltd., 1993, ISBN 0750611294 for a detailed description of crystallization.

The "suspension stirring" described in the present disclosure means a way to get crystals by mixing the compound of formula X with a corresponding acid or a solution of the corresponding acid in a suitable solvent to form a turbid solution, or by mixing the compound of formula X with a suitable solvent to form a turbid solution before stirring. Suitable solvents may be water or organic solvents.

The "slowly volatilizing" described in the present disclosure means a way to get crystals by placing a solution of the compound of formula X or a solution of the compound of formula X and the corresponding acid at a certain temperature for slowly volatilizing the solvent.

The "anti-solvent adding" described in the present disclosure means a way to get crystals by, to a solution of the compound of formula X, adding a different, suitable solvent, for precipitating the crystals.

If salt formation and crystallization are expected to occur at the same time, the addition of an appropriate acid or base can result in the direct crystallization of the desired salt if the salt is less soluble in the reaction medium than in the raw material. Likewise, in a medium in which the desired final form has a solubility lower than that of reactants, the final product can be directly crystallized when the synthetic reaction is completed.

Optimization of crystallization can include inoculation of the crystal of desired form as a seed into the crystallization medium. In addition, many crystallization methods include a combination of the above strategies. One example is to dissolve the interested compound in a solvent at a high temperature, followed by the addition of an antisolvent with a suitable volume in a controlled manner so that the system is just below the saturation level. At this moment, the seed of desired form (the integrity of the seed is kept) can be added and the system is cooled to accomplish the crystallization.

As used herein, the term "room temperature" generally means 4-30° C., preferably 20±5° C.

Polymorphs of the Present Disclosure

In the present disclosure, "crystal(s) of the present disclosure", "crystalline form of the present disclosure", "polymorph(s) of the present disclosure" and the like can be used interchangeably.

In the present disclosure, "polymorph of the compound of formula X" and "polymorph of a free base of the compound of formula X" are used interchangeably.

As used herein, the term "polymorph of the present disclosure" includes polymorphs of a free base of the compound of formula X or polymorphs of pharmaceutically acceptable salts of the compound of formula X (e.g. hydrochloride, sulfate, hydrobromide, phosphate, methanesulfonate, maleate, L-tartrate, citrate, fumarate), or polymorphs of various solvates of the compound of formula X, and also include different polymorphs of the same salts (such as hydrochloride, sulfate, hydrobromide, phosphate, methanesulfonate, maleate, L-tartrate, citrate, fumarate) or solvates.

Preferred polymorphs of the present disclosure include (but not limited to): (i) crystal form A, crystal form B, crystal form C, crystal form D, crystal form E-1, crystal form E-2, crystal form E-3, crystal form F (crystal form of salt); and (ii) crystal form I, crystal form II, crystal form III, crystal form IV, crystal form V, crystal form VI, crystal form VII (crystal form of the compound of formula X).

Identification and Properties of Polymorphs

Polymorphs of the compounds of formula X or the pharmaceutically acceptable salts can be characterized using known methods or instruments, for example, using a variety of means and instruments as follows.

X-Ray Powder Diffraction

Methods of determining X-ray powder diffraction of the crystals are known in the art. For example, an X-ray powder diffractometer can be used to obtain a pattern with a copper radiation target at a scanning speed of 2° per minute.

The polymorph of the compound of formula X of the present disclosure or a pharmaceutically acceptable salt thereof has a specific crystalline form and has specific characteristic peaks in an X-ray powder diffraction (XRPD) pattern.

Differential Scanning Calorimetry

It is also called "differential scanning calorimetry analysis" (DSC) which is a technique that measures the relationship between energy difference of the measured substance and the reference substance and temperature during heating. The location, shape and number of peaks on the DSC pattern are related to the nature of the substance, and therefore can be used to qualitatively identify the substance. This method can be commonly used in the art to detect the phase transition temperature, glass transition temperature, reaction heat and other parameters of a substance.

Pharmaceutical Compositions of Compound of Formula X and their Use

Generally, the compound of formula X of the present disclosure or a pharmaceutically acceptable salt thereof may form a suitable dosage form for administration with one or more pharmaceutically acceptable carriers. These dosage forms are adapted for oral, rectal, topical, intraoral administration, and other parenteral administrations (e.g., subcutaneous, intramuscular, intravenous administration, etc.). For example, dosage forms adapted for oral administration include capsules, tablets, granules and syrups. Compounds of the present disclosure contained in these formulations may be: solid powders or granules; aqueous or non-aqueous solutions or suspensions; water-in-oil or oil-in-water emulsions; etc. Such dosage forms may be prepared with active compounds and one or more carriers or excipients through conventional pharmacy methods. The above-mentioned carriers should be compatible with active compounds or other excipients. For solid formulations, conventional non-toxic carriers include, but not limited to, mannitol, lactose, starch, magnesium stearate, cellulose, glucose, sucrose and the like. Carriers for liquid preparations include water, saline, aqueous dextrose, ethylene glycol and polyethylene glycol. The active compounds may form a solution or suspension with the above-mentioned carriers.

The compositions of the present disclosure are formulated, quantified and administered in a manner consistent with the practice of medicine. The "effective amount" of the administered compound depends on factors such as the specific disease to be treated, the individual being treated, the cause of a disease, the drug targets and the mode of administration, etc.

As used herein, "therapeutically effective amount" refers to the amount that yields a function or activity to humans and/or animals and can be tolerated by humans and/or animals.

The therapeutically effective amount of the compound of the present disclosure contained in the pharmaceutical composition or medicinal composition of the present disclosure is preferably 0.1 mg-5 g/kg body weight.

The compound of the disclosure or the pharmaceutical compositions of the disclosure are useful in the treatment of pain, depression, cardiovascular disease, respiratory disease or mental illness.

In another preferred example, the disease or disorder is selected from the group consisting of: HIV-related pain; HIV treatment-induced neuropathy; prosopalgia; post-herpetic neuralgia; acute pain; heat-sensitivity; sarcoidosis; irritable bowel syndrome; Crohn's disease; pain associated with multiple sclerosis (MS); amyotrophic lateral sclerosis (ALS); diabetic neuropathy; peripheral neuropathy; arthritis; rheumatoid arthritis; osteoarthritis; atherosclerosis; sudden dystonia; myasthenia syndrome; myotonia; hyperpyrexia; cystic fibrosis; pseudogalonism; rhabdomyolysis; hypothyroidism; bipolar depression; anxiety; schizophrenia; sodium channel toxins related disorders; familial erythromelalgia; primary erythromelalgia; familial rectal pain; cancers; epilepsy; partial and generalized tonic attacks; restless legs syndrome; arrhythmia; fibromyalgia; neuroprotection, tachyarrhythmia, atrial fibrillation and ventricular fibrillation in ischemic disease conditions caused by stroke or nerve injury; neuropathic pain; inflammatory pain; visceral pain; cancer pain; chemotherapeutic pain; traumatic pain; surgical pain; postoperative pain; production pain; labor pain; toothache; chronic pain; persistent pain; peripherally mediated pain; centrally mediated pain; chronic headache; migraine; sinus headache; tension headache; phantom limb pain; peripheral nerve injury; prosopalgia; postherpetic neuralgia; acute pain; familial erythromelalgia; primary erythromelagia; familial rectal pain and fibromyalgia.

The compound of the disclosure or the pharmaceutical compositions of the disclosure may be used in combination with other drugs in certain diseases to achieve a desired therapeutic effect.

The main advantages of the present disclosure include high selectivity of the compound of the disclosure for Nav1.7 sodium ion channel with respect to Nav1.5, Nav1.8, Cav3.2 and hERG potassium ion channels, and stable liver microsomes metabolic stability.

The present disclosure will be further illustrated below with reference to the specific examples. It should be understood that these examples are only to illustrate the disclosure but not to limit the disclosure of the disclosure. The experimental methods without specific conditions in the following embodiments are generally carried out according to conventional conditions, or in accordance with the conditions recommended by the manufacturer. Unless indicated otherwise, parts and percentage are calculated by weight.

Reagents and Instruments

The structure and purity of the compounds are identified by nuclear magnetic resonance ($^1$HNMR) and/or liquid chromatography-mass spectrometry (LC-MS). $^1$HNMR: BrukerAVANCF-400 NMR machine, the internal standard was tetramethylsilane (TMS). LC-MS: Agilent 1200 HPLC System/6140 MS liquid-mass spectrometer (available from Agilent), column WatersX-Bridge, 150×4.6 mm, 3.5 μm.

Preparative high performance liquid chromatography (pre-HPLC): Waters PHW007, column XBridge C18, 4.6*150 mm, 3.5 μm.

ISCO Combiflash-Rf75 or Rf200 automatic eluting column instrument, Agela 4 g, 12 g, 20 g, 40 g, 80 g, 120 g disposable silica gel column.

The starting materials may be synthesized by using the methods known in the art, or may be purchased from ABCR GmbH & Co. KG, Acros Organics, Aldrich Chemical Company, Accela ChemBio Inc and Darui Chemical Company etc.

All examples were performed under nitrogen or argon atmosphere and the solution refers to the aqueous solution if without special explanation.

As used herein, DMF refers to dimethylformamide, DMSO refers to dimethylsulfoxide, THF refers to tetrahydrofuran, DIEA refers to N,N-diisopropylethylamine, EA or EtOAc refers to ethyl acetate, PE refers to petroleum ether, DCDMH refers to 1,3-dichloro-5,5-dimethylhydantoin, EDC.HCl refers to 1-ethyl-(3-dimethylaminopropyl)carbamoimide hydrochloride, ACN refers to acetonitrile, MeOH refers to methanol, EtOH refers to ethanol, IPA refers to isopropanol, Actone refers to acetone, MTBE refers to methyl tert-butyl ether, and THF refers to tetrahydrofuran.

General Method

The powder X-ray diffraction patterns are obtained using a D8 ADVANCE X-ray powder diffraction analyzer through methods known in the art. XRPD test parameters are shown in the following table 16.

TABLE 16

| Parameter | XRPD |
| --- | --- |
| X-ray source | Cu K (λ = 1.54056 Angstrom) |
| tube settings | 40 kV, 40 mA |
| Detector | PSD |
| Scanning range (2θ (°)) | 4°-40° |
| Scanning step (2θ (°)) | 0.05 |
| Scanning rate | 1 second/step |

In the pattern, the site of each peak was determined by 2θ)(°. It should be understood that different instruments and/or conditions could result in slightly different data and changes in peak site and relative intensity. The division of the intensity of peaks only reflects the approximate size of peaks in each site. In the present disclosure, the highest diffraction peak of each crystalline form was taken as the base peak which was defined as $I_0$ with the relative intensity as 100%, and other peaks had the ratio of their peak height to the peak height of base peak as the relative intensity $I/I_0$. The definition of the relative intensity of each peak was shown in the following table 17:

TABLE 17

| relative intensity $I/I_0$(%) | Definition |
| --- | --- |
| 50-100 | VS (very strong) |
| 20-50 | S (strong) |
| 10-20 | M (medium) |
| 0-10 | W (weak) |

The acid-base molar ratio of the salts of the present disclosure or their crystalline forms was determined by HPLC/IC or $^1$H NMR.

The liquid nuclear magnetic spectrum was collected on a Bruker 400M NMR spectrometer with DMSO-$d_6$ as the solvent.

High performance liquid chromatography spectrum was acquired on an Agilent 1260 HPLC, the specific instrument and test parameters are shown in the table 18 below.

TABLE 18

| Column | Extend C18, 150*4.6 mm, 5 μm, PN773450-902 | | | |
|---|---|---|---|---|
| Mobile phase | A: 0.1% aqueous solution of trifluoroacetic acid | | | |
| | B: 0.1% trifluoroacetic acid in acetonitrile | | B: acetonitrile | |
| Gradient | Time (min) | B (%) | Time (min) | B (%) |
| | 0.0 | 5 | 0.0 | 5 |
| | 1.0 | 5 | 0.5 | 5 |
| | 13 | 95 | 8 | 95 |
| | 14 | 95 | 13 | 95 |
| | 14.1 | 5 | 13.1 | 5 |
| | 15 | 5 | 15 | 5 |
| Operation times | 15 minutes | | 15 minutes | |
| Post-running time | 0 minute | | 0 minute | |
| Velocity | 1.0 ml/min | | 0.8 ml/min | |
| Sample volume | 5 μL | | 5 μL | |
| Detection wavelength | DAD(254 nm) | | DAD(250 nm) | |
| Column temperature | 25° C. | | 25 °C. | |
| Diluent | DMSO | | 40% acetonitrile solution | |

TGA and DSC pattern were acquired on a TGA Q500 V20.10 Build 36 thermogravimetric analyzer and a DSC Q2000 V24.4 Build 116 differential scanning calorimeter respectively, test parameters are shown in the following table 19.

TABLE 19

| Parameter | TGA | DSC |
|---|---|---|
| Method | Linear warming | Linear warming |
| Sample tray | Platinum plate, open | Aluminum plate, gland |
| Temperature range | 25° C. - set temperature | 25° C. - set temperature |
| Scanning rate (° C./min) | 10 | 10 |
| Protective gas | Nitrogen | Nitrogen |

The Dynamic Vapor Sorption (DVS) curve was acquired on the DVS Intrinsic of Surface Measurement Systems. The DVS test parameters are listed in the table 20 below.

TABLE 20

| Parameters | Setting value |
|---|---|
| Temperature | 25° C. |
| Sample size | 10-20 mg |
| Protective gas | $N_2$, 0.1 MPa |
| dm/dt | 0.01%/min |
| Minimum dm/dt balance time | 5 minutes |
| The maximum balance time | 120 minutes |
| RH range | 0% RH-95% RH |
| RH gradient | 5% RH |

It should be understood that different values may be obtained when other types of instruments with the same function as the instruments described above or test conditions which are different from the conditions used in the present disclosure were used. Therefore, the recited value should not be considered as an absolute numerical value.

Due to the instrumental errors or different operators, one skilled in the art will understand that the above parameters used to characterize the physical properties of crystals may differ slightly, so the parameters described above are only used to assist in characterizing the polymorphs provided herein, and can not be regarded as a limitation on the polymorphs of the present disclosure.

Preparation of Compound X-a:

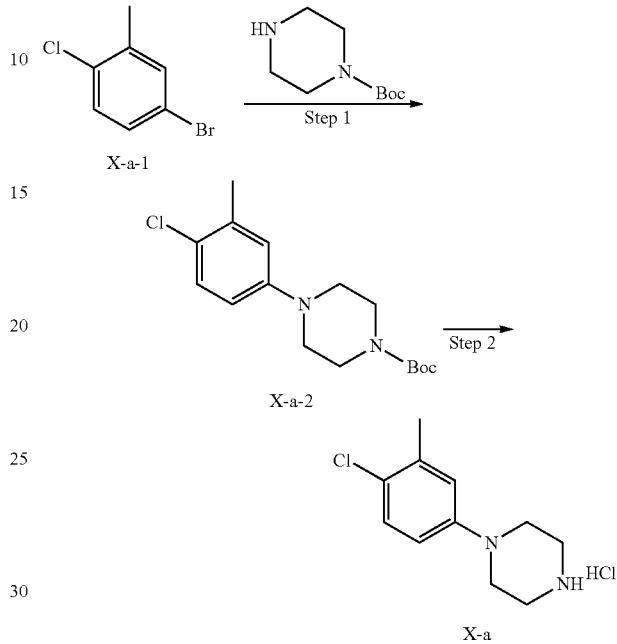

Step 1: A solution of compound X-a-1 (90 g, 0.438 mol), N-Boc-piperazine (114 g, 0.613 mol), pd$_2$(dba)$_3$ (4.0 g, 0.004 mol), BINAP (5.1 g, 0.008 mol) and potassium tert-butoxide (98 g, 0.876 mol) in 1,4-dioxane (1 L) was heated to 100° C. and stirred for 3 h. The mixture was poured into water, filtered over celite and washed with ethyl acetate. The filtrate was extracted by ethyl acetate (1L*2), the organic layers were combined, washed with saturated brine (500 mL), dried over anhydrous sodium sulfate and concentrated, the residue was recrystallized from ethanol to give 44 g of solid compound X-a-2. ESI-MS [M+H]$^+$: 311.2.

Step 2: A solution of compound X-a-2 (82 g, 0.264 mol) in methanol (800 mL) was added dropwise with hydrochloric acid/1,4-dioxane (4M, 264 mL) under the ice bath, the mixture was allowed to warm to room temperature overnight, the reaction solution was filtered, washed with methanol and dried to give a white solid compound X-a (72 g, yield: 100%). ESI-MS [M+H]$^+$: 211.1.

Example 1 Preparation of the Compound of Formula X

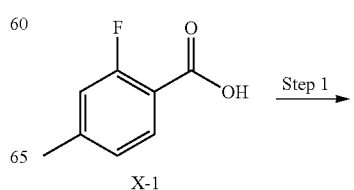

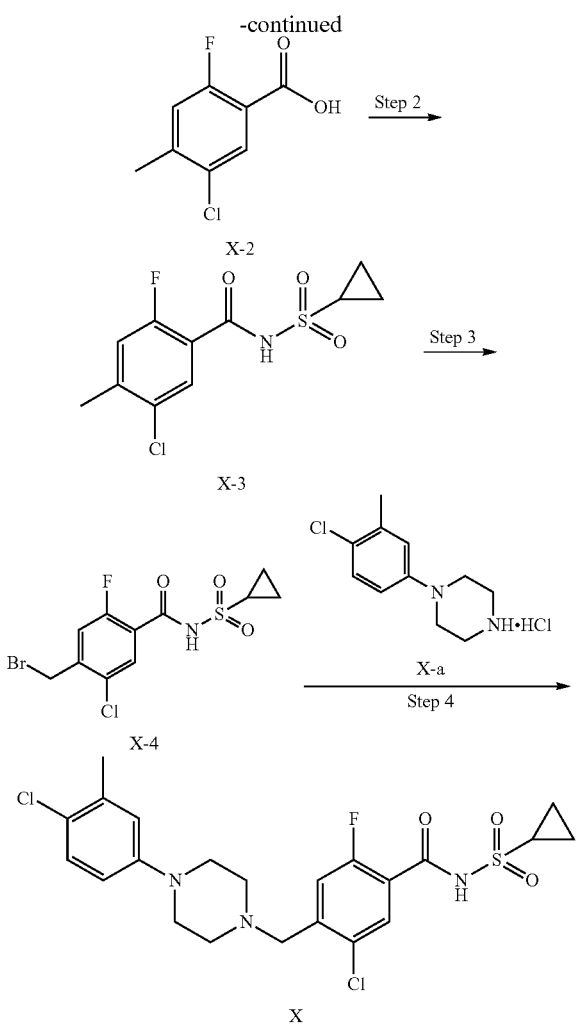

Step 1: Compound X-1 (100.1 g, 0.65 mol) was added to concentrated sulfuric acid (300 ml), DCDMH (64.03 g, 0.325 mol) was added portionwise over 30 minutes. The mixture was slowly warmed to 40° C. over 2 hours, and the reaction was clarified. The mixture was slowly cooled to room temperature, and a solid was precipitated and the mixture was stirred at room temperature for 16 h. The mixture was slowly poured into ice water, filtered, and the filter cake was washed with water and dried to give white solid compound X-2 (108 g, yield: 88.2%). ESI-MS [M+H]$^+$: 189.

Step 2: A mixed solution of compound X-2 (128 g, 0.677 mol), cyclopropylsulfonamide (164 g, 1.354 mol), EDC.HCl (260 g, 1.354 mol), DMAP (83 g, 0.677 mol) and DIPEA (262 g, 2.031 mol) in dichloromethane (1200 mL) was stirred at room temperature for 3 days. The reaction solution was spin dried, the solid was dissolved in water (1 L), adjusted to pH 3-4 with concentrated hydrochloric acid, extracted with ethyl acetate (800 mL*3), the organic layers were combined, washed with saturated brine (800 mL), dried over anhydrous sodium sulfate, filtered, the filtrate was concentrated to remove most of the solvent and then filtered. The filter cake was recrystallized from ethanol to give white solid compound X-3 (106 g, yield: 53.8%). MS m/z (ESI): 292 [M+H]$^+$.

Step 3: A solution of compound X-3 (100 g, 0.342 mol), NBS (91.4 g, 0.514 mol) and azobisisobutyronitrile (2.8 g, 0.017 mol) in acetonitrile (1 L) was heated to 80° C. and stirred for 3 hours. The reaction solution was concentrated with a rotary evaporator. The residue was dissolved in ethyl acetate (1 L), washed with water (500 mL) and saturated brine (200 mL), dried over anhydrous sodium sulfate, filtered, and the filtrate was concentrated to remove most of the solvent and filtered. Diethyl phosphite (35.4 g, 0.257 mol) and DIPEA (66 g, 0.513 mol) were added to the filter cake, adjusted to pH 2-3 with hydrochloric acid (2N), washed with saturated brine (200 mL), dried over anhydrous sodium sulfate, filtered, the filtrate was concentrated to remove most of the solvent and then filtered. The filter cake was washed with petroleum ether and dried to give white solid compound X-4 (88 g, yield: 65.4%). MS m/z (ESI): 370 [M+H]$^+$.

Step 4: A mixed solution of compound X-4 (88 g, 0.237 mol), compound X-a (58.7 g, 0.237 mol), potassium carbonate (65.4 g, 0.474 mol) in DMF (900 mL) was stirred at 80° C. for 3 h. The reaction solution was poured into water (1.5 L), extracted with ethyl acetate (800 mL*4), the organic layers were combined, washed with water (1000 mL*2) and saturated brine (500 mL), dried over anhydrous sodium sulfate, filtered, and the filtrate was concentrated to dryness. The residue was purified by column chromatography to obtain white solid compound X (87 g, yield: 73.7%). MS m/z (ESI): 500.2 [M+H]$^+$.

Figure 9A:
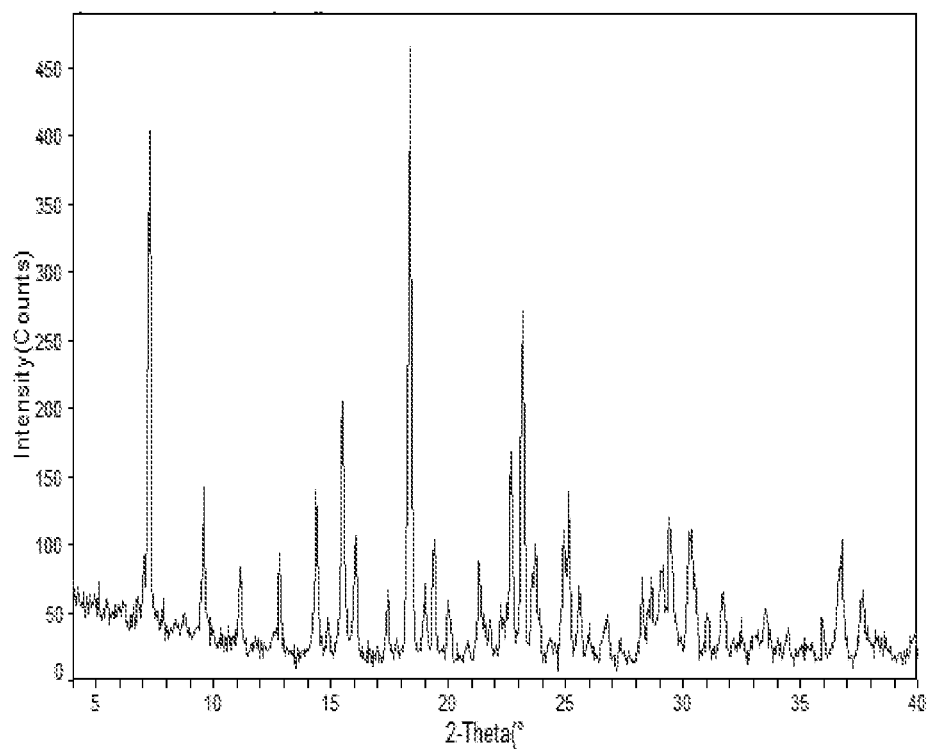
FIG. 9A is the X-ray powder diffraction pattern of crystal form I.
Figure 9B:
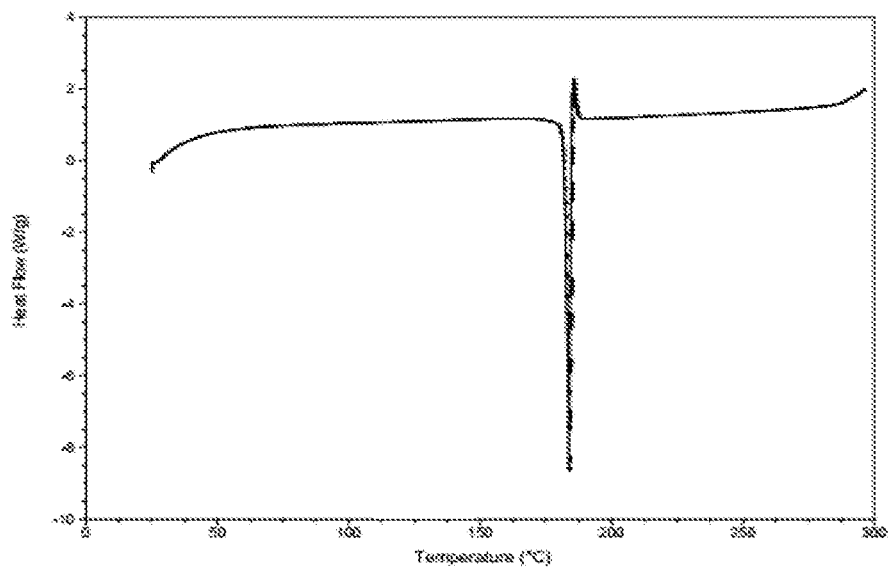
FIG. 9B is the differential scanning calorimetry analysis spectrum of crystal form I.
Figure 9C:
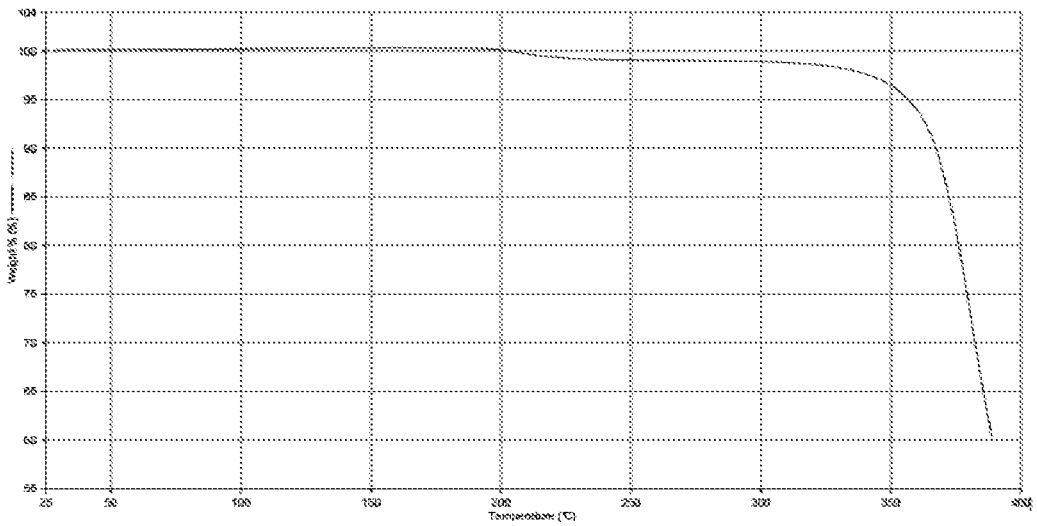
FIG. 9C is the thermogravimetric analysis spectrum of crystal form I.
Figure 9D:
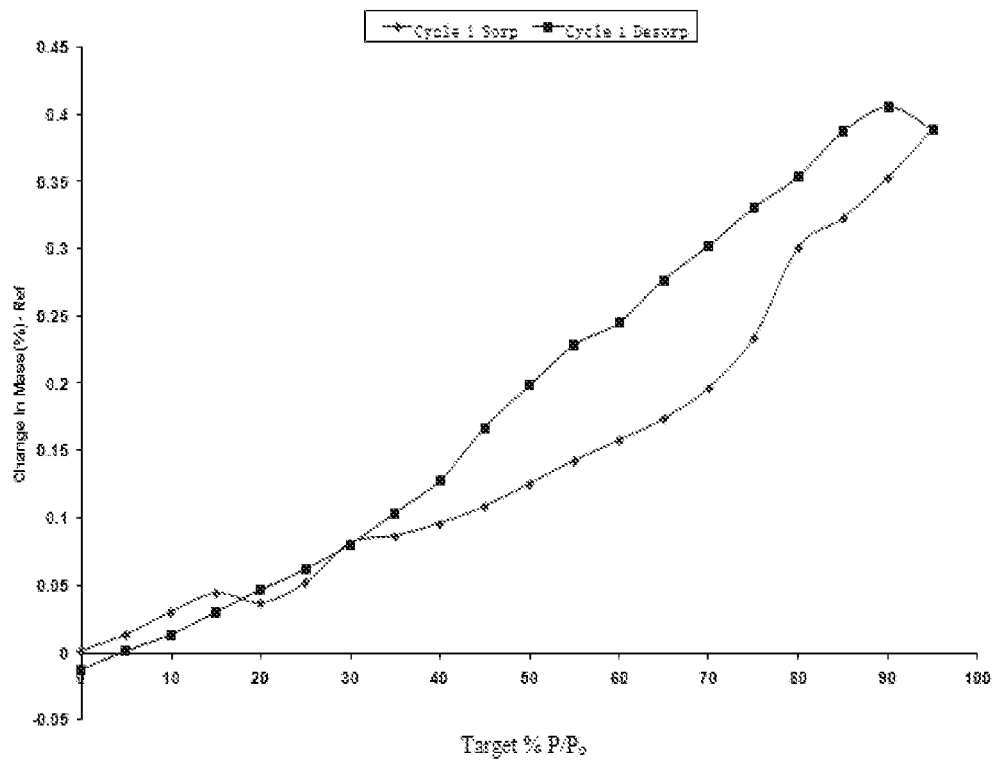
FIG. 9D is the DVS curve of crystal form I.

Example 2 Preparation of Crystal Form I of a Free Base of the Compound of Formula X The First Method About 20 mg of the compound of formula X prepared in Example 1 (hereinafter referred to as "free base sample") was weighed into a glass vial, and an appropriate amount of each of the following solvents (Table 21) was added to obtain a nearly saturated solution, which was fully dissolved by ultrasound. After filtration, 20-200 uL of the corresponding solvent was added to the clear solution, and slowly volatilized at room temperature. After the solvent was completely evaporated, the solid was collected for XRPD test. The X-ray powder diffraction pattern is shown in FIG. 9A. The DSC/TGA/DVS pattern are shown in FIGS. 9B, 9C and 9D. It can be seen from the DSC pattern that there is a melting absorption peak at 183.76° C. (starting temperature); there is almost no weight loss when heated to 150° C., and when it is heated to 200° C., the weight loss is 1.159%; the DVS curve indicates that the sample is slightly hygroscopic. The crystal form I has good stability.

TABLE 21

| Solvent | Crystal form |
| --- | --- |
| ACN | crystal form I |
| Actone | crystal form I |
| EtOAc | crystal form I |

The Second Method

About 40-50 mg of the free base sample was weighed into a glass vial, and an appropriate amount of each of the following solvents (Table 22) was added respectively under 60° C. water bath, the mixture was stirred to dissolve and obtain a nearly saturated solution. After filtration, 20-200 uL of the corresponding solvent was added to the clear solution. The heating button was turned off and the solution was allowed to cool slowly. After cooling to room temperature, the solution was continuously cooled to about 4° C. under an ice bath to collect the suspension. The liquid was centrifuged at 12000 r/min for 15 min. The supernatant was poured, the solid was allowed to slowly volatilize overnight at room temperature, and the resulting solid was collected and subjected to XRPD test.

TABLE 22

| Solvent | Experimental result | Crystal form |
|---|---|---|
| ACN | transparent crystal particles are precipitated at the bottom and the walls of vial | crystal form I |
| MeOH | transparent crystal particles are precipitated at the bottom of vial | crystal form I |
| EtOH | transparent crystal particles are precipitated at the bottom of vial | crystal form I |
| IPA | NA | |
| Actone | a large amount of powdered solid are precipitated at the bottom | crystal form I |
| EtOAc | a powdered solid is precipitated at the bottom | crystal form I |
| THF | NA | |
| MTBE | NA | |

The Third Method

About 40 mg of the free base sample was weighed into a glass vial, an appropriate amount of good solvent was added respectively to obtain a nearly saturated solution, the anti-solvent was then added milliliter by milliliter to observe whether solids were precipitated, the anti-solvent was continuously added until the solids were not precipitated from sample or until the solids were impossible to be precipitated from sample. The liquid was centrifuged, the supernatant was poured, evaporated to collect the resulting solid for XRPD test. The specific solvents are shown in Table 23 and Table 24.

TABLE 23

Anti-solvent addition experiments at room temperature

| Good solvent | Anti-solvent | Experimental phenomena | Crystal form |
|---|---|---|---|
| THF | H$_2$O | NA | / |
| DMSO | | the flocculated white solid was precipitated | amorphous form |
| DMAc | | the granular white solid was precipitated | crystal form I |
| THF | n-heptane | NA | / |
| DMSO | | immiscible | / |
| DMAc | | immiscible | / |

TABLE 24

Anti-solvent addition experiments at 60° C.

| Good solvent | Anti-solvent | Experimental phenomena | Crystal form |
|---|---|---|---|
| Actone | n-heptane | NA | / |
| ACN | | immiscible | / |
| MeOH | | immiscible | / |
| EtOAc | | transparent crystal was precipitated | crystal form I |

The Fourth Method

About 20 mg of the free base sample was weighed into a glass vial, and 1 mL of the following organic reagents were added, tightly capped the vial and sealed with a sealing film to prevent liquid evaporation, placed at 25° C., shaken at 25 r/min, and then centrifuged at 14000 r/min for 15 min at 4° C., the supernatant was poured, and the solid was allowed to slowly evaporate overnight at room temperature. The resulting solid was collected and subjected to XRPD test. The test results are shown in Table 25 below.

TABLE 25

Summary of mixed shaking experiments at 25° C.

| Solvent | Solid Crystal form obtained by shaking for 1 day | Solid Crystal form obtained by shaking for 7 days |
|---|---|---|
| MeOH | crystal form I | crystal form I |
| EtOH | crystal form I | crystal form I |
| ACN | crystal form I | crystal form I |
| EtOAc | crystal form I | crystal form I |
| MTBE | crystal form I | crystal form I |
| Actone | crystal form I | crystal form I |
| IPA | crystal form I | crystal form I |
| H2O | crystal form I | crystal form I |
| THF | fully dissolved | |

Figure 10A:
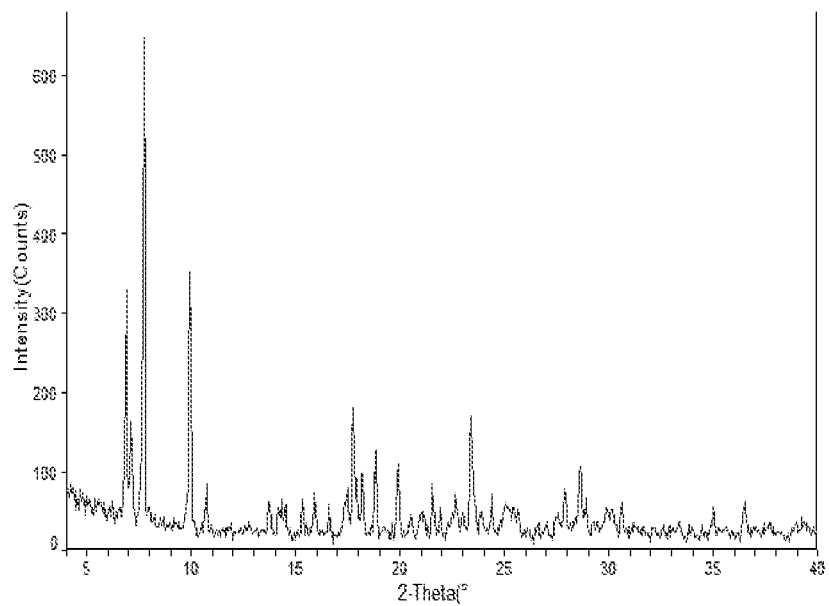
FIG. 10A is the X-ray powder diffraction pattern of crystal form II.
Figure 10B:
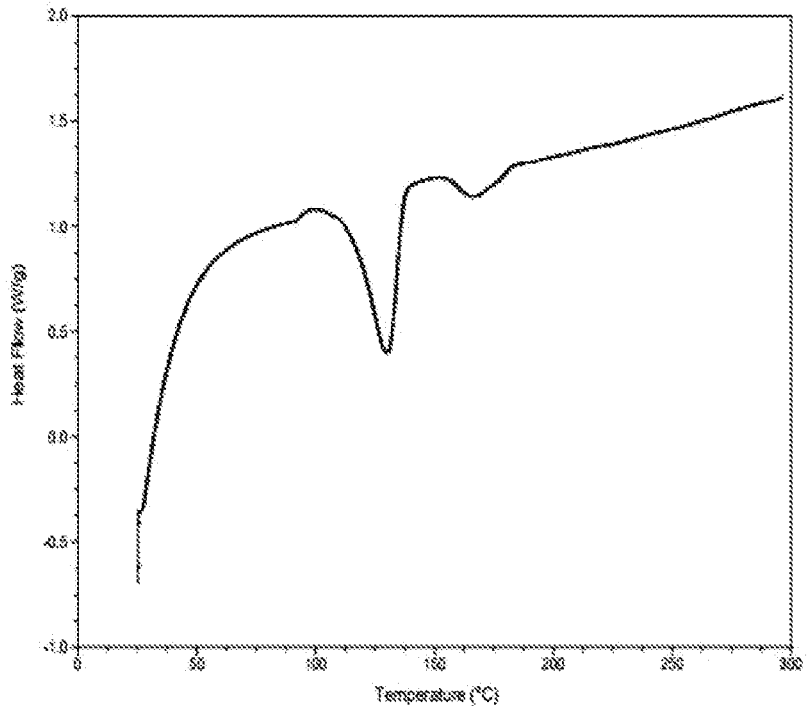
FIG. 10B is the differential scanning calorimetry analysis spectrum of crystal form II.
Figure 10C:
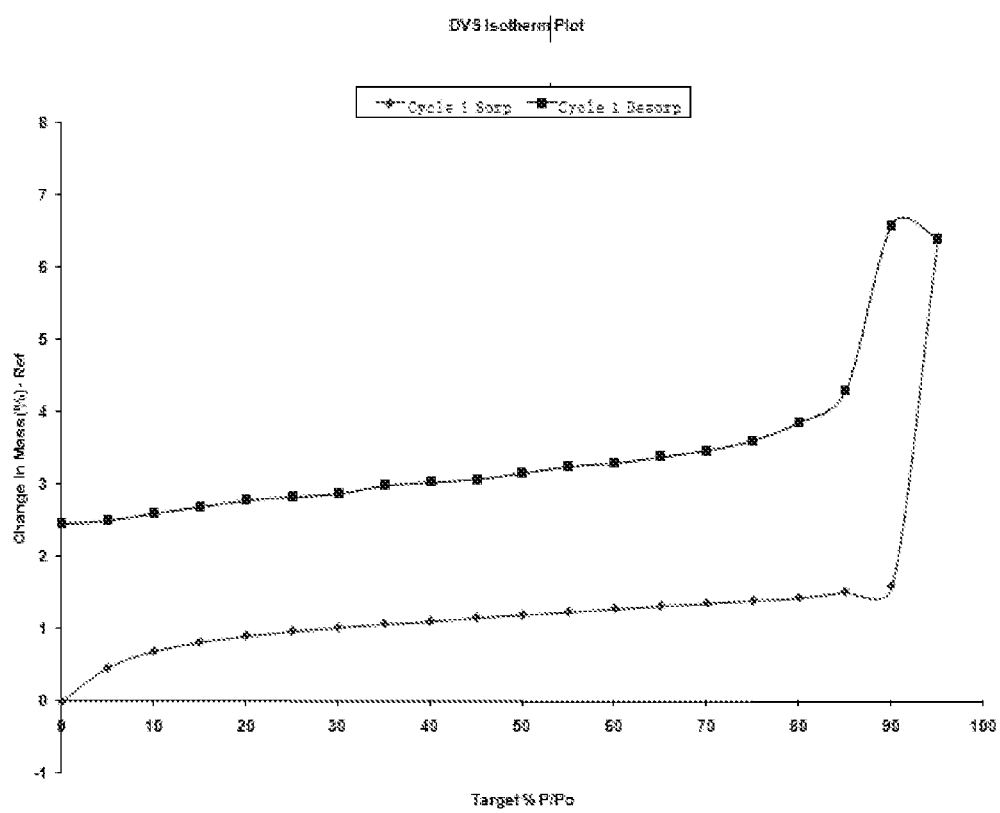
FIG. 10C is the DVS curve of crystal form II.

Example 3 Preparation of Crystal Form II of the Free Base of Compound of Formula X The reaction solution in the step 4 of Example 1 was poured into water, extracted with ethyl acetate, dried and concentrated, ethanol was added and the suspension was stirred for 2 h, filtered, the filter cake was recrystallized from methanol to obtain a solid product which was the crystal form II of free base, the X-ray powder diffraction pattern is shown in FIG. 10A (the 2θ angle has been marked), the DSC/DVS patterns are shown in FIGS. 10B and 10C. According to the DSC pattern, the sample has a melting absorption peak at 130.44° C. (starting temperature) and 167.49° C. respectively; the DVS curve indicates that the sample is hygroscopic.

Figure 11A:
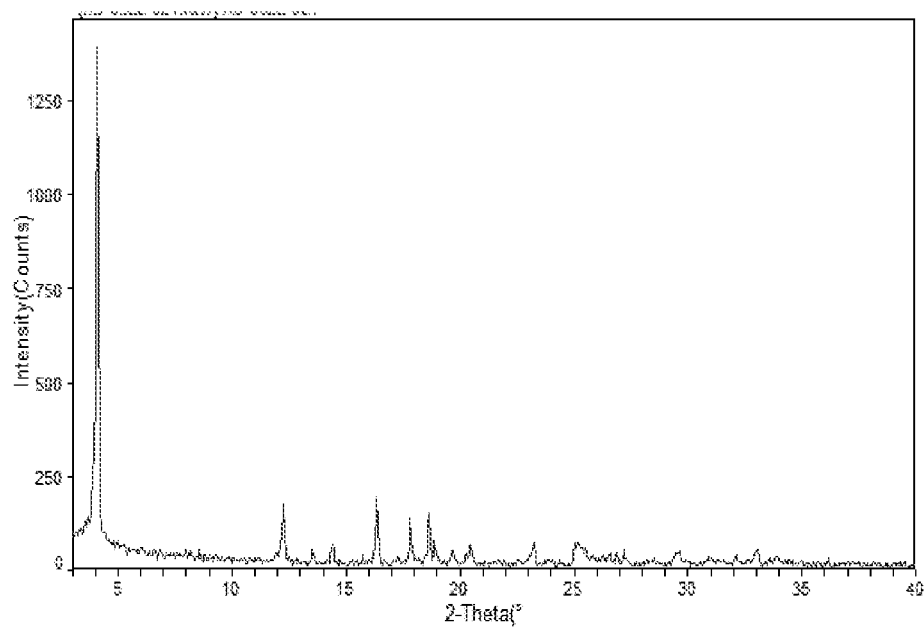
FIG. 11A is the X-ray powder diffraction pattern of crystal form III.
Figure 11B:
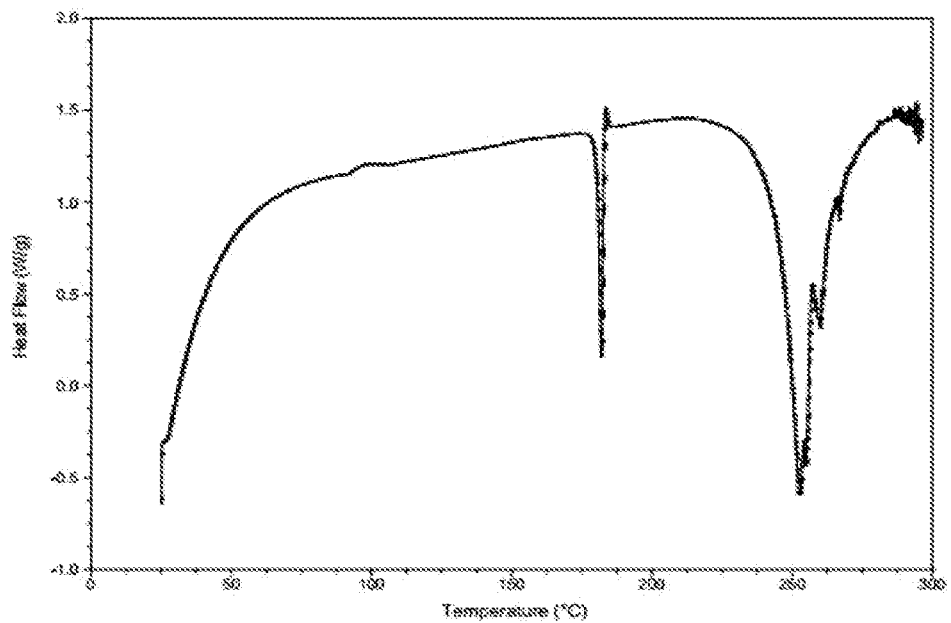
FIG. 11B is the differential scanning calorimetry analysis spectrum of crystal form III.
Figure 11C:
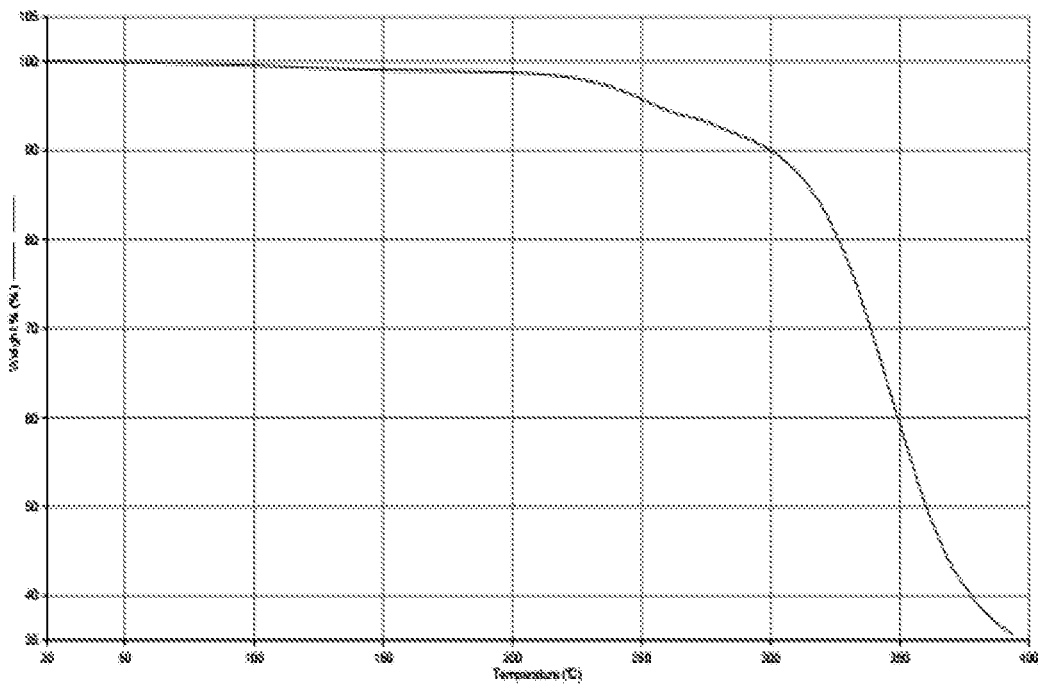
FIG. 11C is the thermogravimetric analysis spectrum of crystal form III.
Figure 11D:
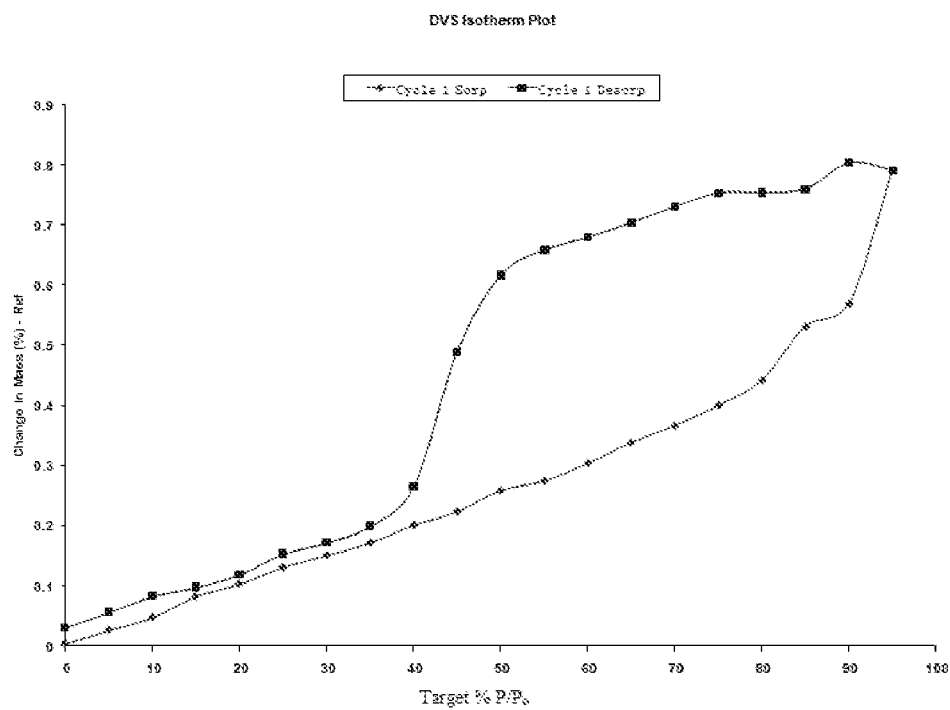
FIG. 11D is the DVS curve of crystal form III.

Example 4 Preparation of Crystal Form III of the Free Base of Compound of Formula X The reaction solution in the step 4 of Example 1 was poured into water, extracted with ethyl acetate, dried and concentrated, ethanol was added to dissolve and the solution was evaporated, 1N hydrochloric acid and ethyl acetate were added and stirred for 1-2 h, filtered, a solid product which was the crystal form III of free base was obtained, the X-ray powder diffraction pattern is shown in FIG. 11A (the 2θ angle has been marked), the DSC/TGA/DVS patterns are shown in FIGS. 11B, 11C and 11D. According to the DSC pattern, there is an inflection point around 100° C., and the sample has a melting absorption peak at 181.9° C. (starting temperature); the sample was heated to 100° C. and the weight loss was 0.714%; the DVS curve indicated that the sample was slightly hygroscopic. The sample was shaken in ACE and MeOH at 50° C. for 1 day, and the crystal form was unchanged. The sample was mixed with crystal form IV in ACE and MeOH and shaken at 50° C. for 1 day, and all of them were converted into crystal form I. It is speculated that the sample is a metastable crystal form, and the crystal form I is more stable.

Figure 12A:
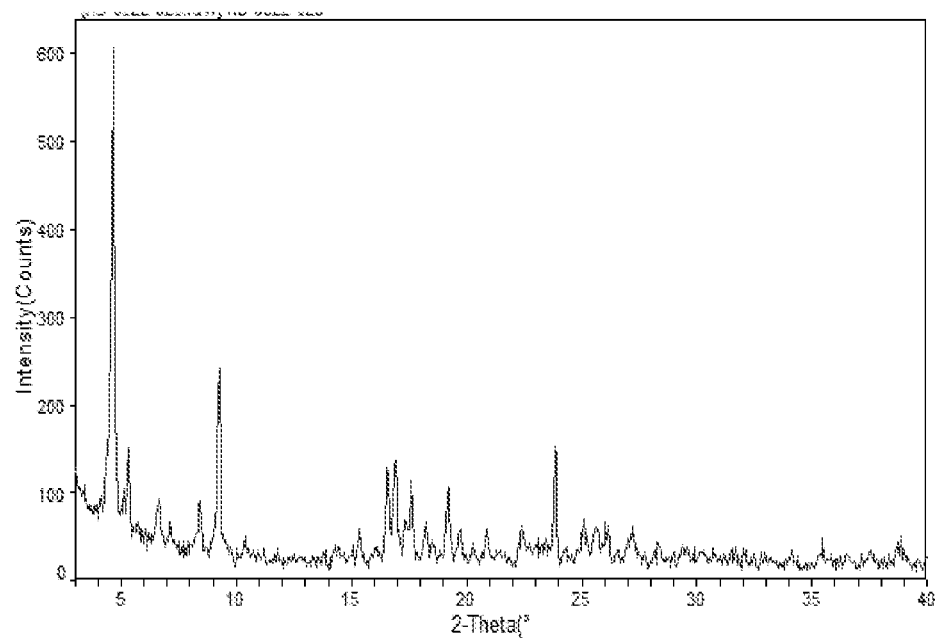
FIG. 12A is the X-ray powder diffraction pattern of crystal form IV.
Figure 12B:
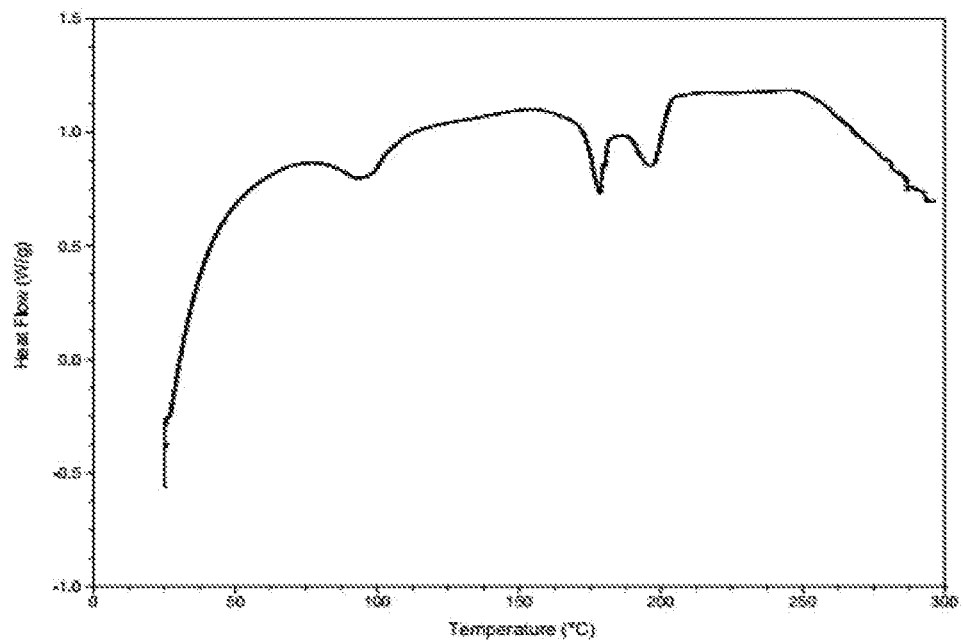
FIG. 12B is the differential scanning calorimetry analysis spectrum of crystal form IV.
Figure 12C:
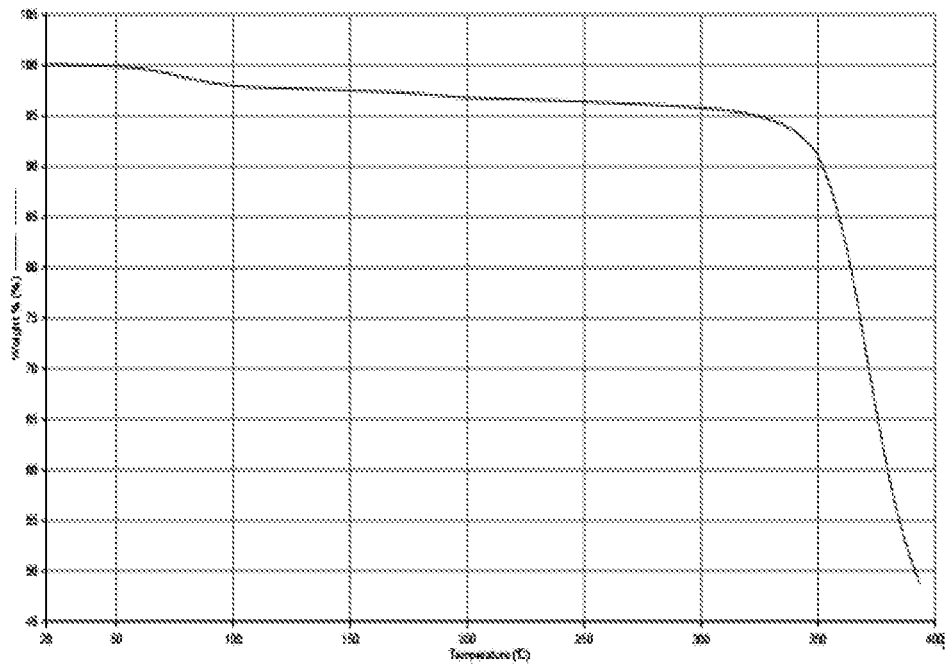
FIG. 12C is the thermogravimetric analysis spectrum of crystal form IV.
Figure 12D:
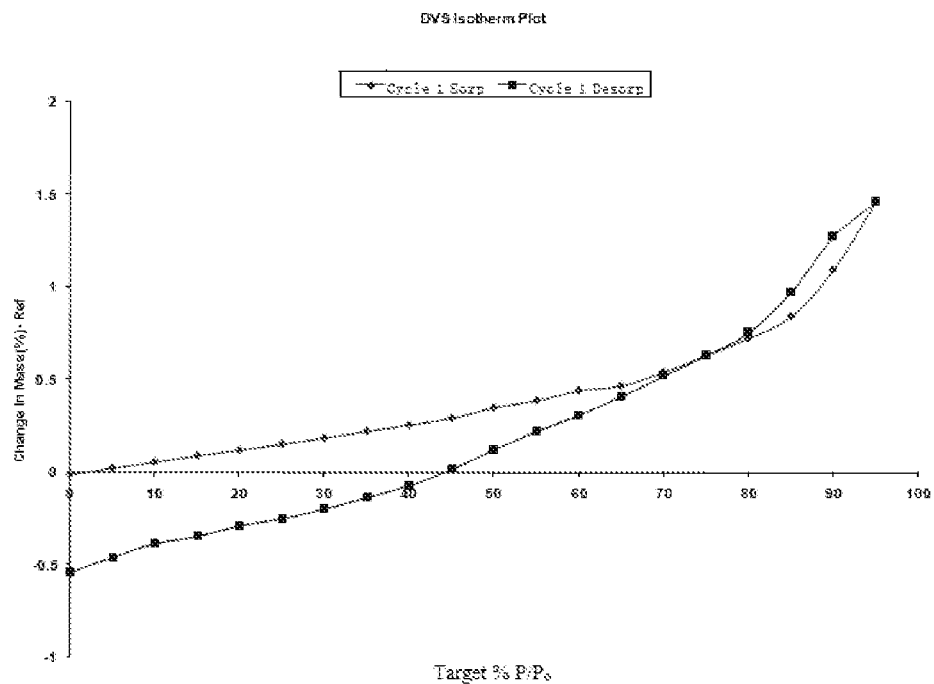
FIG. 12D is the DVS curve of crystal form IV.

Example 5 Preparation of Crystal Form IV of the Free Base of Compound of Formula X The reaction solution in the step 4 of Example 1 was poured into water, extracted with ethyl acetate, dried and concentrated to retain a small amount of ethyl acetate, 1N hydrochloric acid was added and stirred for 1 h, filtered, the filter cake was washed with ethanol and then filtered to obtain a solid product which was the crystal form IV of free base was obtained. The X-ray powder diffraction pattern is shown in FIG. 12A (the 2θ angle has been marked), the DSC/TGA/DVS patterns are shown in FIGS. 12B, 12C and 12D. According to the DSC pattern, there is a melting absorption peak at 95.7° C., 187.01° C. and 197.09° C. respectively; the sample was heated to 100° C. and the weight loss was 2.269%; heated to 200° C. and the weight loss was 1.344%; the DVS curve indicated that the sample was slightly hygroscopic. The sample was shaken in ACE at 50° C. for 1 day, and the crystal form was unchanged. The sample was mixed with crystal form III in ACE and MeOH and shaken at 50° C. for 1 day, and all of them were converted into crystal form I. It is speculated that the sample is a metastable crystal form, and the crystal form I is more stable.

Figure 13A:
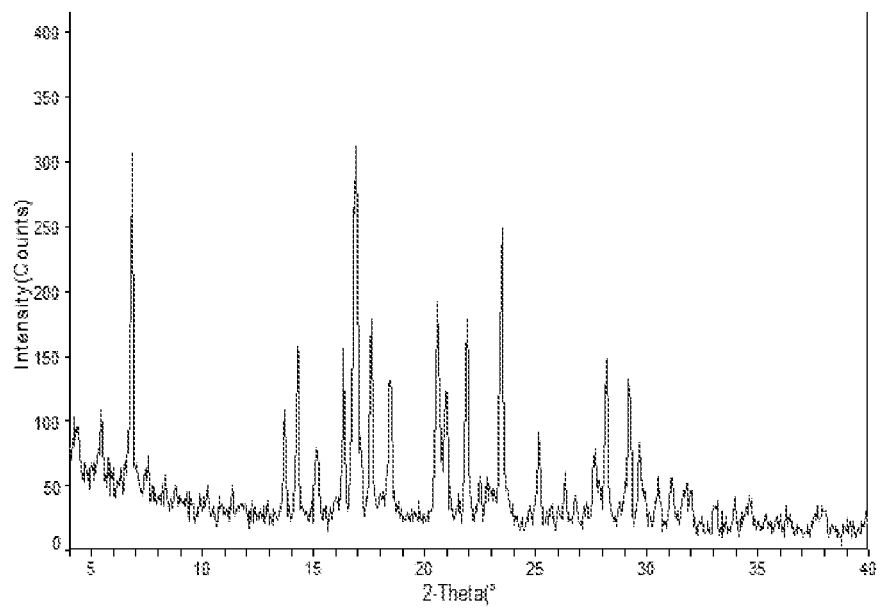
FIG. 13A is the X-ray powder diffraction pattern of crystal form V.
Figure 13B:
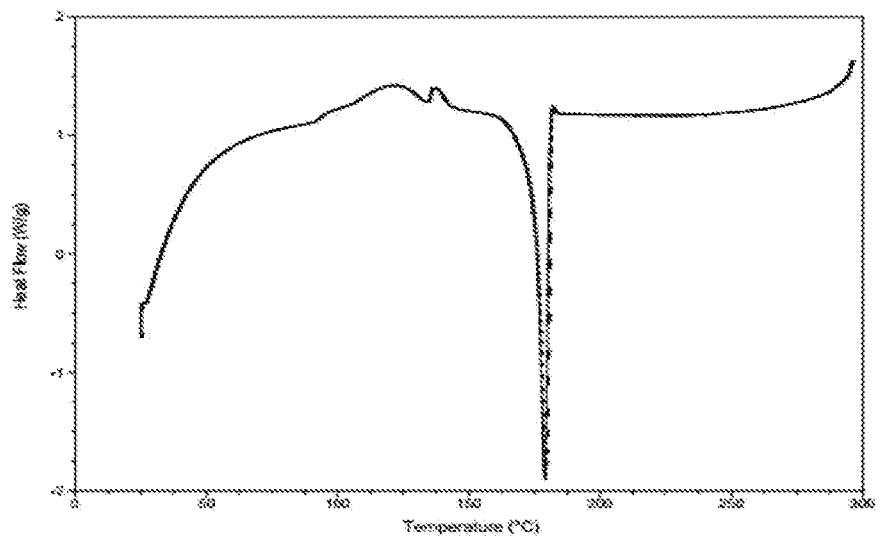
FIG. 13B is the differential scanning calorimetry analysis spectrum of crystal form V.
Figure 13C:
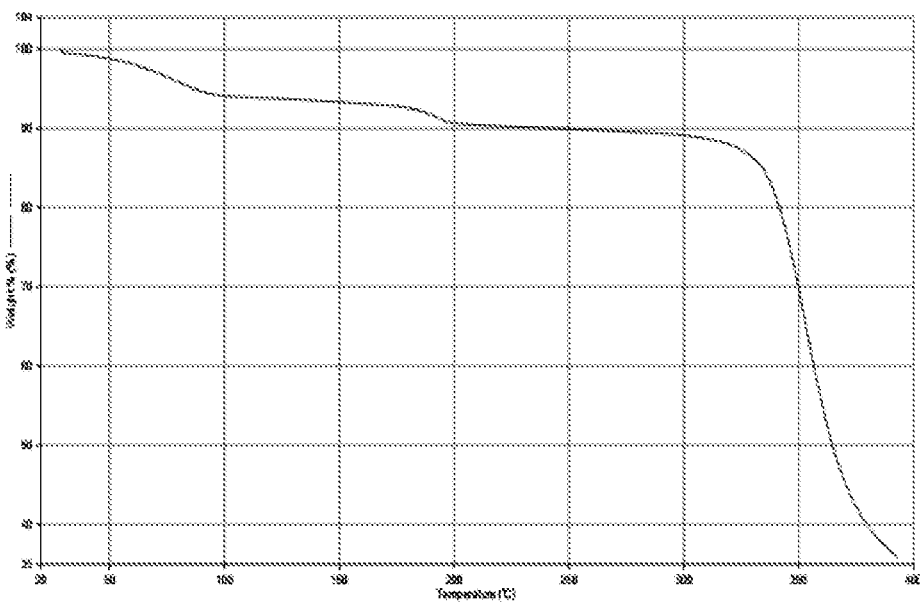
FIG. 13C is the thermogravimetric analysis spectrum of crystal form V.
Figure 13D:
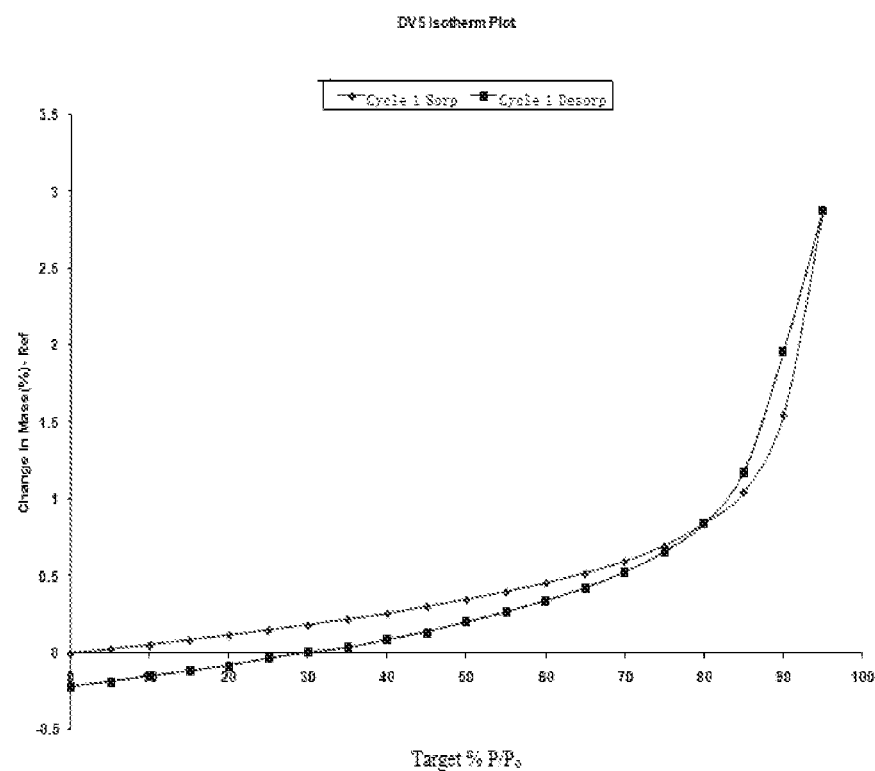
FIG. 13D is the DVS curve of crystal form V.

Example 6 Preparation of Crystal Form V of the Free Base of Compound of Formula X About 20 mg of the free base sample was weighed into a glass vial, and an appropriate amount of THF was added to obtain a nearly saturated solution, which was fully dissolved by ultrasound. After filtration, 20-200 uL of the corresponding solvent was added to the clear solution, and slowly volatilized at room temperature. After the solvent was completely evaporated, crystal form V was obtained, the resulting solid was collected for XRPD test. The X-ray powder diffraction pattern is shown in FIG. 13A (the 2θ angle has been marked), the DSC/TGA/DVS patterns are shown in FIGS. 13B, 13C and 13D. According to the DSC pattern, there is a melting absorption peak at 178.91° C.; the sample was heated to 120° C. and the weight loss was 6.189%; heated to 250° C. and the weight loss was 3.861%; the DVS curve indicated that the sample was slightly hygroscopic. When heated to 150° C., the sample was converted into crystal form I. It is speculated that the sample is a solvate, and the crystal form I is more stable.

Figure 14A:
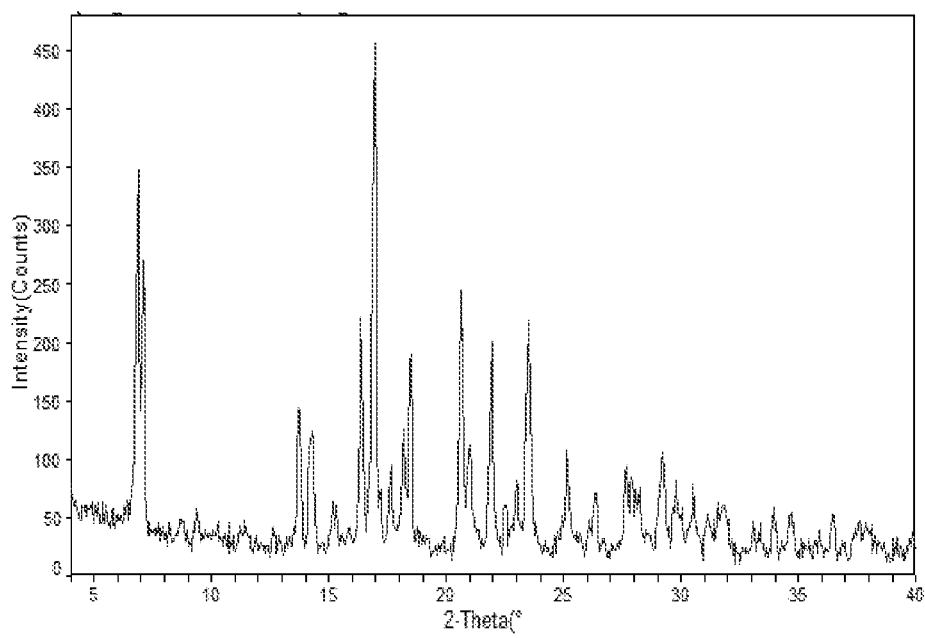
FIG. 14A is the X-ray powder diffraction pattern of crystal form VI.
Figure 14B:
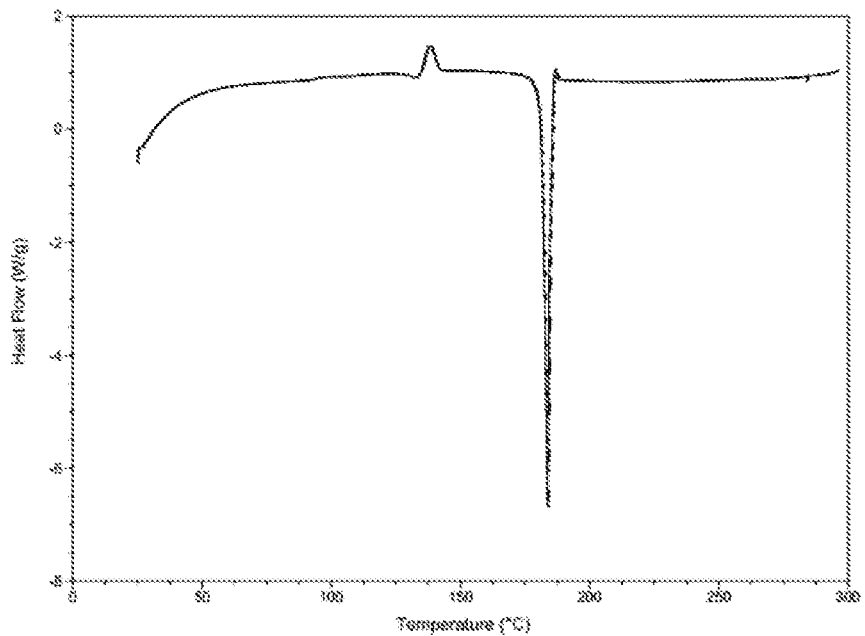
FIG. 14B is the differential scanning calorimetry analysis spectrum of crystal form VI.
Figure 14C:
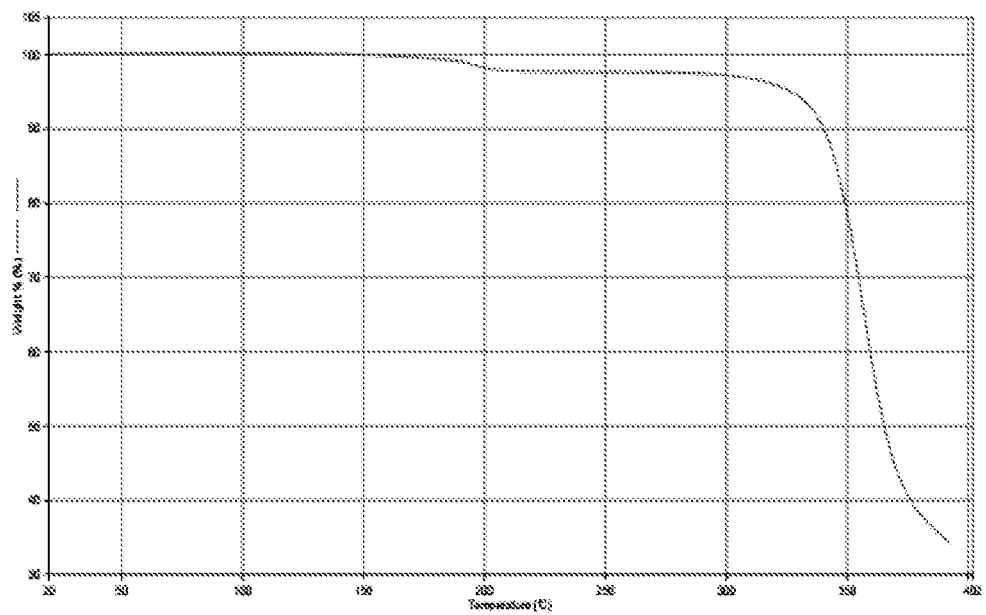
FIG. 14C is the thermogravimetric analysis spectrum of crystal form VI.
Figure 14D:
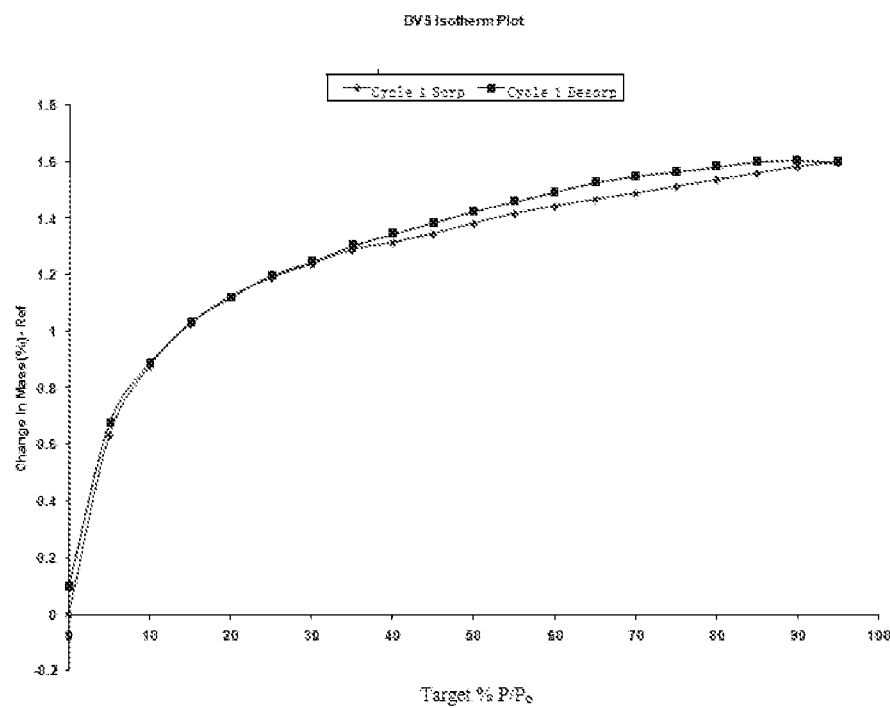
FIG. 14D is the DVS curve of crystal form VI.

Example 7 Preparation of Crystal Form VI of the Free Base of Compound of Formula X About 40 mg sample was weighed into a glass vial, acetone was added to obtain a nearly saturated solution, the anti-solvent water was then added milliliter by milliliter to observe whether solids were precipitated, the anti-solvent was continuously added until the solids were not precipitated from sample or until the solids were impossible to be precipitated from sample. The liquid was centrifuged, the supernatant was poured, evaporated to collect the resulting solid for XRPD test, crystal form VI was obtained. The X-ray powder diffraction pattern is shown in FIG. 14A (the 2θ angle has been marked), the DSC/TGA/DVS patterns are shown in FIGS. 14B, 14C and 14D. According to the DSC pattern, there is an exothermic peak at 138.04° C., and a melting absorption peak at 183.59° C. According to the TGA pattern, the sample was heated to 250° C. and the weight loss was 2.499%; the DVS curve indicated that the sample was slightly hygroscopic. When heated to 150° C., the sample was converted into crystal form I. It is speculated that the sample is a solvate, and the crystal form I is more stable.

Figure 15A:
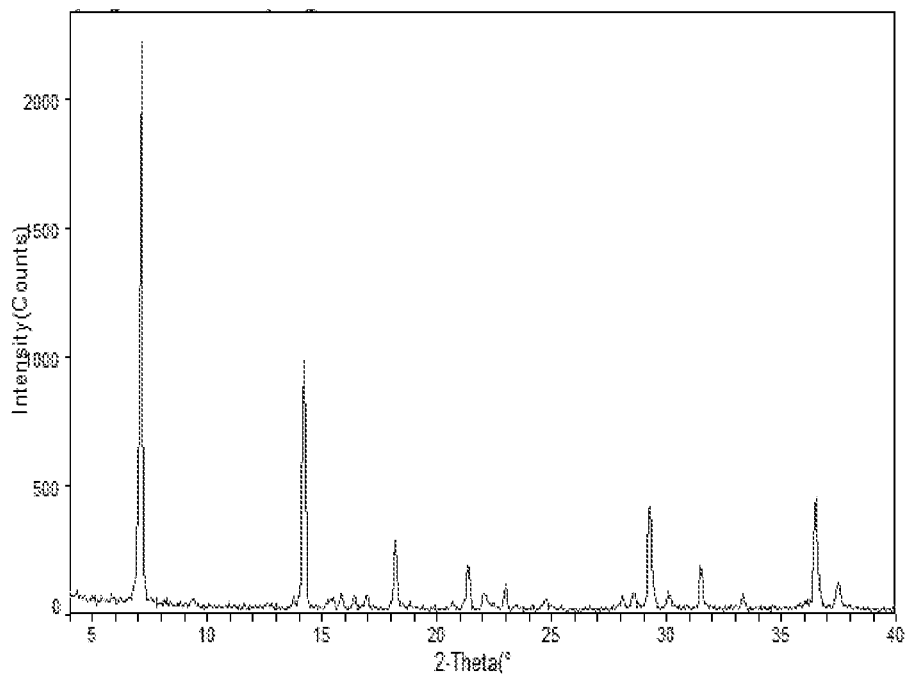
FIG. 15A is the X-ray powder diffraction pattern of crystal form VII.
Figure 15B:
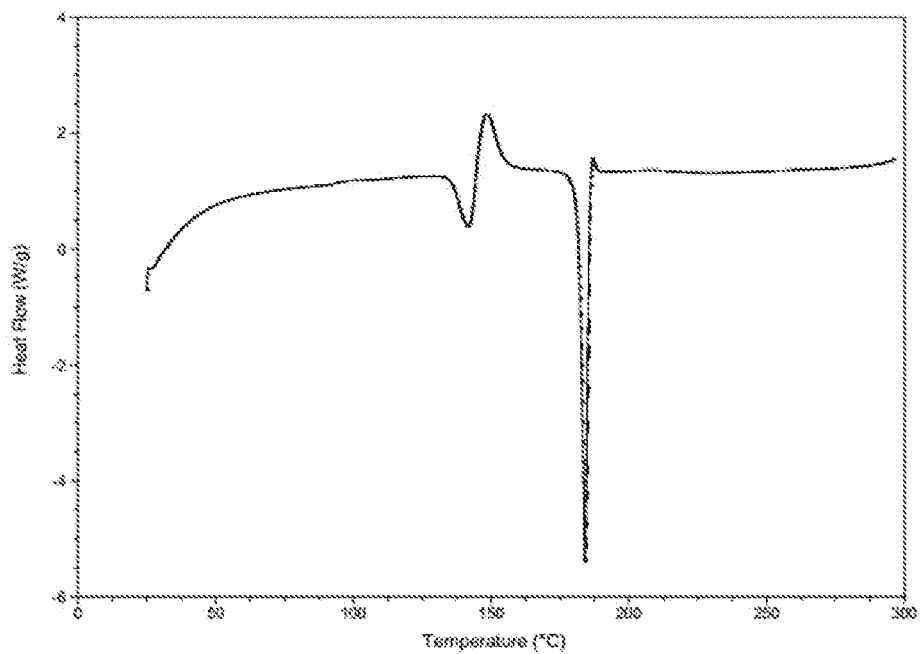
FIG. 15B is the differential scanning calorimetry analysis spectrum of crystal form VII.
Figure 15C:
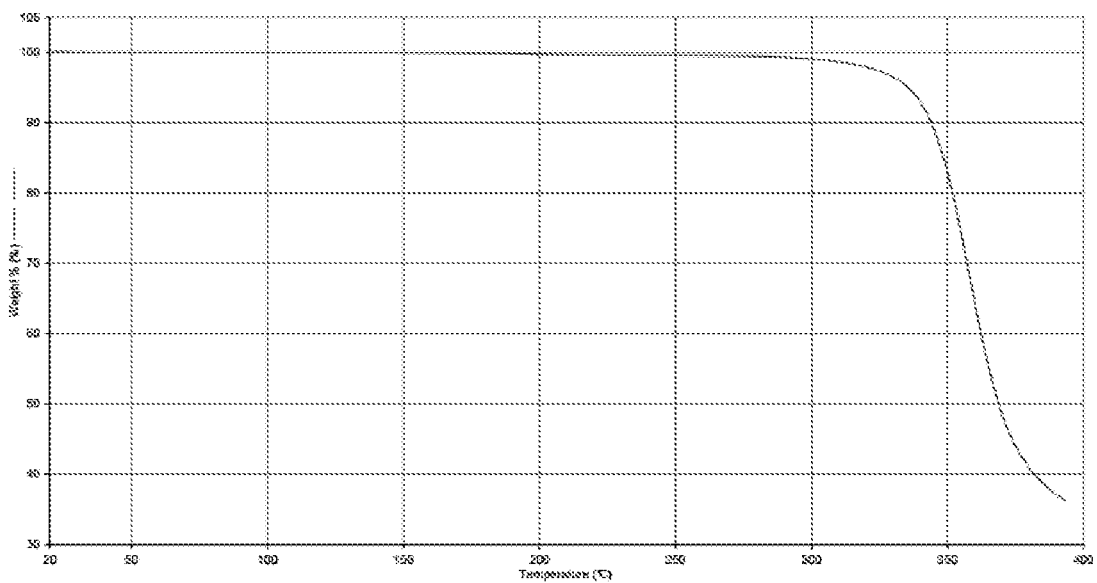
FIG. 15C is the thermogravimetric analysis spectrum of crystal form VII.
Figure 15D:
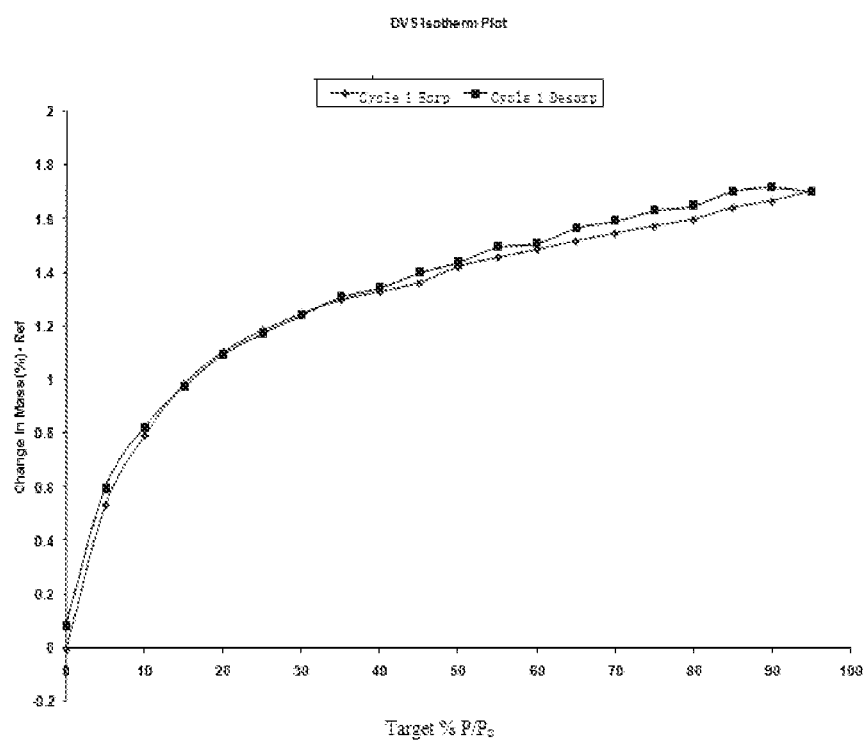
FIG. 15D is the DVS curve of crystal form VII.

Example 8 Preparation of Crystal Form VII of the Free Base of Compound of Formula X About 40 mg sample was weighed into a glass vial, methanol was added to obtain a nearly saturated solution, the anti-solvent water was then added milliliter by milliliter to observe whether solids were precipitated, the anti-solvent was continuously added until the solids were not precipitated from sample or until the solids were impossible to be precipitated from sample. The liquid was centrifuged, the supernatant was poured, evaporated to collect the resulting solid for XRPD test, crystal form VII was obtained. The X-ray powder diffraction pattern is shown in FIG. 15A (the 2θ angle has been marked), the DSC/TGA/DVS patterns are shown in FIGS. 15B, 15C and 15D. According to the DSC pattern, there is an absorption peak at 141.42° C., and an exothermic peak at 148.02° C., and a melting absorption peak at 184.06° C.; the DVS curve indicated that the sample was slightly hygroscopic. When heated to 150° C., the sample was converted into crystal form I. It is speculated that the sample is a solvate, and the crystal form I is more stable.

Figure 1B:
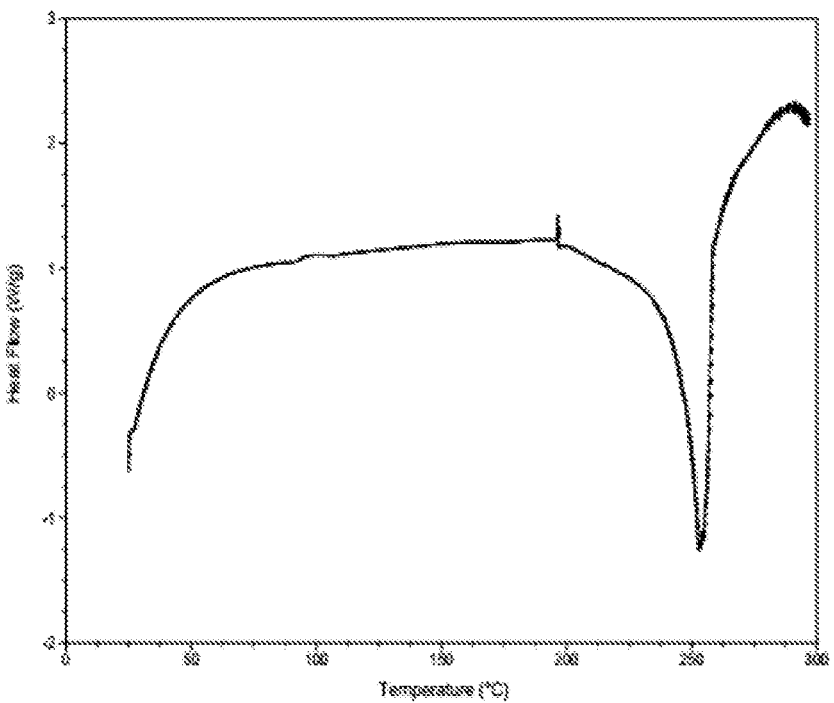
FIG. 1B is the differential scanning calorimetry analysis spectrum of crystal form A.
Figure 1C:
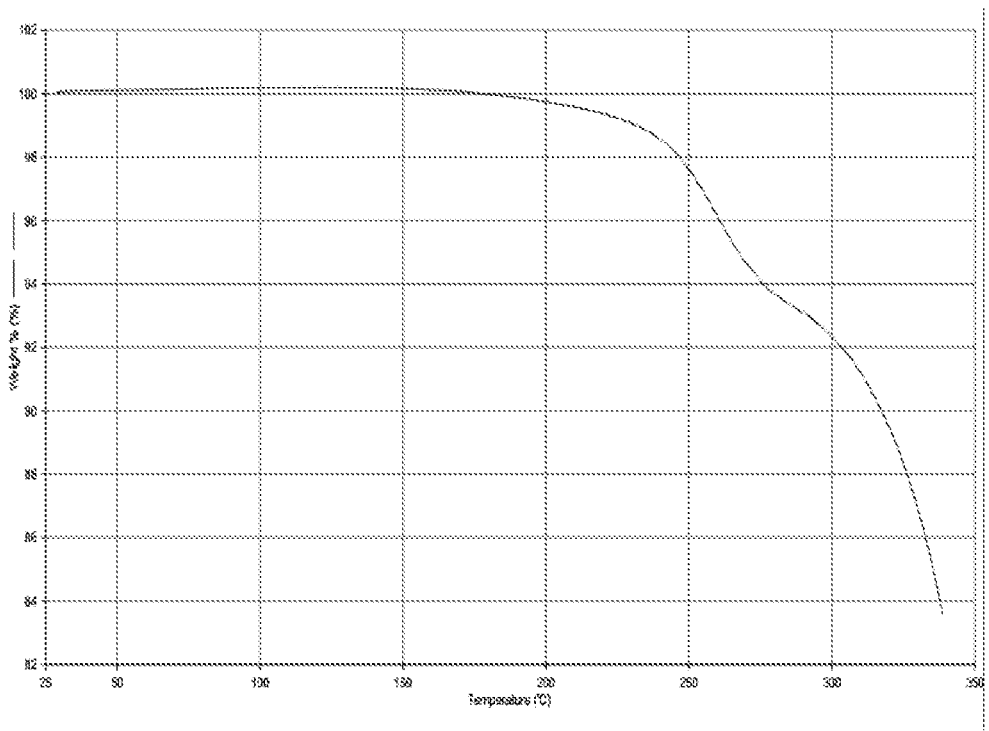
FIG. 1C is the thermogravimetric analysis spectrum of crystal form A.
Figure 1D:
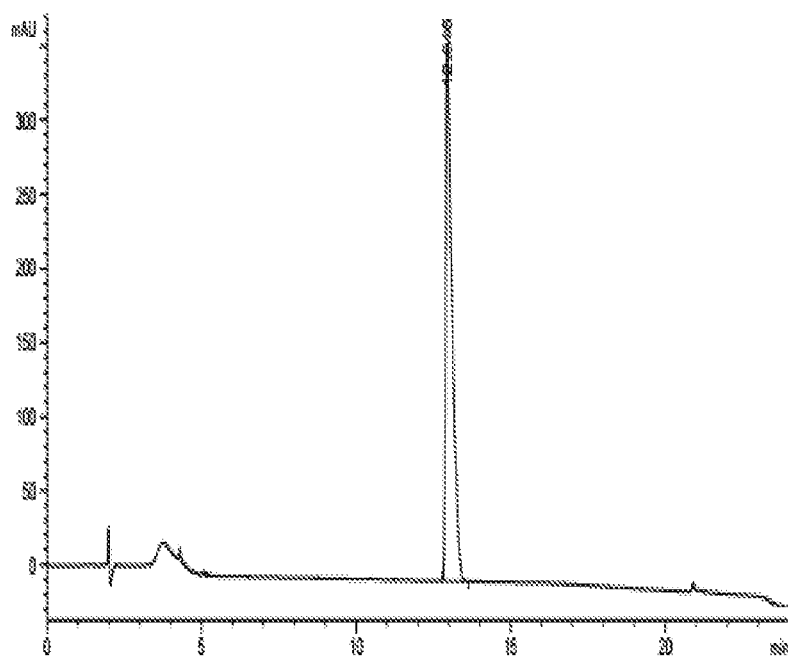
FIG. 1D is the HPLC spectrum of crystal form A.
Figure 1E:
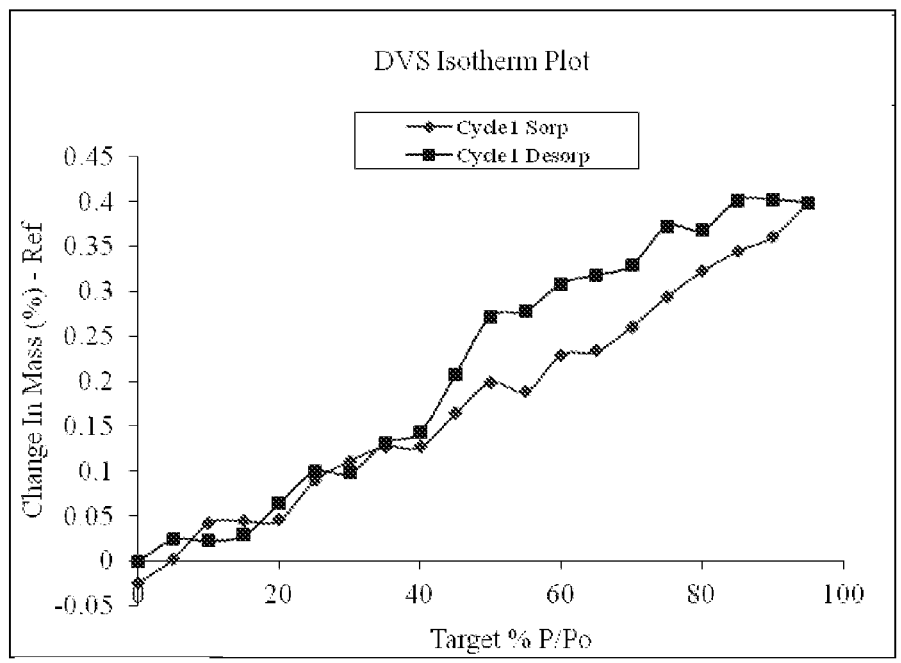
FIG. 1E is the DVS curve of crystal form A.

Example 9 Preparation of Crystal Form a of Compound of Formula X 100 mg of free base sample was weighed into a 20 ml glass sample bottle, 240 μL of 1M hydrochloric acid solution was added at 50° C., 1 mL of methanol was added, and the mixture reacted at this temperature for 4 h, the solution was turbid; slowly cooled to 0° C. after 4 hours, the solid precipitation increased and was obtained by centrifugation. After the solvent was evaporated, a solid product was obtained. The X-ray powder diffraction pattern of the obtained crystal is shown in FIG. 1A (2θ angle has been marked), and the DSC/TGA patterns are characterized as shown in FIGS. 1B and 1C. The weight loss of the sample is 0.196% below 100° C., and there is an endothermic peak in the DSC pattern of the sample. The peak temperature is 252.81° C. HPLC is shown in FIG. 1D; the molar ratio of acid to base is 1:0.93, and the melting point is 243° C.-252° C. The crystal form is defined as crystal form A in the present application.

Figure 2A:
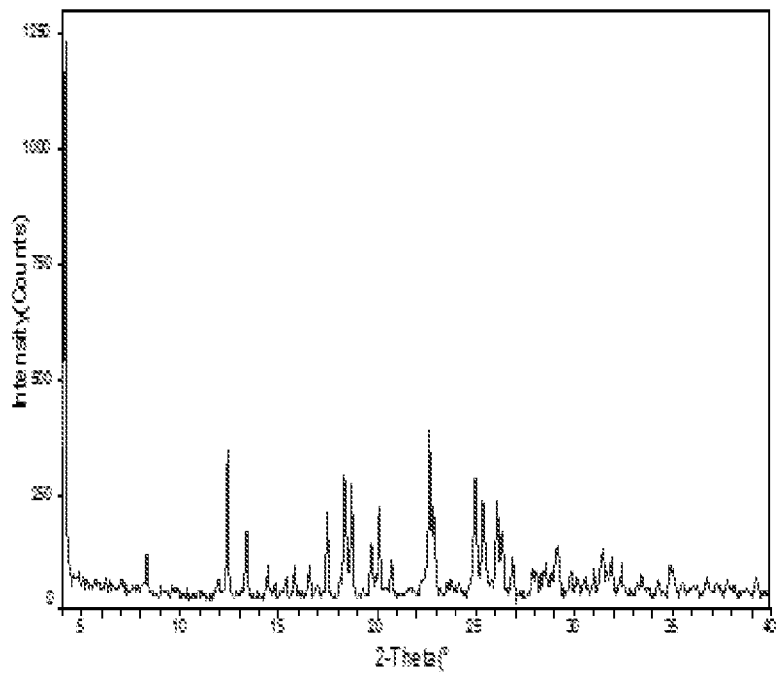
FIG. 2A is the X-ray powder diffraction pattern of crystal form B.
Figure 2B:
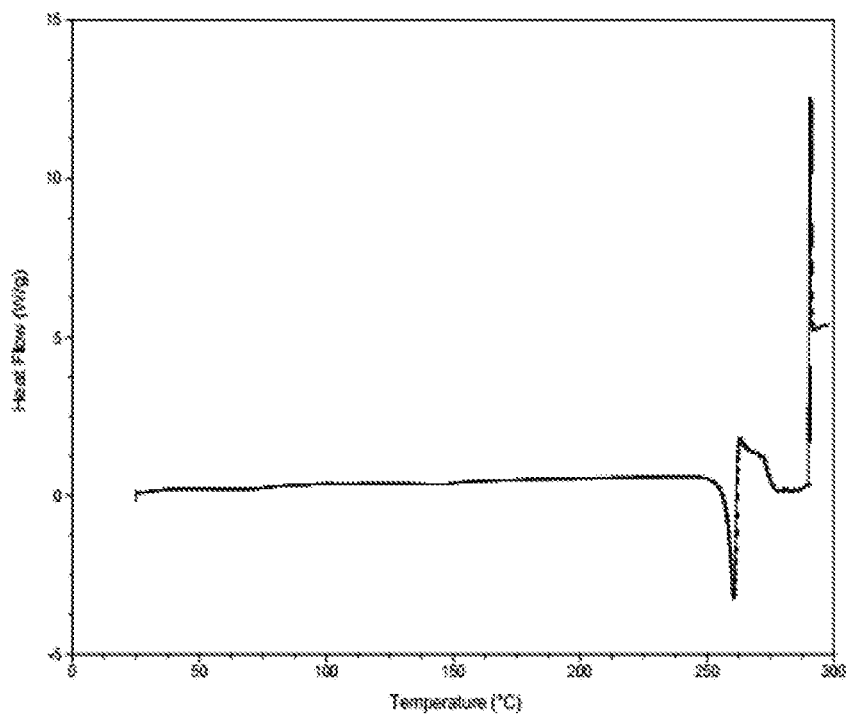
FIG. 2B is the differential scanning calorimetry analysis spectrum of crystal form B.

Example 10 Preparation of Crystal Form B of Compound of Formula X 100 mg of free base sample was weighed into a 20 ml glass sample bottle, 240 μL of 1M hydrobromic acid solution was added at 50° C., 1 mL of ethyl acetate was added, and the mixture reacted at this temperature for 4 h, the solution was turbid; slowly cooled to 0° C. after 4 hours, the solid precipitation increased and was obtained by centrifugation. After the solvent was evaporated, a solid product was obtained. The X-ray powder diffraction pattern of the obtained crystal is shown in FIG. 2A (2θ angle has been marked), and the DSC pattern is characterized as shown in FIG. 2B. The melting point is 253.89° C.-258.89° C. The crystal form is defined as crystal form B in the present application.

Figure 3A:
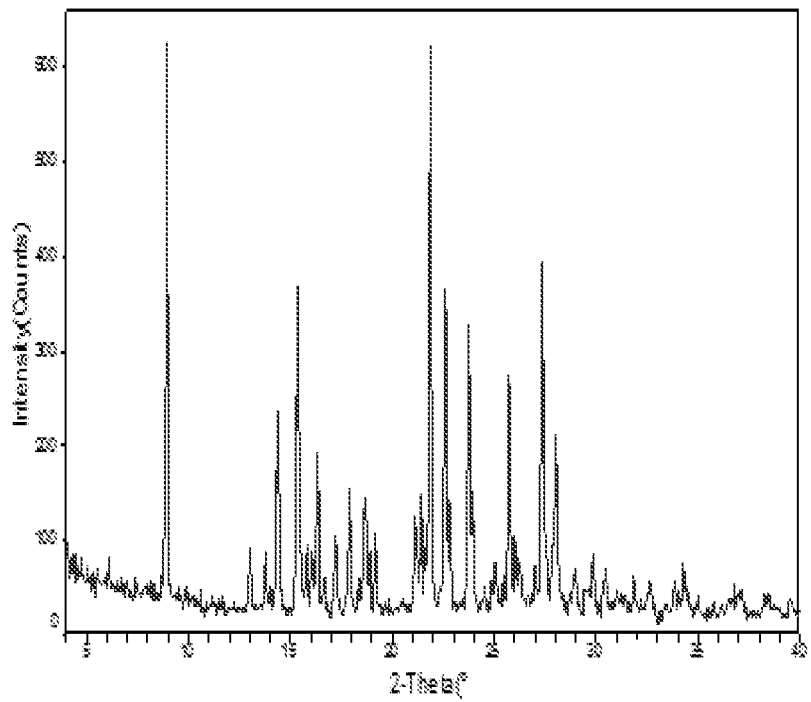
FIG. 3A is the X-ray powder diffraction pattern of crystal form C.
Figure 3B:
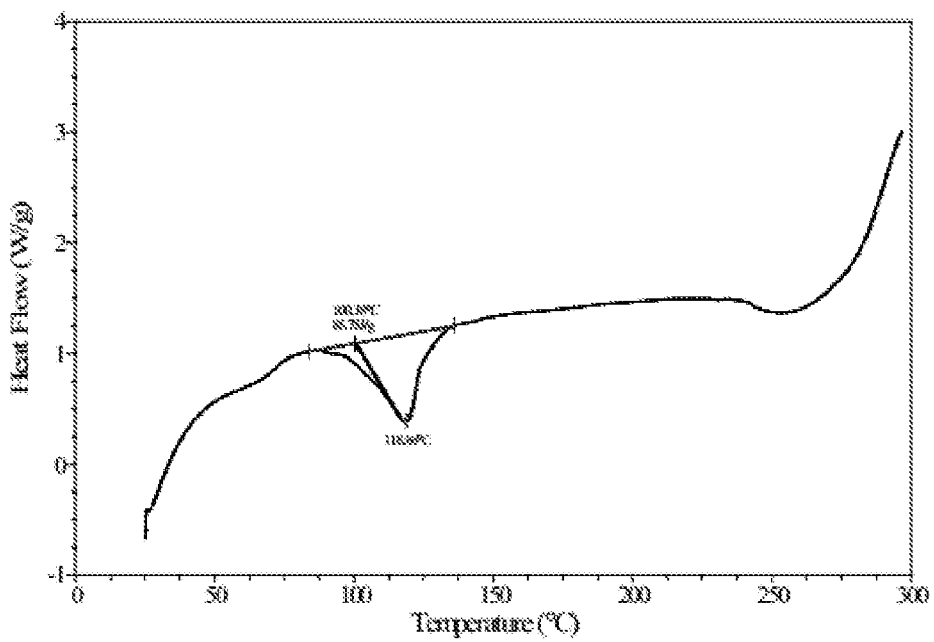
FIG. 3B is the differential scanning calorimetry analysis spectrum of crystal form C.
Figure 3C:
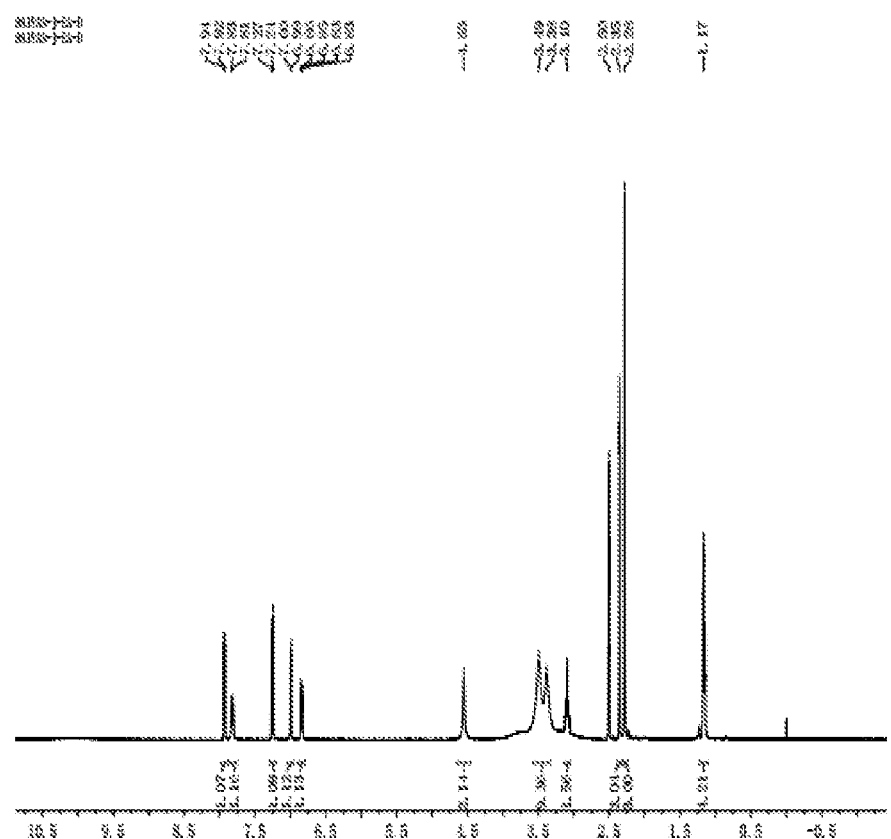
FIG. 3C is the $^1$H NMR spectrum of crystal form C.

Example 11 Preparation of Crystal Form C of Compound of Formula X 100 mg of free base sample was weighed into a 20 ml glass sample bottle, 240 μL of 1M methanesulfonic acid solution was added at 50° C., 1 mL of ethyl acetate was added, and the mixture reacted at this temperature for 4 h, the solution was turbid; slowly cooled to 0° C. after 4 hours, the solid precipitation increased and was obtained by centrifugation. After the solvent was evaporated, a solid product was obtained. The X-ray powder diffraction pattern of the obtained crystal is shown in FIG. 3A (2θ angle has been marked), and the DSC pattern is characterized as shown in FIG. 3B. The ¹HNMR spectrum is as shown in FIG. 3C, the melting point is 97.89° C.-103.89° C. The crystal form is defined as crystal form C in the present application.

Figure 4A:
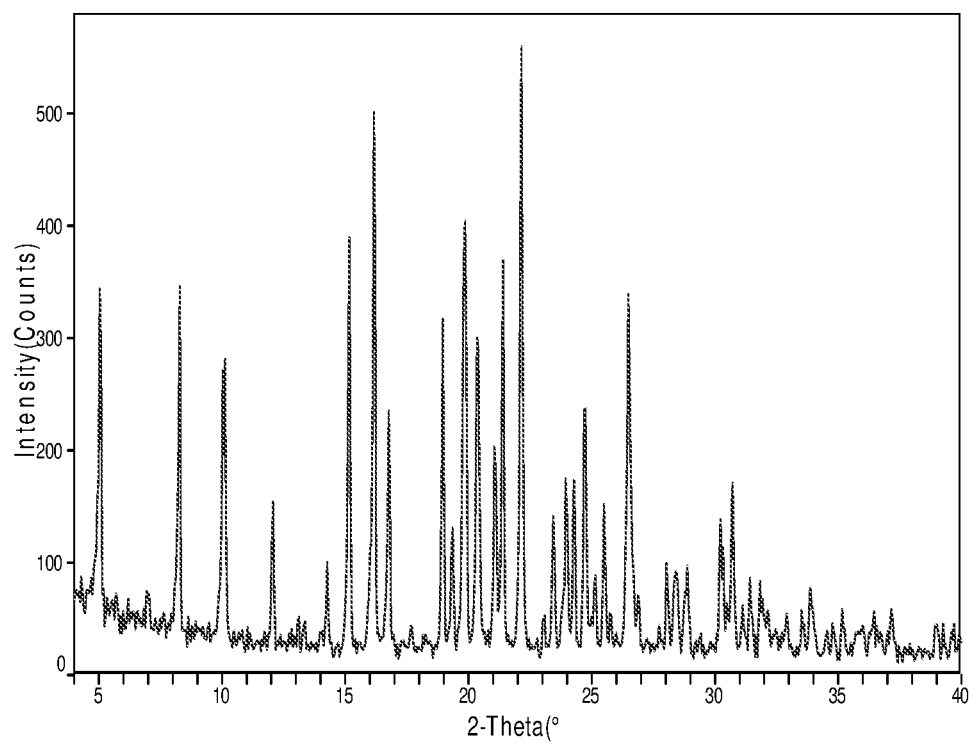
FIG. 4A is the X-ray powder diffraction pattern of crystal form D.
Figure 4B:
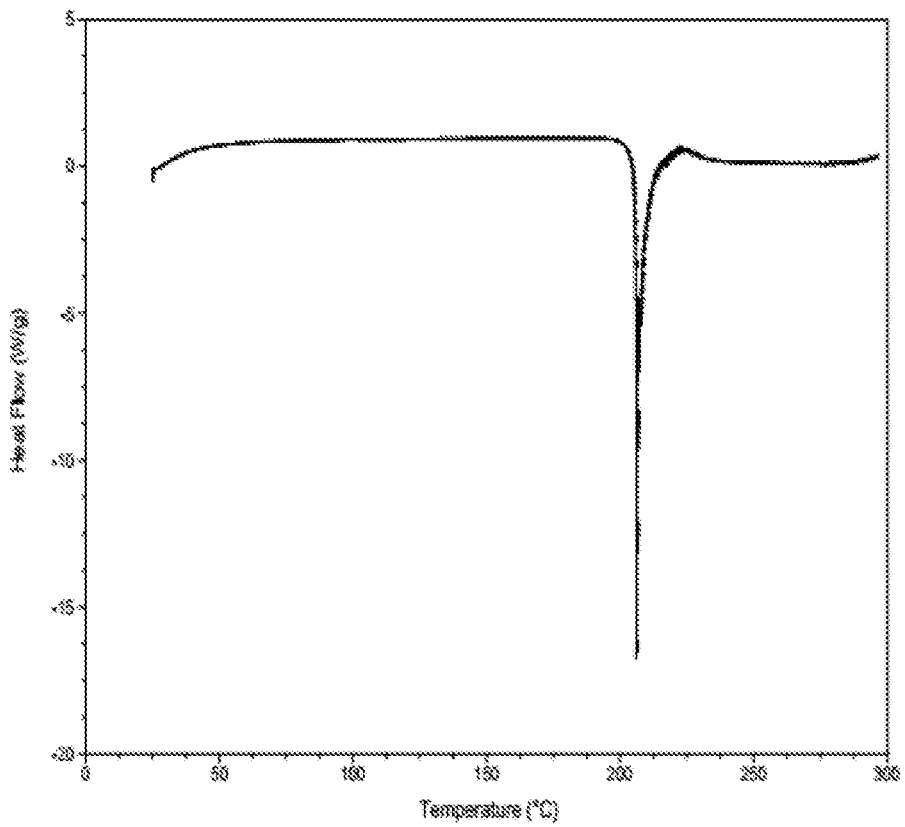
FIG. 4B is the differential scanning calorimetry analysis spectrum of crystal form D.
Figure 4C:
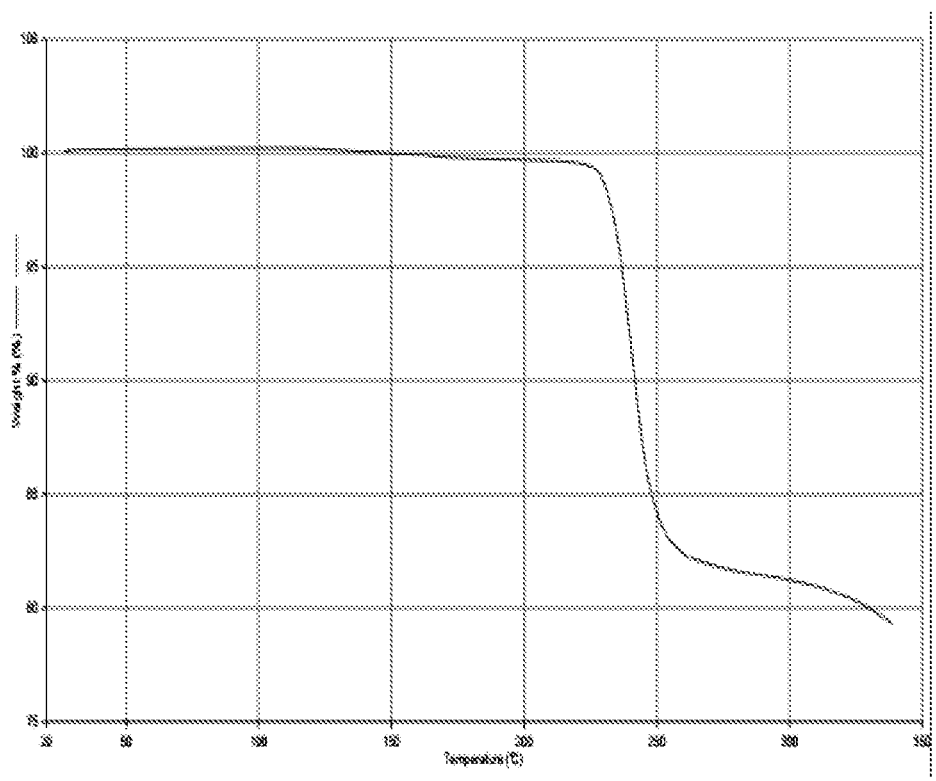
FIG. 4C is the thermogravimetric analysis spectrum of crystal form D.
Figure 4D:
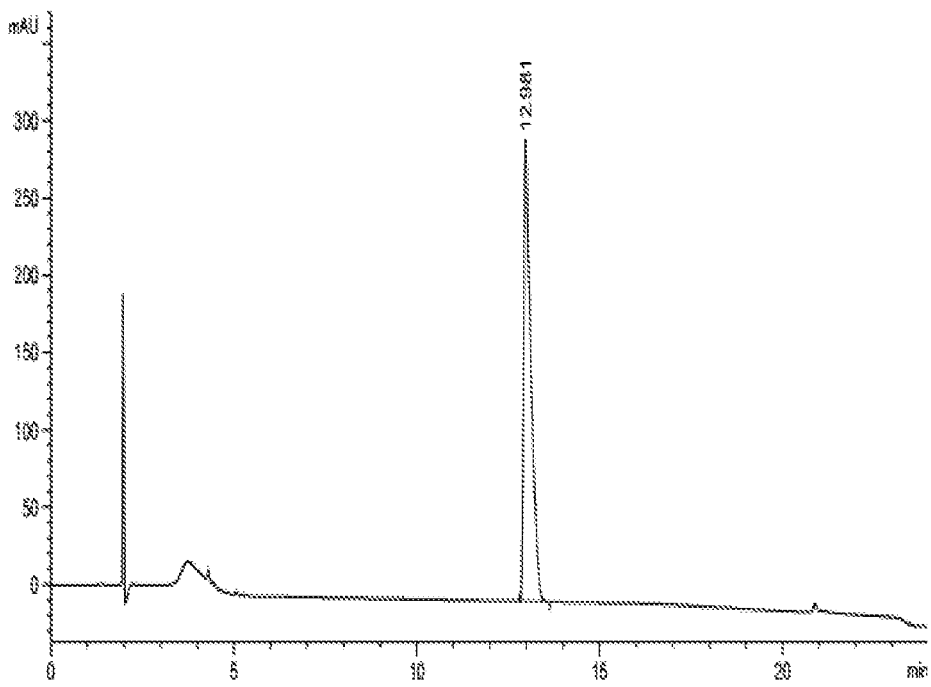
FIG. 4D is the HPLC spectrum of crystal form D.
Figures 4E, 4F:
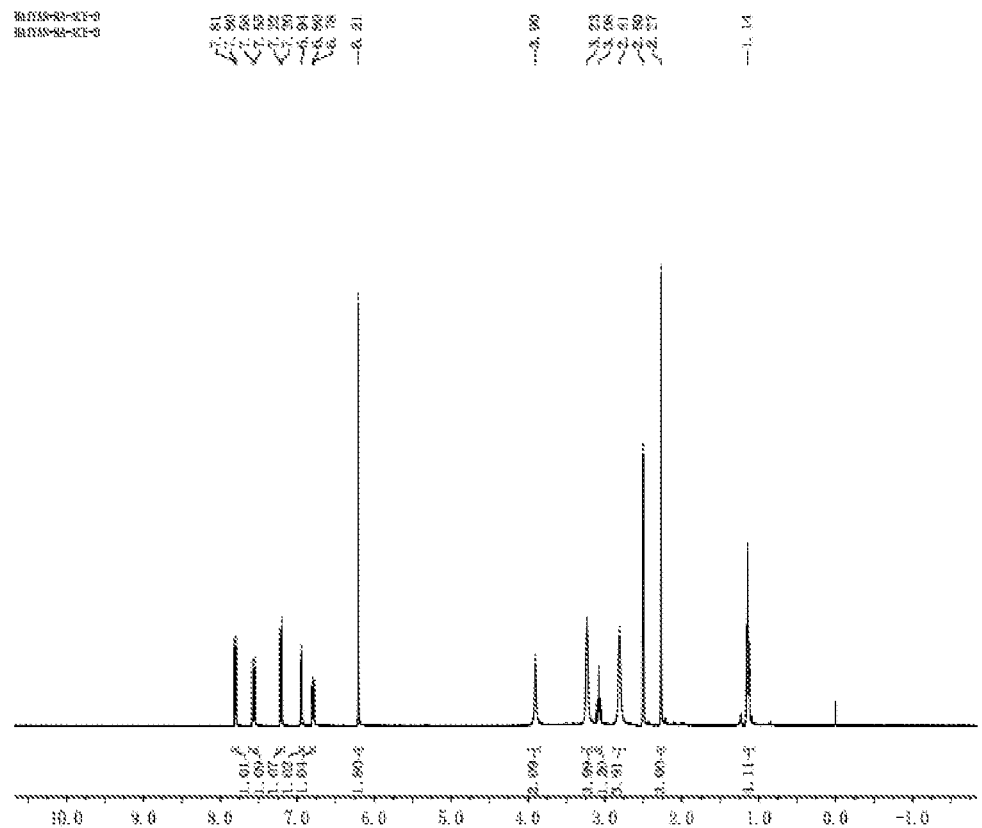
FIG. 4E is the $^1$H NMR spectrum of crystal form D.
FIG. 4F is the DVS curve of crystal form D.

Example 12 Preparation of Crystal Form D of Compound of Formula X 100 mg of free base sample was weighed into a 20 ml glass sample bottle, 1 mL of acetone was added, 240 μL of 1M maleic acid solution was slowly added while stirring at 50° C., the solution became turbid after a few minutes, and the mixture reacted at this temperature for 4 h, slowly cooled to 0° C. after 4 hours, the solid precipitation increased and was obtained by centrifugation. After the solvent was evaporated, a solid product was obtained. The X-ray powder diffraction pattern of the obtained crystal is shown in FIG. 4A (2θ angle has been marked), and the DSC/TGA pattern are characterized as shown in FIGS. 4B and 4C. The weight loss of the sample is 0.174% below 100° C., and there is an endothermic peak in the DSC pattern of the sample. The peak temperature is 206.06° C. HPLC is shown in FIG. 4D; the molar ratio of acid to base is 1:1, the ¹HNMR spectrum is as shown in FIG. 4E, and the melting point is 203.89° C.-207.89° C. The crystal form is defined as crystal form D in the present application.

Figure 7A:
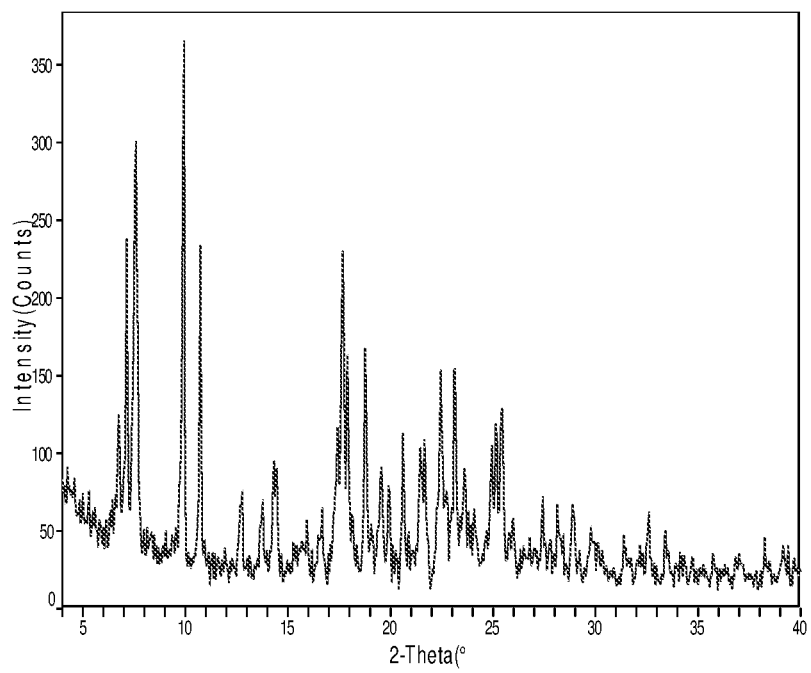
FIG. 7A is the X-ray powder diffraction pattern of crystal form E-3.
Figure 7B:
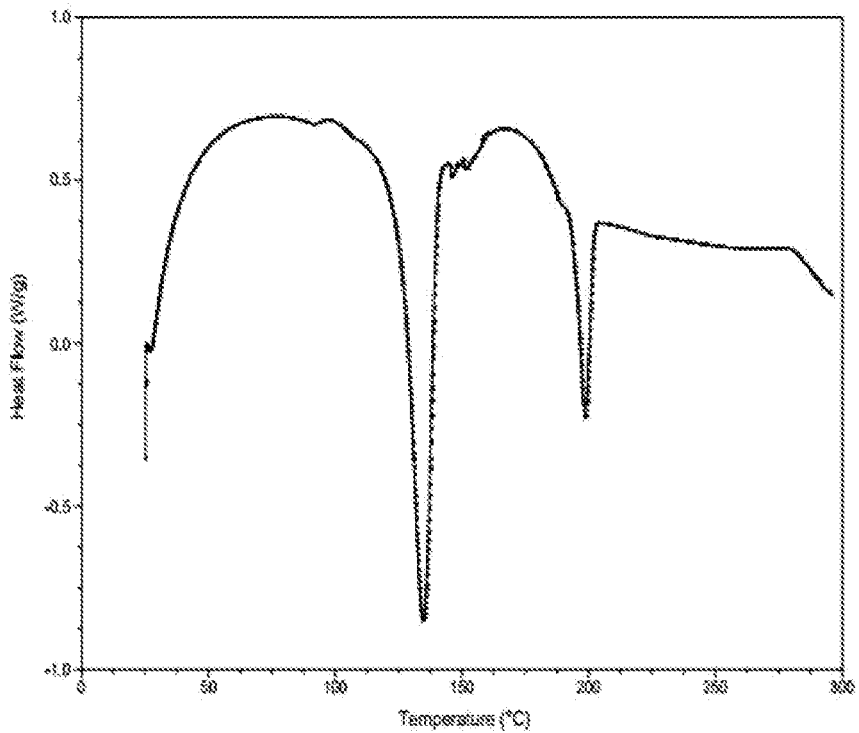
FIG. 7B is the differential scanning calorimetry analysis spectrum of crystal form E-3.
Figure 7C:
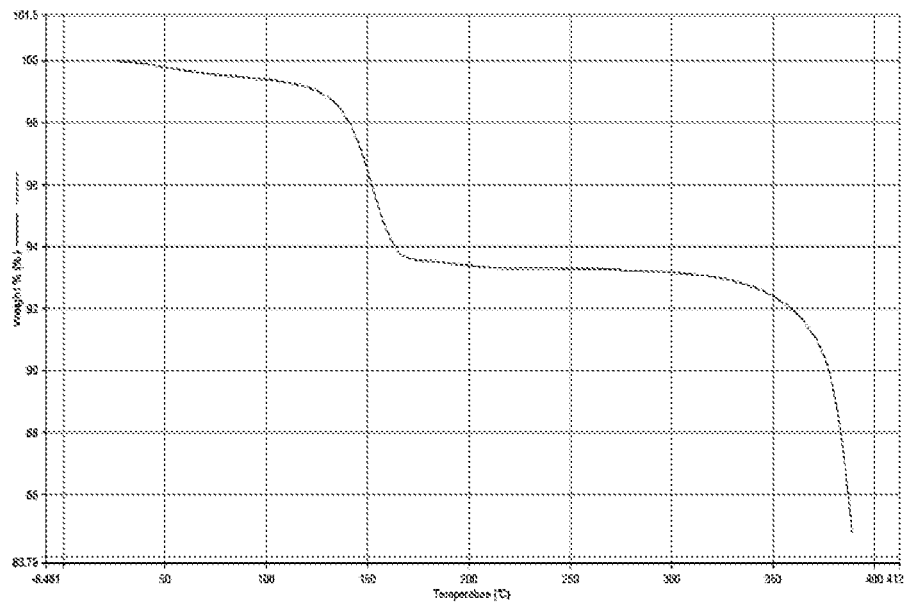
FIG. 7C is the thermogravimetric analysis spectrum of crystal form E-3.
Figure 7D:
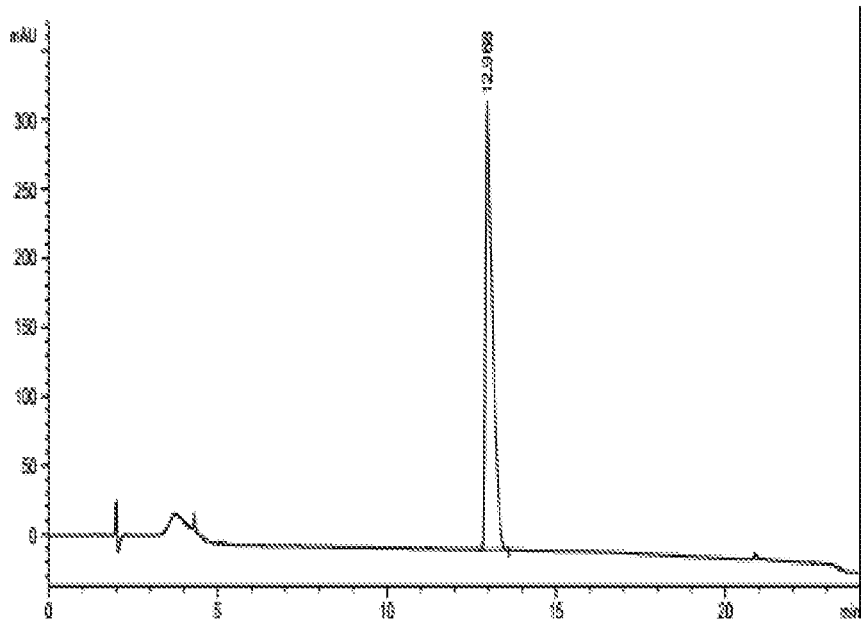
FIG. 7D is the HPLC spectrum of crystal form E-3.
Figure 7E:
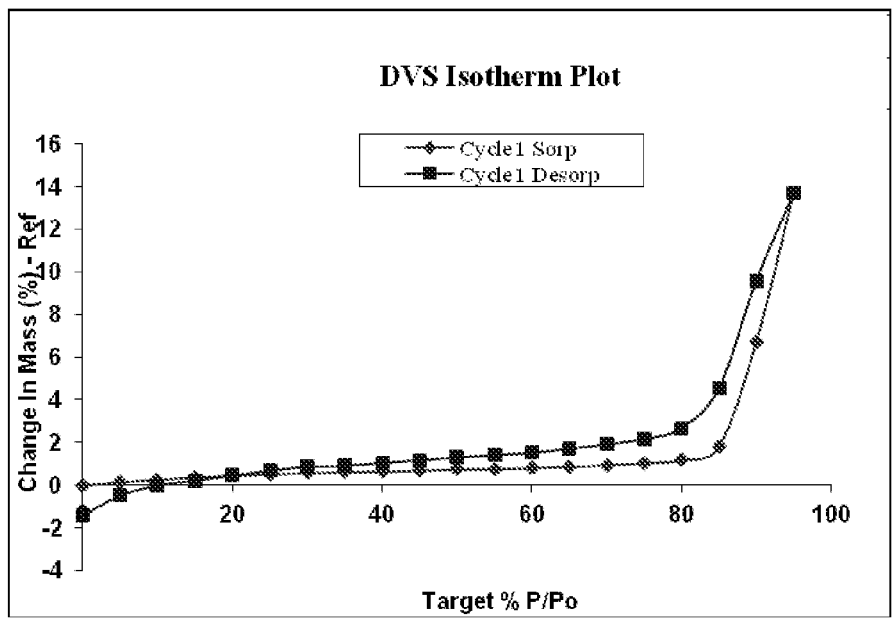
FIG. 7E is the DVS curve of crystal form E-3.

Example 13 Preparation of Crystal Form E-3 of Compound of Formula X 100 mg of free base sample was weighed into a 20 ml glass sample bottle, 1 mL of acetonitrile was added, 240 μL of 1M sodium hydroxide solution was slowly added while stirring at 50° C., the solution is clarified, the mixture reacted at this temperature for 4 h, and placed in a fume hood for solvent evaporation, or the mixture was first concentrated and then placed in a fume hood for solvent evaporation if there were more solvents. The X-ray powder diffraction pattern of the obtained crystal is shown in FIG. 7A (2θ angle has been marked), and the DSC/TGA pattern are characterized as shown in FIGS. 7B and 7C. The weight loss of the sample is 0.856% below 100° C., and there are two endothermic peaks in the DSC pattern of the sample, and the peak temperature are 134.50° C. and 198.38° C. respectively. HPLC is shown in FIG. 7D; the ratio of the salt is 1:0.78. The crystal form is defined as crystal form E-3 in the present application.

Figure 8A:
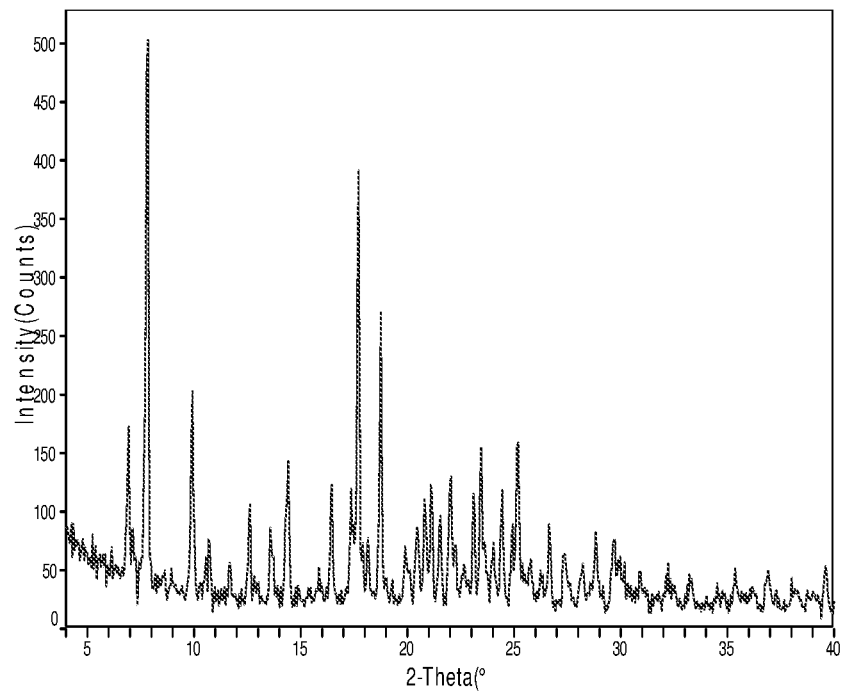
FIG. 8A is the X-ray powder diffraction pattern of crystal form F.
Figure 8B:
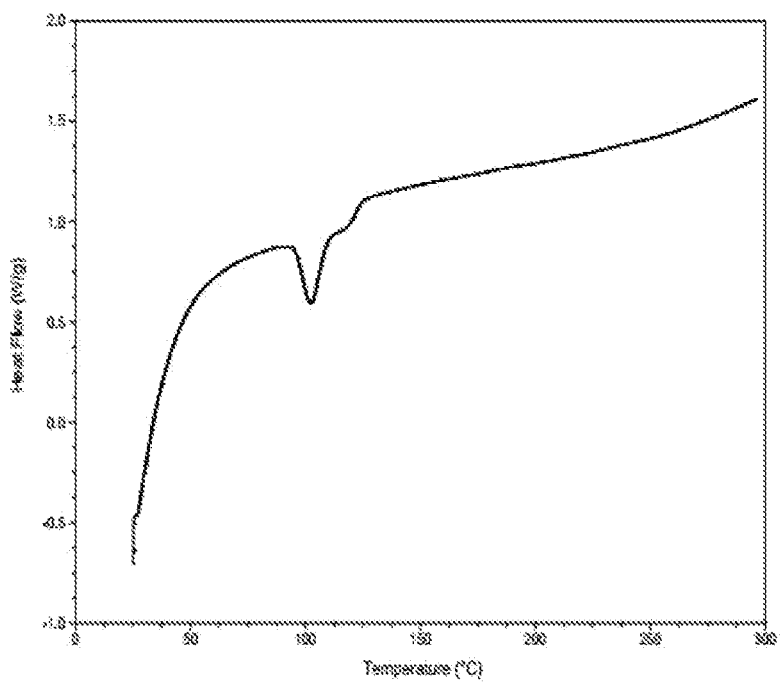
FIG. 8B is the differential scanning calorimetry analysis spectrum of crystal form F.
Figure 8C:
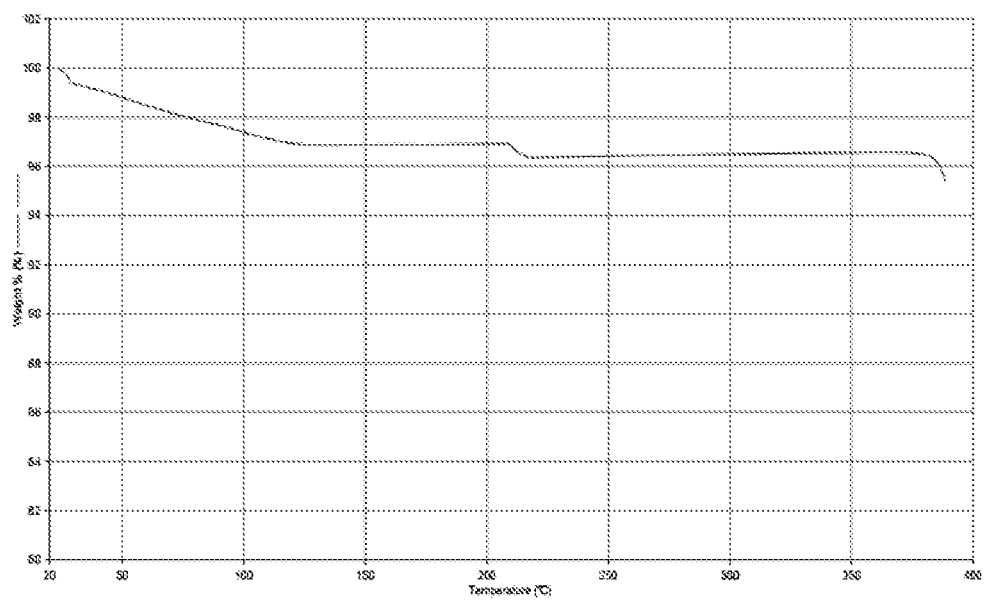
FIG. 8C is the thermogravimetric analysis spectrum of crystal form F.
Figure 8D:
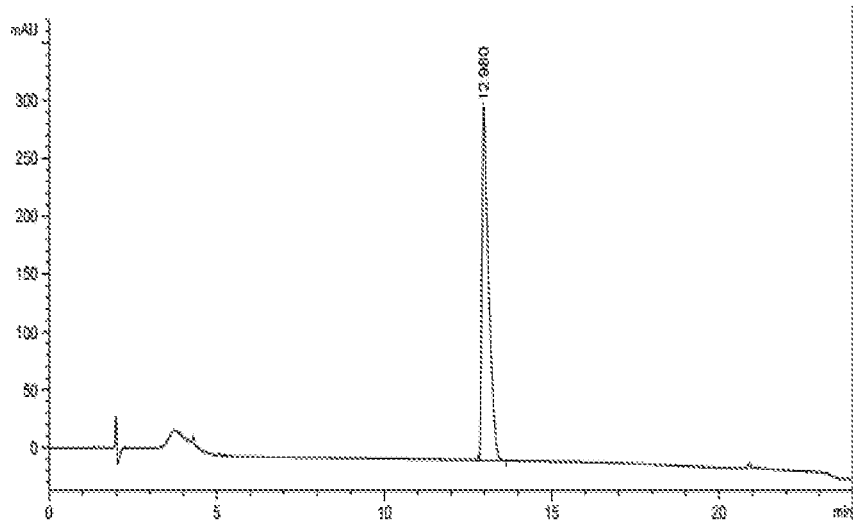
FIG. 8D is the HPLC spectrum of crystal form F.
Figure 8E:
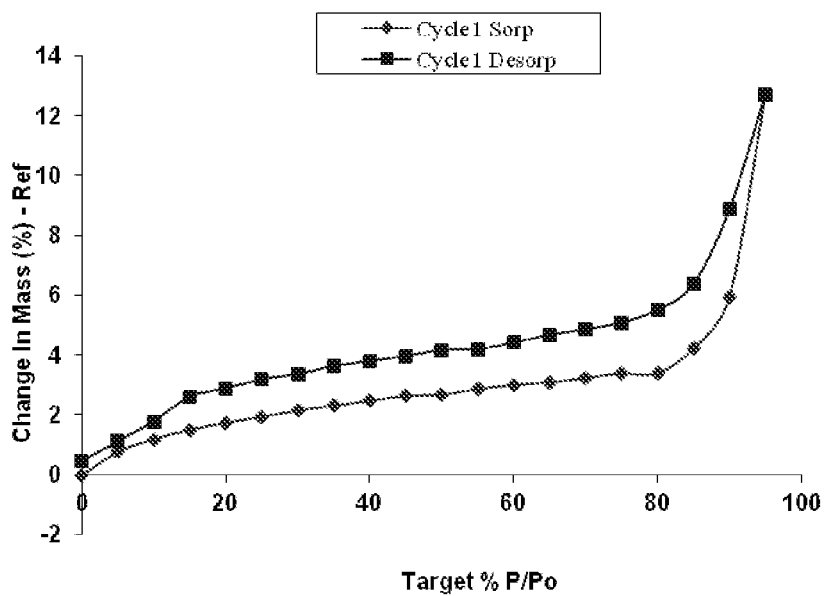
FIG. 8E is the DVS curve of crystal form F.

Example 14 Preparation of Crystal Form F of Compound of Formula X 100 mg of free base sample was weighed into a 20 ml glass sample bottle, 1 mL of methanol was added, 240 μL of 1M potassium hydroxide solution was slowly added while stirring at 50° C., the solution became turbid after a few minutes, and the mixture reacted at this temperature for 4 h, slowly cooled to 0° C. after 4 hours, the solid precipitation increased and was obtained by centrifugation. After the solvent was evaporated, a solid product was obtained. The X-ray powder diffraction pattern of the obtained crystal is shown in FIG. 8A (2θ angle has been marked), and the DSC/TGA patterns are characterized as shown in FIGS. 8B and 8C. The weight loss of the sample is 3.029% below 100° C., and there is an endothermic peak in the DSC pattern of the sample. The peak temperature is 102.75° C. HPLC is shown in FIG. 8D; the ratio of the salt is 1:0.67, and the melting point is 100.89° C. -104.89° C. The crystal form is defined as crystal form F in the present application.

Example 15 Method for Preparing Various Crystal Forms of the Salts of Compound of Formula X 800 mg of free base sample was weighed, and 32 ml of tetrahydrofuran was added, the mixture was dissolved by ultrasonication to prepare a 25 mg/ml solution, from which 0.8 ml was taken into a 1.5 ml sample vial, and the solvent was removed by nitrogen blowing instrument, the corresponding acid or base was added in a 1.2:1 molar ratio of acid to free base, and then 1 ml of the corresponding solvent was added, the solution was heated under ultrasound to be clarified, and the mixture reacted at 50° C. for 4 h, and then slowly cooled to precipitate a solid, and the solid was collected by centrifugation. Tried to induce crystallization from the clear solution by anti-solvent addition, the resulting solid was evaporated to dryness and used for XRPD test. The results of various salts formed by acid are shown in Table 26 below:

TABLE 26

| | Solvent | | | |
|---|---|---|---|---|
| Acid or base | methanol | ethyl acetate | acetonitrile | acetone |
| Hydrochloric acid | hydrochloride | hydrochloride | hydrochloride | hydrochloride |
| Sulfuric acid | free base | free base | free base | free base |
| Hydrobromic acid | hydrobromide | hydrobromide | hydrobromide | hydrobromide |
| Phosphoric acid | free base | free base | free base | free base |
| Methanesulfonic acid | free base | methanesulfonate | free base | free base |
| Maleic acid | free base | free base | free base | maleate |
| L-tartaric acid | free base | free base | free base | free base |
| Citric acid | free base | free base | free base | free base |
| Fumaric acid | free base | free base | free base | free base |
| NaOH | N/A | sodium salt | sodium salt | N/A |
| KOH | potassium salt | potassium salt | potassium salt | potassium salt |

The results showed that the free base sample formed salts only with hydrochloric acid, hydrobromic acid, methanesulfonic acid and maleic acid, and the free base sample did not form salt with methanesulfonic acid in methanol, acetonitrile and acetone, and did not form salt with maleic acid in methanol, ethyl acetate and acetonitrile, and did not form salt with NaOH in methanol and acetone.

Example 16 Stability Experiment 90 mg of crystal form A, D, E-3 and F was weighed respectively, and stored at 60° C./70% RH and 40° C./70% RH. Another set of samples were sealed at 5° C. and kept as a control at the same time. The changes in crystal form and purity were measured on the $7^{th}$ day and the $21^{st}$ day respectively. The results are shown in Table 27 below, the four crystal forms have good stability at 60° C. and the crystal forms have not changed.

Example 17 Hygroscopicity Experiment

The DVS results for crystal forms A, D, E-3 and F are shown in FIG. 1E, FIG. 4F, FIG. 7E and FIG. 8E, respectively. The crystal form A absorbs 0.4% moisture at 95% RH and is slightly hygroscopic; the crystal form D absorbs 0.07% moisture at 95% RH and has almost no hygroscopicity; the crystal form F absorbs 4% moisture when RH is 85%, and therefore has hygroscopicity; the crystal form E-3 absorbs 2% moisture when RH is 85%, and therefore has hygroscopicity.

Example 18 Solubility Experiment

The solubility of crystal forms A, D, E-1, E-3, F and free base sample in buffer of 0.1M HCl, pH 4.5, pH 6.8 and water was tested at room temperature. In the test, the standard curves of free base sample and five crystal forms were

TABLE 27

Stability data for four crystal forms

| Crystal form | Condition for storage | RRT (%) | | | | | | Total impurities (%) | Content (%) | Characters |
|---|---|---|---|---|---|---|---|---|---|---|
| | | 0.54 | 0.79 | 0.86 | 0.88 | 1.00 | 1.05 | | | |
| E-3 | 5° C. 0 d | 0.13 | — | 0.08 | — | 99.79 | 0.06 | 0.26 | NA | light yellow powder |
| F | | — | 0.06 | 0.05 | — | 99.86 | 0.03 | 0.14 | NA | white or off-white powder |
| A | | — | 0.07 | 0.05 | — | 99.84 | 0.04 | 0.16 | NA | white or off-white powder |
| D | | — | 0.04 | 0.03 | — | 99.90 | 0.03 | 0.11 | NA | white or off-white powder |
| E-3 | 60° C. 7 d | 0.09 | — | 0.08 | — | 99.78 | 0.06 | 0.22 | 99.5 | light yellow powder |
| F | | — | 0.06 | 0.03 | — | 99.87 | 0.04 | 0.13 | 99.7 | white or off-white powder |
| A | | — | 0.08 | 0.05 | — | 99.84 | 0.02 | 0.16 | 98.6 | white or off-white powder |
| D | | — | 0.04 | 0.03 | — | 99.90 | 0.03 | 0.11 | 98.9 | white or off-white powder |
| E-3 | 60° C. 21 d | 0.08 | — | 0.07 | — | 99.71 | 0.04 | 0.30 | 105.1 | light yellow powder |
| F | | — | 0.05 | 0.03 | 0.02 | 99.80 | 0.03 | 0.20 | 101.0 | white or off-white powder |
| A | | — | 0.07 | 0.02 | 0.05 | 99.82 | 0.03 | 0.18 | 97.6 | white or off-white powder |
| D | | — | 0.04 | — | 0.02 | 99.91 | 0.03 | 0.09 | 99.1 | white or off-white powder |
| E-3 | 40° C. 75% RH 14 d | 0.09 | — | 0.07 | — | 99.71 | 0.04 | 0.29 | 106.4 | yellow particles |
| F | | — | 0.04 | — | — | 99.90 | 0.04 | 0.10 | 98.4 | transparent particles |
| A | | — | 0.07 | — | 0.04 | 99.83 | 0.02 | 0.17 | 99.8 | white or off-white powder |
| D | | — | 0.04 | — | 0.02 | 99.90 | 0.03 | 0.09 | 100.2 | white or off-white powder |

—: below detection limit;
NA: do not test plotted. Subsequently, 6 mg of API and five crystal form samples were weighed, respectively, and 2 ml of the solvent was added, the mixture was shaken at room temperature for 4 h, then ultrasonicated for 30 min, centrifuged, and the supernatant was taken out, filtered through a 0.45 μm filter and injected, and the solubility was measured, the results are shown in Table 28 (concentration is in mg/ml).

TABLE 28

| Crystal form | Solubility (mg/mL) | | | |
|---|---|---|---|---|
| | pH4.5 | pH6.8 | 0.1M HCl | $H_2O$ |
| free base sample | 0.001 | 0.021 | 0.065 | 0.027 |
| crystal form A | 0.001 | 0.01 | 0.011 | 0.005 |
| crystal form D | 0.002 | 0.016 | 0.018 | 0.005 |
| crystal form F | 0.002 | 0.050 | 0.017 | >3.154 |
| crystal form E-3 | 0.002 | 0.096 | 0.016 | >2.780 |
| crystal form E-1 | 0.002 | 0.035 | 0.019 | >2.669 |

The solubility of five crystal forms in pH 4.5, pH 6.8, 0.1 M HCl was not significantly different from that of the free base sample, and the solubility of crystal forms E-1, E-3 and F in water was significantly improved, and was above 2.7 mg/ml.

Example 19 Pharmaceutical Composition

Tablets of the hydrobromide of compound of formula X were prepared from the components shown in Table 29 below:

TABLE 29

| hydrobromide of compound of formula X (Example 15) | 20 g |
|---|---|
| starch | 40 g |
| lactose | 32 g |
| PVP | 3 g |
| sodium carboxymethyl starch | 3 g |
| sodium dodecyl sulfate | 1 g |
| magnesium stearate | 1 g |

The hydrobromide of compound of formula X and starch are mixed and sieved, then well mixed with the above other components, and directly compressed into tablets according to a conventional method.

Example 20 Pharmaceutical Composition

Tablets of the crystal form A were prepared from the components shown in Table 30 below:

TABLE 30

| crystal form A | 15 g |
|---|---|
| starch | 40 g |
| lactose | 37 g |
| PVP | 3 g |
| sodium carboxymethyl starch | 3 g |
| sodium dodecyl sulfate | 1 g |
| magnesium stearate | 1 g |

The crystal form A and starch are mixed and sieved, then well mixed with the above other components, and directly compressed into tablets according to a conventional method.

Example 21 Pharmaceutical Composition

Capsules of crystal form I were prepared from the components shown in Table 31 below:

TABLE 31

| crystal form I | 20 g |
|---|---|
| starch | 40 g |
| lactose | 32 g |
| PVP | 3 g |
| sodium carboxymethyl starch | 3 g |
| sodium dodecyl sulfate | 1 g |
| magnesium stearate | 1 g |

The crystal form I and starch are mixed and sieved, and then well mixed with the above other components, and filled into ordinary gelatin capsules according to a conventional method.

COMPARATIVE EXAMPLES

The following comparative examples can be prepared by a similar method to the compound of formula X, and the structures are shown in Table 32 below.

TABLE 32

| Comparative example | |
|---|---|

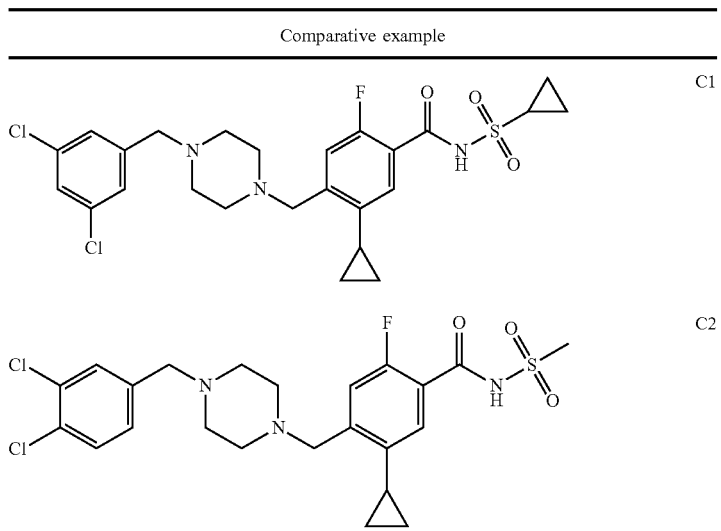

TABLE 32-continued
Comparative example
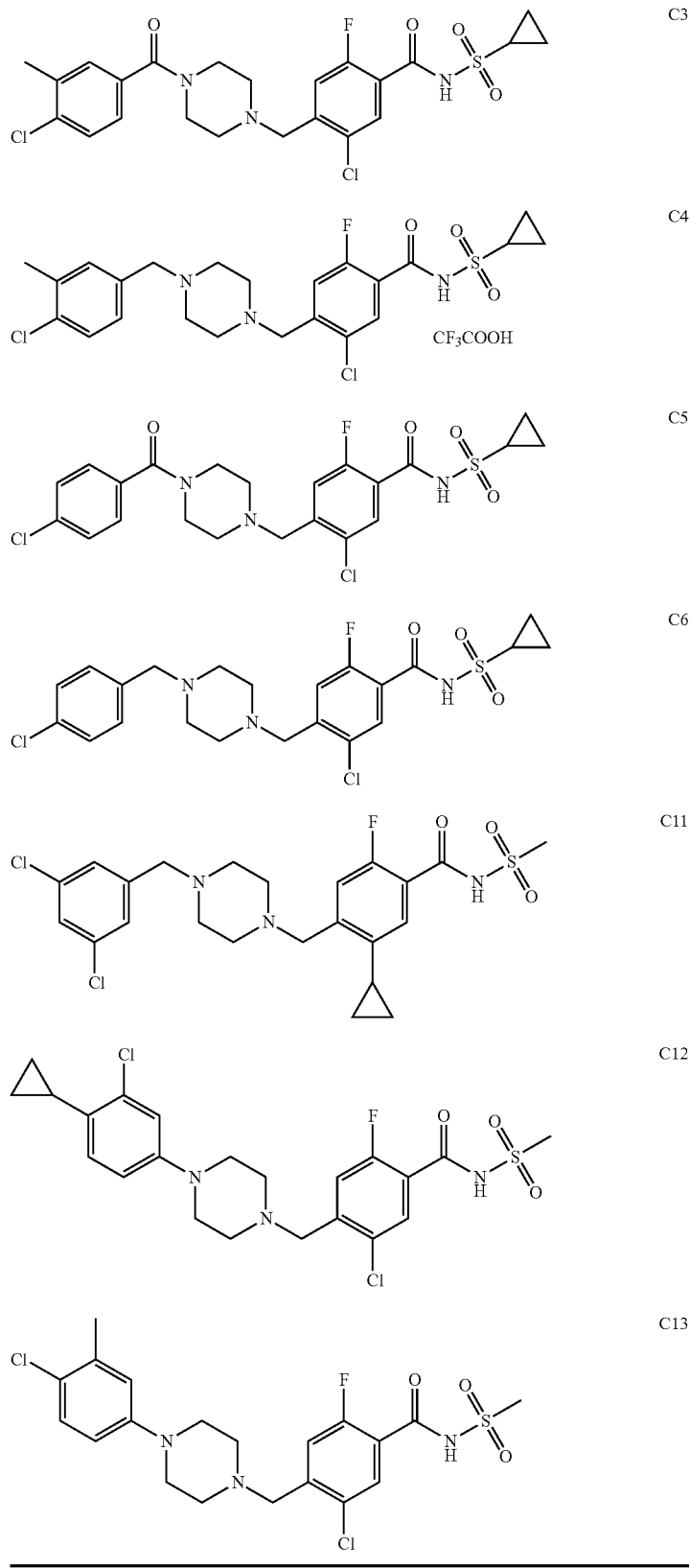
C3
C4
C5
C6
C11
C12
C13

Test Example 1: Manual Patch Clamp Experiments of hNav1.7 and hNav1.5 Channels Patch voltage clamp electrophysiology allows for the direct measurement and quantification of current block of voltage-gated sodium channels (NaV's), and allows the determination of the time and voltage-dependence of block which has been interpreted as differential binding to the resting, open and inactivated states of the sodium channel to reflect the compound's inhibitory or activating effects (Hille, B., Journal of General Physiology (1977), 69: 497-515).

Representative compounds of the present disclosure were performed using a manual patch clamp experiment and the purpose of this study was to test the effect of compounds on this ion channel current on a stable cell line transfected with a specific ion channel using a manual patch clamp method, the used stable cell lines CHO-hNav1.7 and HEK-hNav1.5 were from Genionics and WuXi Apptec (Shanghai) respectively.

Manual patch clamp experimental program is as follows:

(1) Preparation of solutions and compounds: The whole cell patch clamp technique was used to record hNav1.7 and hNav1.5 currents. In the experiment, the composition of extracellular fluid (mM): HEPES: 5, NaCl: 40, KCl: CaCl$_2$: 1, MgCl$_2$:1, CdCl$_2$:0.1, TEA-Cl: 20. The pH was adjusted to 7.3 with NaOH and the osmotic pressure was adjusted to 310-320 mOsm with sucrose, filtered and stored at 4° C. The composition of the intracellular fluid (mM): HEPES: 10, NaCl: 10, CsOH: 5, CsF: 140, EGTA: 1. The pH was adjusted to 7.3 with CsOH and the osmotic pressure was adjusted to 280-290 mOsm with sucrose, filtered and stored at −20° C.

The positive control and the test compound were firstly dissolved in 100% DMSO (Sigma-Aldrich, D2650), configured as stock solution at a concentration (100 nM, 1000 nM).) The above stock solution was serially diluted with DMSO prior to the experiment, the solution was further diluted with extracellular solution to obtain the desired concentration of the test solution. The final concentration of DMSO in extracellular fluid did not exceed 0.30%.

(2) Manual Patch Clamp Experiment: The cell suspension was added to a 35 mm petri dish and placed on an inverted microscope stage, the cells were perfused with an extracellular fluid and the flow rate was 1-2 mL/min after cell adherence. The glass microelectrode was pulled in two steps by a microelectrode puller with an inlet water resistance of 2-5 MΩ. A/D-D/A digital-analog conversion was performed by Digidata 1440 (Molecular Devices) and pCLAMP software (version 10.2, Molecular Devices) for stimulation and signal acquisition; the signal was amplified by patch clamp amplifier (Multiclamp 700B, Molecular Devices), filtering is 4 KHz.

Two different voltage stimulation procedures were used in the hNav1.7 and hNav1.5 manual patch clamp experiments.

One is the inactivation stimulation program, the clamp potential is set at $V_{1/2}$ of the corresponding channel, ie about 50% of the channels are inactivated, then the voltage is applied to −120 mV for 50 ms, then depolarized to −10 mV for 20 ms leading to sodium current, and finally back to the clamp potential. This stimulation program can also be called channel state-dependent voltage stimulation program.

The other is the non-inactivation stimulation program, the clamp potential is maintained at −120 mV, voltage stimulation is given to −10 mV for 20 ms leading to sodium current, and finally back to the clamp potential. That is all channels have not experienced inactivation status, but activate directly from the resting state under the conditions of the stimulation program.

The time intervals of these two voltage stimulation program were 10 s. The inhibitory effect of the compound was calculated by the change of the current before and after dosing, the IC$_{50}$ value was fitted by the Hill equation. If the compound shows a multiple difference in channel effects at the above two different voltage stimulation, the compound is state-dependent on the channel. The results are shown in Table 33 and Table 34, respectively.

TABLE 33

Inhibition of Nav1.7 by the representative compounds of the present disclosure at two concentrations

| Compound | 100 nM(%) | 1000 nM(%) |
|---|---|---|
| the free base of formula X compound | 86.90 | 97.68 |
| C1 | 49.22 | 64.84 |
| C2 | 52.03 | 64.05 |
| C3 | 17.56 | 52.26 |
| C4 | 18.58 | 58.91 |
| C5 | 17.19 | 36.76 |
| C6 | 11.15 | 67.25 |
| C11 | 23.06 | 51.85 |

TABLE 34

Selectivity for other ion channels

| Compound | the free base of formula X compound | Compound | the free base of formula X compound |
|---|---|---|---|
| Nav1.7(IC$_{50}$/nM) | 24.57 | Nav1.2(IC$_{50}$/nM) | 9600 |
| Nav1.5(IC$_{50}$/nM) | 6160 | Nav1.8(IC$_{50}$/nM) | 18900 |
| hERG potassium ion channel (IC$_{50}$/nM) | >10000 | | |

As can be seen from Table 33, the free base of formula X compound of the present disclosure have a higher inhibitory activity against Nav1 7. In addition, it was found that the direct attachment of the nitrogen atoms on the six-membered (piperazine) nitrogen-containing heterocycles to the carbon atoms on benzene or pyridine ring has a significant effect on the inhibitory activity against Nav1.7. Studies have shown that when the nitrogen atom is not directly linked to benzene or pyridine ring, that is the benzene or pyridine ring is connected to the nitrogen atom via a methylene or carbonyl group and the like, the inhibitory activity is significantly reduced. In addition, if the benzene or pyridine ring is connected to the nitrogen atom via a methylene or carbonyl group and the like and R$_6$ is a methyl, the inhibitory activity is significantly reduced.

Test Example 2: Effect on the hERG Potassium Ion Channel 2.1 Cell Culture 2.1.1 Cells used in this experiment are CHO cell lines (supplied by Sophion Bioscience, Denmark) which are hERG cDNA transfectant and stably express hERG channels, cell progeny is P15. Cells are cultured in medium containing the following ingredients Invitrogen): Ham's F12 medium, 10% (v/v) inactivated fetal bovine serum, 100 μl/ml hygromycin B, 100 μl/ml Geneticin.

2.1.2 CHO hERG cells were grown in Petri dishes containing the above medium and cultured in an incubator containing 5% $CO_2$ at 37° C. CHO hERG cells were transferred onto round glass plates in Petri dishes, and grown on the same culture medium and culture conditions as above 24 h to 48 h prior to the electrophysiological experiments, and the density of CHO hERG cells on each round glass plate needs to meet the requirements that the vast majority of cells are independent and individual.

2.2 Experimental Solution

The following solutions (supplied by Sophion) were used for electrophysiological recording. The reagents used in this test were provided by Sigma.

TABLE 35

Intracellular and extracellular fluid composition

| Reagents | Extracellular fluid (mM) | Intracellular fluid (mM) |
|---|---|---|
| $CaCl_2$ | 2 | 5.37 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| PH | 7.4(adjusted with NaOH) | 7.25(adjusted with KOH) |
| Osmotic pressure | Osmotic pressure around 305 mOsm | Osmotic pressure around 295 mOsm |

2.3 Electrophysiological Recording System

In this experiment, whole-cell current recording was performed using a manual patch clamp system (HEKA EPC-10 signal amplification and digital conversion system, purchased from HEKA Electronic, Germany). The round glass slide of which surface CHO hERG cells were grown on was placed in an electrophysiological recording slot under an inverted microscope. Perfused steadily with extracellular fluid in recording slot (approximately 1 ml per minute). A conventional whole-cell patch clamp current recording technique was used in the experiment. Unless otherwise specified, experiments were performed at normal room temperature (about 25° C.). Cell clamping was at −80 mV. Cell clamping voltage depolarized to +20 mV to activate hERG potassium channel, clamping to −50 mV after 5 sec to eliminate inactivation and generate tail currents. The tail current peak was used as a value for hERG current. The hERG potassium current recorded in the above steps could be superfused for test drug after the steady perfusion state of the extracellular fluid in the recording slot had been stabilized until the inhibition of the hERG current by the drug reached a steady state. The last coincidence of the three consecutive current recording lines was generally used as a criterion to determine whether the state is stable. After reaching a steady state, perfused with extracellular fluid until hERG current returned to the value before the drug adding. One or more drugs could be tested on a single cell, or multiple concentrations of the same drug, but needed to be rinsed with extracellular fluid between different drugs. Cisapride (purchased from Sigma) was used as a positive control in experiments to ensure that the quality of the used cells were normal.

2.4 Compound Treatment and Dilution

The compound was first dissolved in DMSO to a concentration of 10 mM and then the compound was diluted 1000-fold to the final 10 μM test concentration using an extracellular solution. The final concentration of DMSO in the compound test solution was equal to 0.1%. The test concentration of positive control cisapride was 0.1 μM. All stock solutions and test solutions were subjected to regular 5-10 minute sonication and shaking to ensure complete dissolution of the compound.

2.5 Data Analysis

The test data were analyzed by the data analysis software provided by HEKA Patchmaster (V2x73.2), Microsoft Excel and Graphpad Prism 5.0.

TABLE 36

Inhibition of hERG potassium ion channels by representative compounds of the present disclosure

| Compound | hERG inhibitory concentration IC50(μM) |
|---|---|
| the free base of formula X compound | >10 μM |

It can be seen from Table 36 that the free base of formula X compound have little inhibitory activity on the hERG potassium ion channel and thus have a selective inhibition on the potassium ion channel.

Test Example 3: Metabolism Stability Test

1. Preparation of Buffer

Buffer A: 1 L solution of 100 mM potassium dihydrogen phosphate containing 1 mM EDTA (Sigma, V900157-100G) was prepared.

Buffer B: 1 L solution of 100 mM dipotassium hydrogen phosphate containing 1 mM EDTA was prepared.

Buffer C: 700 mL of buffer B was taken out and titrated with buffer A to pH 7.4.

2. Preparation of the Compound to be Tested and the Positive Control Drug (Ketanserin (Sigma S006-10MG))

2.1 10 μl of 10 mM compound to be tested and 10 μl of 10 mM ketanserin were taken out and 190 μl of pure acetonitrile was added to each of them to prepare 500 μM compound to be tested and ketanserin, respectively.

2.2 20 μl (20 mg/mL) of liver microsomes (Corning Lot. NO. 4133007) stock solution was added to 513.4 μl of buffer C on wet ice. 0.75 mg/mL liver microsomal solution was obtained.

2.3 1.5 μl of each of the above-mentioned compound to be tested and ketanserin solution was added to 498.5 μl of liver microsomal solution (0.7 5 mg/mL) respectively on wet ice. 1.5 μM mixed solution of compound to be tested and 1.5 μM mixed solution of ketanserin were obtained.

2.4 At the time points 0, 5, 15, 30, 45, and 60 min, 30 μl of the mixed solution of compound to be tested and 30 μl of the mixed solution of ketanserin were dispensed into the reaction plate on wet ice, respectively.

2.5 5 mg reduced coenzyme II (Roche, 10621706001) was weighed and dissolved in 1 mL of buffer C. 6 mM reduced coenzyme II solution was obtained. The reduced coenzyme II solution was dispensed into the reaction plate.

2.6 Imipramine was dissolved to give a 10 mM solution. 10 μl imipramine solution was added to 100 mL of blank acetonitrile to generate the internal reference.

2.7 At 0 min, 135 μL of iced acetonitrile (Merck (Lot. 1778229518)) containing the internal reference was added to each well and then 15 μL of buffer C was added.

2.8 The reaction plate was placed into a 37° C. water bath incubator for 5 min. In the reaction plate, 15 μL of reduced coenzyme II solution was added to each well to initiate the reaction, and the time keeping was started. At the time points of 5, 15, 30, 45, and 60 min, 135 μL of iced acetonitrile containing the internal reference was added to each well to terminate the reaction.

2.9 The reaction plate was sealed with an aluminum film, placed on a vibration mixer and shaken at 500 rpm for 5 min. The plate was then centrifuged in a centrifuge at 3750 rp for 15 min.

2.10 The sample was diluted with pure water in accordance with the ratio of 1:1 and detected by LC/MS. The clearance ratio was calculated according to the following formula based on the obtained values, and shown in Table 7.

Half-life: 0.693/K (the slope by plotting based on the incubation time and logarithm of the concentration value)

Clearance ratio:(0.693/half-life)*(1/protein concentration(0.5 mg/mL))*(proportional factor)

Wherein, the K value and the proportional factor were calculated by those skilled in the art according to the methods described in the prior art and contained in the instructions of the liver microsome product.

TABLE 37

Experimental results of Metabolic stability of human liver microsomes

| Compound No. | human | |
|---|---|---|
| | $T_{1/2}$(min) | Clearance ratio (mL/min/kg) |
| the free base of formula X compound | 86.39 | 20.12 |
| C12 | 22.21 | 78.28 |
| C13 | 12.51 | 138.91 |

It can be seen from Table 37 that the free base of formula X compound have good metabolic stability. It has also been found that the change of the substituent $R_6$ has obvious influence on the metabolic stability. When cyclopropyl is changed to methyl, the metabolic stability is significantly reduced.

All publications mentioned herein are incorporated by reference as if each individual document was cited as a reference, as in the present application. It should also be understood that, after reading the above teachings of the present disclosure, those skilled in the art can make various changes or modifications, which, as equivalents, also falls into the scope as defined in the appended claims.

The invention claimed is:

1. A pharmaceutically acceptable salt of a compound of formula (X), or a polymorph thereof

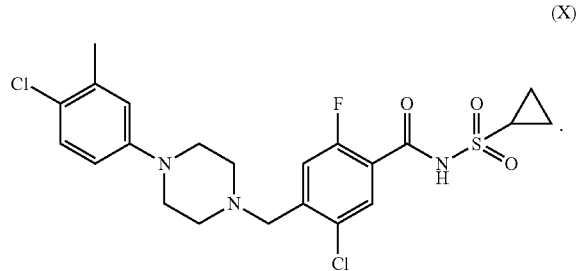 [SMILES: Cc1cc(N2CCN(Cc3cc(F)c(C(=O)NS(=O)(=O)C4CC4)cc3Cl)CC2)ccc1Cl]

(X)

2. The pharmaceutically acceptable salt of the compound according to claim 1, or a polymorph thereof, wherein the pharmaceutically acceptable salt is an acid salt or basic salt, wherein the acid salt is selected from the group consisting of hydrochloride, sulfate, phosphate, acetate, L-lactate, maleate, fumarate, succinate, L-malate, adipate, L-tartrate, hippurate, citrate, mucate, glycollate, D-glucuronate, benzoate, gentisate, nicotinate, ethanedisulphonate, oxalate, methanesulfonate, benzenesulfonate, 2-hydroxyethanesulfonate and hydrobromide; the basic salt is selected from the group consisting of triethanolamine salt, sodium salt and potassium salt.

3. The pharmaceutically acceptable salt of the compound according to claim 1, or a polymorph thereof, wherein the pharmaceutically acceptable salt of the compound of formula X, or a polymorph thereof is in an anhydrous form, hydrate form or solvate form.

4. The pharmaceutically acceptable salt of the compound according to claim 1, or a polymorph thereof, wherein the polymorph is a polymorph of the compound of formula X or a polymorph of the pharmaceutically acceptable salt of the compound of formula X, and the pharmaceutically acceptable salt is an acid salt or basic salt, wherein the acid salt is selected from the group consisting of hydrochloride, sulfate, hydrobromide, phosphate, methanesulfonate, maleate, L-tartrate, citrate and fumarate; the basic salt is selected from the group consisting of sodium salt and potassium salt.

5. The pharmaceutically acceptable salt of the compound according to claim 1, or a polymorph thereof, wherein the polymorph is selected from the group consisting of
(1) an A crystalline form of a hydrochloride of the compound of formula X, i.e. crystal form A, which has an X-ray powder diffraction pattern having peaks at diffraction angle 2θ(°) values of the following group A1: 12.19±0.20, 16.30±0.20, 17.76±0.20, 18.61±0.20, 23.23±0.20, and 25.17±0.20;
(2) a B crystalline form of a hydrobromide of the compound of formula X, i.e. crystal form B, which has an X-ray powder diffraction pattern having a peak at a diffraction angle 2θ(°) value of the following group B1: 12.40±0.20;
(3) a C crystalline form of a methanesulfonate of the compound of formula X, i.e. crystal form C, which has an X-ray powder diffraction pattern having peaks at diffraction angle 2θ(°) values of the following group C1: 8.93±0.20, 15.32±0.20, 21.86±0.20, 22.56±0.20, 23.75±0.20, 25.69±0.20, and 27.37±0.20;
(4) a D crystalline form of a maleate of the compound of formula X, i.e. crystal form D, which has an X-ray powder diffraction pattern having peaks at diffraction angle 2θ(°) values of the following group D1: 5.06±0.20, 8.24±0.20, 10.08±0.20, 15.14±0.20, 16.18±0.20, 18.95±0.20, 19.83±0.20, 20.40±0.20, 21.38±0.20, 22.14±0.20, and 26.51±0.20;
(5) an E-1 crystalline form of a sodium salt of compound of formula X, i.e. crystal form E-1, which has an X-ray powder diffraction pattern having a peak at a diffraction angle 2θ(°) value of the following group E-1-1: 4.53±0.20;
(6) an E-2 crystalline form of a sodium salt of the compound of formula X, i.e. crystal form E-2, which has an X-ray powder diffraction pattern having peaks at diffraction angle 2θ(°) values of the following group E-2-1: 6.90±0.20, 14.44±0.20, 16.96±0.20, 17.77±0.20, 18.42±0.20, 19.72±0.20, 22.22±0.20, 22.67±0.20, and 27.94±0.20;
(7) an E-3 crystalline form of a sodium salt of the compound of formula X, i.e. crystal form E-3, which has an X-ray powder diffraction pattern having peaks at diffraction angle 2θ(°) values of the following group E-3-1: 7.12±0.20, 7.57±0.20, 9.94±0.20, 10.71±0.20, and 17.68±0.20; and (8) an F crystalline form of a potassium salt of the compound of formula X, i.e. crystal form F, which has an X-ray powder diffraction pattern having peaks at diffraction angle 2θ(°) values of the following group F-1: 7.83±0.20, 17.68±0.20, and 18.74±0.20.

6. The pharmaceutically acceptable salt of the compound according to claim 1, or a polymorph thereof, wherein the polymorph is selected from the group consisting of (9) a I crystalline form of a free base of the compound of formula X, i.e. crystal form I, which has an X-ray powder diffraction pattern having peaks at diffraction angle 2θ(°) values of the group I-1: 7.26±0.20, 18.38±0.20, and 23.15±0.20;

(10) a II crystalline form of a free base of the compound of formula X, i.e. crystal form II, which has an X-ray powder diffraction pattern having peaks at diffraction angle 2θ(°) values of the group II-1: 6.84±0.20, 7.74±0.20, and 9.94±0.20;

(11) a III crystalline form of a free base of the compound of formula X, i.e. crystal form III, which has an X-ray powder diffraction pattern having a peak at a diffraction angle 2θ(°) value of the group III-1: 4.09±0.20;

(12) a IV crystalline form of a free base of the compound of formula X, i.e. crystal form IV, which has an X-ray powder diffraction pattern having a peak at a diffraction angle 2θ(°) value of the group IV-1: 4.66±0.20;

(13) a V crystalline form of a free base of the compound of formula X, i.e. crystal form V, which has an X-ray powder diffraction pattern having peaks at diffraction angle 2θ(°) values of the group V-1: 6.79±0.20, 14.31±0.20, 16.90±0.20, 17.58±0.20, 20.58±0.20, 21.90±0.20, and 23.45±0.20;

(14) a VI crystalline form of a free base of the compound of formula X, i.e. crystal form VI, which has an X-ray powder diffraction pattern having peaks at diffraction angle 2θ(°) values of the group VI-1: 6.90±0.20, 7.14±0.20, 16.40±0.20, 16.92±0.20, 20.62±0.20, and 23.52±0.20;

(15) a VII crystalline form of a free base of the compound of formula X, i.e. crystal form VII, which has an X-ray powder diffraction pattern having peaks at diffraction angle 2θ(°) values of the group VII-1: 7.11±0.20, and 14.22±0.20.

Figure 5A:
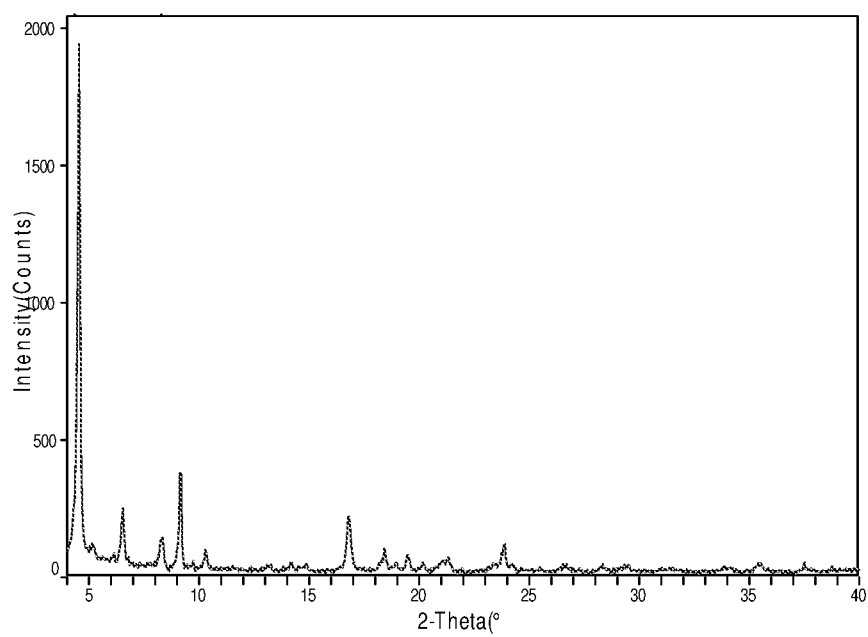
FIG. 5A is the X-ray powder diffraction pattern of crystal form E-1.
Figure 5B:
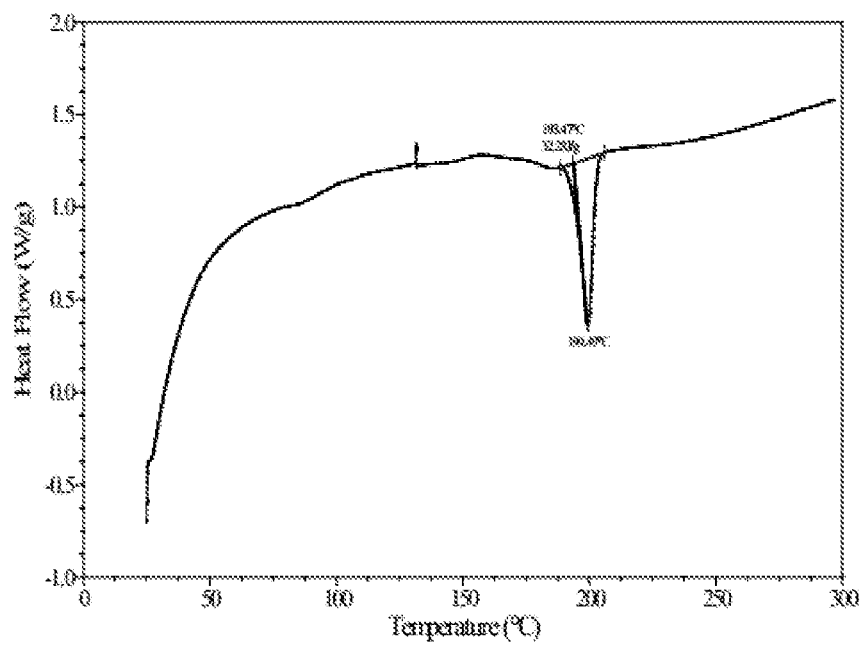
FIG. 5B is the differential scanning calorimetry analysis spectrum of crystal form E-1.
Figure 6A:
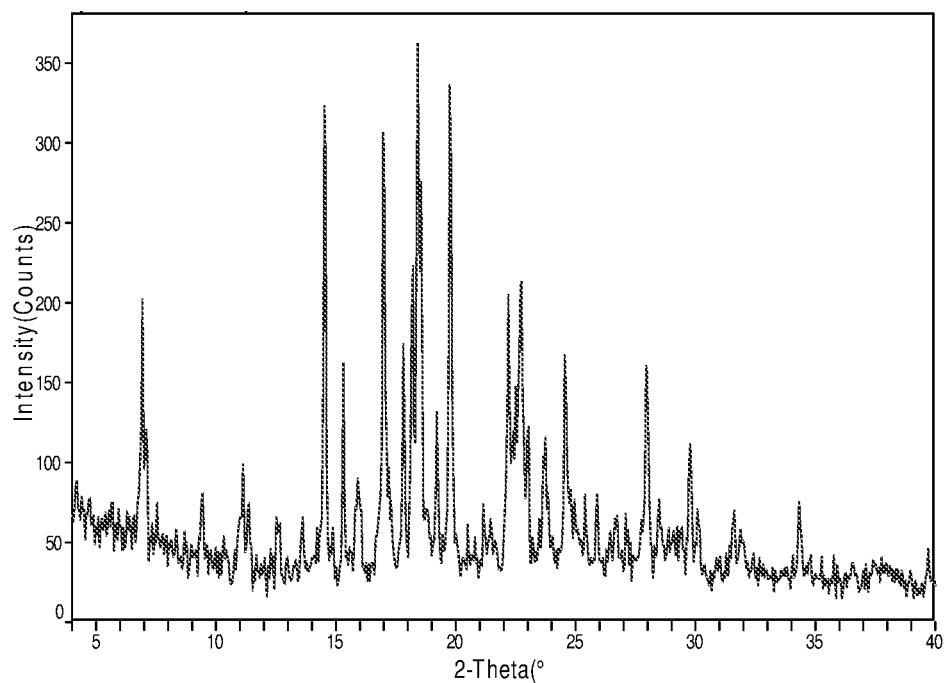
FIG. 6A is the X-ray powder diffraction pattern of crystal form E-2.
Figure 6B:
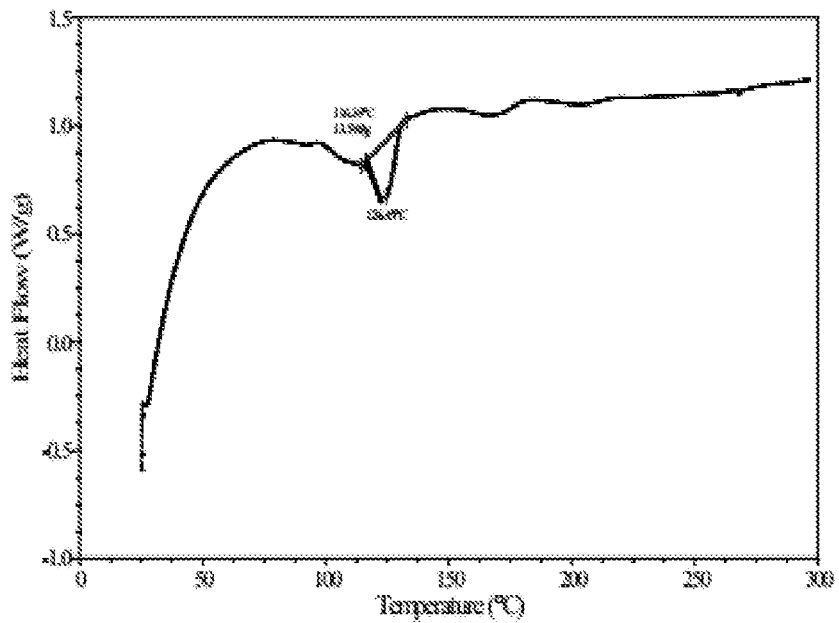
FIG. 6B is the differential scanning calorimetry analysis spectrum of crystal form E-2.

7. The pharmaceutically acceptable salt of the compound according to claim 1, or a polymorph thereof, wherein
the X-ray powder diffraction pattern of crystal form A is substantially as shown in FIG. 1A;
the X-ray powder diffraction pattern of crystal form B is substantially as shown in FIG. 2A;
the X-ray powder diffraction pattern of crystal form C is substantially as shown in FIG. 3A;
the X-ray powder diffraction pattern of crystal form D is substantially as shown in FIG. 4A;
the X-ray powder diffraction pattern of crystal form E-1 is substantially as shown in FIG. 5A;
the X-ray powder diffraction pattern of crystal form E-2 is substantially as shown in FIG. 6A;
the X-ray powder diffraction pattern of crystal form E-3 is substantially as shown in FIG. 7A;
the X-ray powder diffraction pattern of crystal form F is substantially as shown in FIG. 8A;
the X-ray powder diffraction pattern of crystal form I is substantially as shown in FIG. 9A;
the X-ray powder diffraction pattern of crystal form II is substantially as shown in FIG. 10A;
the X-ray powder diffraction pattern of crystal form III is substantially as shown in FIG. 11A;
the X-ray powder diffraction pattern of crystal form IV is substantially as shown in FIG. 12A;
the X-ray powder diffraction pattern of crystal form V is substantially as shown in FIG. 13A;
the X-ray powder diffraction pattern of crystal form VI is substantially as shown in FIG. 14A; and
the X-ray powder diffraction pattern of crystal form VII is substantially as shown in FIG. 15A.

8. A process for preparing a pharmaceutically acceptable salt of a compound of formula X or a polymorph thereof, wherein the process comprises the following steps:

(1) reacting a compound of formula X-4 with a compound of formula X-a under an alkaline condition to form the compound of formula X;

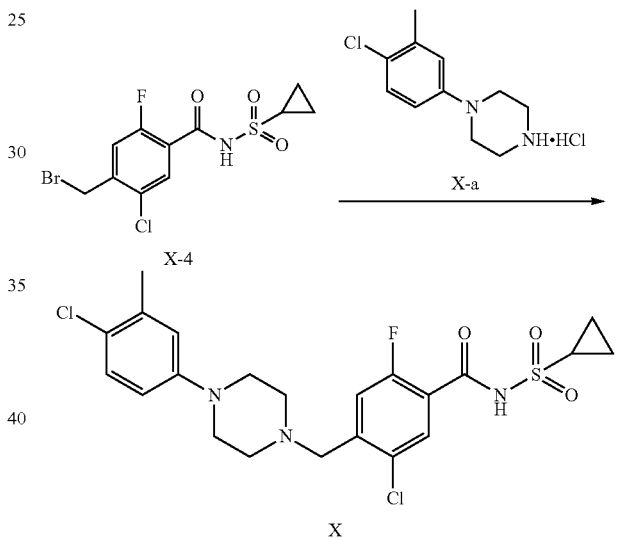

(2) optionally, reacting the compound of formula X with an acid or a base to form a pharmaceutically acceptable salt of the compound of formula X;

(3) optionally, performing crystallization processing on the compound of formula X formed in step (1), or the pharmaceutically acceptable salt of the compound of formula X formed in step (2), to obtain a polymorph of the compound of formula X or a polymorph of the pharmaceutically acceptable salt of the compound of formula X.

9. A pharmaceutical composition, wherein the pharmaceutical composition comprises:

(a) the pharmaceutically acceptable salt of the compound of formula X or the polymorph thereof according to claim 1; and (b) a pharmaceutically acceptable carrier.

* * * * *